US009714285B2

(12) United States Patent
Bedinger et al.

(10) Patent No.: US 9,714,285 B2
(45) Date of Patent: *Jul. 25, 2017

(54) TGF-BETA-SPECIFIC ANTIBODIES AND METHODS OF USE THEREOF FOR TREATMENT

(71) Applicant: XOMA TECHNOLOGY LTD., Berkeley, CA (US)

(72) Inventors: Daniel Bedinger, Vacaville, CA (US); Shireen S. Khan, Castro Valley, CA (US); Amer Mirza, San Francisco, CA (US); Ajay J. Narasimha, San Francisco, CA (US); Toshihiko Takeuchi, Oakland, CA (US)

(73) Assignee: XOMA TECHNOLOGY LTD., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/808,666

(22) Filed: Jul. 24, 2015

(65) Prior Publication Data

US 2015/0322146 A1 Nov. 12, 2015

Related U.S. Application Data

(63) Continuation of application No. 14/038,436, filed on Sep. 26, 2013, now Pat. No. 9,145,458, which is a continuation of application No. 13/486,983, filed on Jun. 1, 2012, now Pat. No. 8,569,462.

(60) Provisional application No. 61/493,230, filed on Jun. 3, 2011.

(51) Int. Cl.
*C07K 16/22* (2006.01)
*A61K 39/00* (2006.01)

(52) U.S. Cl.
CPC ........ *C07K 16/22* (2013.01); *A61K 2039/505* (2013.01); *C07K 2317/21* (2013.01); *C07K 2317/30* (2013.01); *C07K 2317/55* (2013.01); *C07K 2317/56* (2013.01); *C07K 2317/565* (2013.01); *C07K 2317/567* (2013.01); *C07K 2317/64* (2013.01); *C07K 2317/76* (2013.01); *C07K 2317/92* (2013.01)

(58) Field of Classification Search
CPC C07K 16/22; C07K 2317/21; C07K 2317/30; C07K 2317/55; C07K 2317/56; C07K 2317/565; C07K 2317/567; C07K 2317/64; C07K 2317/76; C07K 2317/92; A61K 2039/505

See application file for complete search history.

(56) References Cited

U.S. PATENT DOCUMENTS

| | | |
|---|---|---|
| 4,391,904 A | 7/1983 | Litman et al. |
| 4,676,980 A | 6/1987 | Segal et al. |
| 4,816,567 A | 3/1989 | Cabilly et al. |
| 5,057,313 A | 10/1991 | Shih et al. |
| 5,223,409 A | 6/1993 | Ladner et al. |
| 5,229,275 A | 7/1993 | Goroff |
| 5,348,867 A | 9/1994 | Georgiou et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,571,714 A | 11/1996 | Dasch et al. |
| 5,573,905 A | 11/1996 | Lerner et al. |
| 5,589,369 A | 12/1996 | Seidman et al. |
| 5,591,669 A | 1/1997 | Krimpenfort et al. |
| 5,591,828 A | 1/1997 | Bosslet et al. |
| 5,624,821 A | 4/1997 | Winter et al. |
| 5,643,768 A | 7/1997 | Kawasaki |
| 5,658,754 A | 8/1997 | Kawasaki |
| 5,723,287 A | 3/1998 | Russell et al. |
| 5,766,886 A | 6/1998 | Studnicka et al. |
| 5,770,429 A | 6/1998 | Lonberg et al. |
| 5,772,998 A | 6/1998 | Dasch et al. |
| 5,783,185 A | 7/1998 | Dasch et al. |
| 5,877,293 A | 3/1999 | Adair et al. |
| 5,939,598 A | 8/1999 | Kucherlapati et al. |
| 5,969,108 A | 10/1999 | McCafferty et al. |
| 6,054,287 A | 4/2000 | Gao et al. |
| 6,090,383 A | 7/2000 | Dasch et al. |
| 6,091,001 A | 7/2000 | Jakobovits et al. |
| 6,114,598 A | 9/2000 | Kucherlapati et al. |
| 6,306,393 B1 | 10/2001 | Goldenberg |
| 6,328,963 B1 | 12/2001 | Kitagawa et al. |

(Continued)

FOREIGN PATENT DOCUMENTS

| | | |
|---|---|---|
| CN | 101163502 A | 4/2008 |
| EP | 1391213 A1 | 2/2004 |

(Continued)

OTHER PUBLICATIONS

Abe et al., An assay for transforming growth factor-beta using cells transfected with a plasminogen activator inhibitor-1 promoter-luciferase construct, Anal. Biochem., 216(2):276-84 (1994).
Amstutz et al., In vitro display technologies: novel developments and applications, Curr. Opin. Biotechnol., 12(4):400-5 (2001).
Angal et al., A single amino acid substitution abolishes the heterogeneity of chimeric mouse/human (IgG4) antibody, Mol. Immunol., 30(1):105-8 (1993).
Armour et al., Differential binding to human FcgammaRIIa and FcgammaRIIb receptors by human IgG wildtype and mutant antibodies, Mol. Immunol., 40(9): 585-93 (2003).
Barbas et al., Assembly of combinatorial antibody libraries on phage surfaces: the gene III site, Proc. Natl. Acad. Sci. USA, 88(18):7978-82 (1991).

(Continued)

*Primary Examiner* — Robert Landsman
(74) *Attorney, Agent, or Firm* — Marshall, Gerstein & Borun LLP

(57) ABSTRACT

The present disclosure relates, in general, to materials and methods for antibodies specific for transforming growth factor beta (TGFβ), including TGFβ1, TGFβ2 and TGFβ3, and uses of these antibodies in the treatment of subjects having cancer, an eye disease, condition or disorder, fibrosis, including ophthalmic fibrosis or fibrosis of the eye, and other conditions or disorders related to TGFβ expression.

20 Claims, 22 Drawing Sheets

(56) References Cited

U.S. PATENT DOCUMENTS

| | | |
|---|---|---|
| 6,419,928 B1 | 7/2002 | Dasch et al. |
| 6,489,145 B1 | 12/2002 | Short |
| 6,492,497 B1 | 12/2002 | Thompson et al. |
| 6,605,449 B1 | 8/2003 | Short |
| 6,657,103 B1 | 12/2003 | Kucherlapati et al. |
| 6,664,114 B1 | 12/2003 | Lackie et al. |
| 6,699,658 B1 | 3/2004 | Wittrup et al. |
| 6,737,056 B1 | 5/2004 | Presta |
| 6,790,938 B1 | 9/2004 | Berchtold et al. |
| 6,833,268 B1 | 12/2004 | Green et al. |
| 7,151,169 B2 | 12/2006 | Thompson et al. |
| 7,369,111 B2 | 5/2008 | Jeon et al. |
| 7,494,651 B2 | 2/2009 | Jones et al. |
| 7,527,791 B2 | 5/2009 | Adams et al. |
| 7,723,486 B2 | 5/2010 | Ledbetter et al. |
| 7,763,244 B2 | 7/2010 | Rosen |
| 7,867,496 B2 | 1/2011 | Khanna et al. |
| 7,919,593 B2 | 4/2011 | Papadopoulos et al. |
| 7,927,593 B2 | 4/2011 | Jones et al. |
| 8,569,462 B2 | 10/2013 | Bedinger et al. |
| 9,145,458 B2 | 9/2015 | Bedinger et al. |
| 2002/0004215 A1 | 1/2002 | Osbourn et al. |
| 2002/0199213 A1 | 12/2002 | Tomizuka et al. |
| 2003/0028071 A1 | 2/2003 | Handy et al. |
| 2003/0031667 A1 | 2/2003 | Deo et al. |
| 2003/0032995 A1 | 2/2003 | Handy et al. |
| 2003/0044772 A1 | 3/2003 | Watkins et al. |
| 2003/0092125 A1 | 5/2003 | Davis et al. |
| 2003/0118592 A1 | 6/2003 | Ledbetter et al. |
| 2003/0133939 A1 | 7/2003 | Ledbetter et al. |
| 2003/0190731 A1 | 10/2003 | Baca et al. |
| 2003/0194404 A1 | 10/2003 | Greenfeder et al. |
| 2004/0132101 A1 | 7/2004 | Lazar et al. |
| 2005/0037421 A1 | 2/2005 | Honda et al. |
| 2005/0136049 A1 | 6/2005 | Ledbetter et al. |
| 2005/0276802 A1 | 12/2005 | Adams et al. |
| 2006/0251658 A1 | 11/2006 | Ledbetter et al. |
| 2008/0292638 A1 | 11/2008 | Jones et al. |
| 2009/0258005 A1 | 10/2009 | Gill et al. |
| 2010/0047243 A1 | 2/2010 | Burden et al. |
| 2010/0297636 A1 | 11/2010 | Vincent et al. |
| 2010/0322924 A1 | 12/2010 | Johnson et al. |
| 2011/0008364 A1 | 1/2011 | Ledbetter et al. |
| 2011/0065176 A1 | 3/2011 | Yoo et al. |

FOREIGN PATENT DOCUMENTS

| | | |
|---|---|---|
| WO | WO-94/11026 A2 | 5/1994 |
| WO | WO-00/40227 A2 | 7/2000 |
| WO | WO-03/041600 A1 | 5/2003 |
| WO | WO-2006/086469 A2 | 8/2006 |
| WO | WO-2007/076391 A1 | 7/2007 |
| WO | WO-2009/088933 A1 | 7/2009 |
| WO | WO-2010003118 A1 | 1/2010 |

OTHER PUBLICATIONS

Batra et al., Recombinant anti-erbB2 immunotoxins containing Pseudomonas exotoxin, Proc. Natl. Acad. Sci. USA, 89(13):5867-71 (1992).
Becker et al., An antibody-interleukin 2 fusion protein overcomes tumor heterogeneity by induction of a cellular immune response, Proc. Natl. Acad. Sci. USA, 93(15):7826-31 (1996).
Bhowmick et al., Transforming growth factor-beta1 mediates epithelial to mesenchymal transdifferentiation through a RhoA-dependent mechanism, Mol. Biol. Cell., 12(1):27-36 (2001).
Biocca et al., Expression and targeting of intracellular antibodies in mammalian cells, EMBO J., 9(1):101-8 (1990).
Birch et al., Antibody production, Adv. Drug Deliv. Rev., 58(5-6):671-85 (2006).
Biswas et al., Inhibition of TGF-beta with neutralizing antibodies prevents radiation-induced acceleration of metastatic cancer progression, J. Clin. Invest., 117(5):1305-13 (2007).
Boleti et al., Construction, expression and characterisation of a single chain anti-tumour antibody (scFv)-IL-2 fusion protein, Ann. Oncol., 6(9):945-7 (1995).
Border et al., Transforming growth factor beta in tissue fibrosis, N. Engl. J. Med., 331(19):1286-92 (1994).
Boyer et al., TGFbeta2 and TGFbeta3 have separate and sequential activities during epithelial-mesenchymal cell transformation in the embryonic heart, Dev. Biol., 208(2):530-45 (1999).
Brinkmann et al., B3(Fv)-PE38KDEL, a single-chain immunotoxin that causes complete regression of a human carcinoma in mice, Proc. Natl. Acad. Sci. USA, 88(19):8616-20 (1991).
Camenisch et al., Temporal and distinct TGFbeta ligand requirements during mouse and avian endocardial cushion morphogenesis, Dev. Biol., 248(1):170-81 (2002).
Chowdhury, Targeting random mutations to hotspots in antibody variable domains for affinity improvement, Methods Mol. Biol., 178:269-85 (2002).
Colby et al., Potent inhibition of huntingtin aggregation and cytotoxicity by a disulfide bond-free single-domain intracellular antibody, Proc. Natl. Acad. Sci. USA, 101(51):17616-21 (2004).
Colman, Effects of amino acid sequence changes on antibody-antigen interactions, Res. Immunol., 145:33-6 (1994).
Conrath et al., Beta-lactamase inhibitors derived from single-domain antibody fragments elicited in the camelidae, Antimicro. Agents Chemother., 45(10):2807-12 (2001).
Cortez-Retamozo et al., Efficient cancer therapy with a nanobody-based conjugate, Cancer Res., 64(8):2853-7 (2004).
Cunningham et al., High-resolution epitope mapping of hGH-receptor interactions by alanine-scanning mutagenesis, Science, 244(4908):1989).
Czarniecki et al., Transforming growth factor-beta 1 modulates the expression of class II histocompatibility antigens on human cells, J. Immunol., 140(12):4217-23 (1988).
Dancea et al., Role of radiation-induced TGF-beta signaling in cancer therapy, Mol. Cell. Pharmacol., 1(1):44-56 (2009).
Danielpour et al., Immunodetection and quantitation of the two forms of transforming growth factor-beta (TGF-beta 1 and TGF-beta 2) secreted by cells in culture, J. Cell Physiol., 138(1):79-86 (1989).
Daugherty et al., Quantitative analysis of the effect of the mutation frequency on the affinity maturation of single chain Fv antibodies, Proc. Natl. Acad. Sci. USA, 97(5):2029-34 (2000).
de Martin et al., Complementary DNA for human glioblastoma-derived T cell suppressor factor, a novel member of the transforming growth factor-beta gene family, EMBO J., 6(12):3673-7 (1987).
Demetriou et al., Fetuin/alpha2-HS glycoprotein is a transforming growth factor-beta type II receptor mimic and cytokine antagonist, J. Biol. Chem., 271(22):12755-61 (1996).
Deonarain et al., Tumor Targeting, 1:177 (1995).
Derynck et al., Synthesis of messenger RNAs for transforming growth factors alpha and beta and the epidermal growth factor receptor by human tumors, Cancer Res., 47(3):707-12 (1987).
Desmyter et al., Antigen specificity and high affinity binding provided by one single loop of a camel single-domain antibody, J. Biol. Chem., 276(28):26285-90 (2001).
Dohlsten et al., Monoclonal antibody-superantigen fusion proteins: tumor-specific agents for T-cell-based tumor therapy, Proc. Natl. Acad. Sci. USA, 91(19):8945-9), (1994).
Doronina et al., Development of potent monoclonal antibody auristatin conjugates for cancer therapy, Nat. Biotechnol., 21(7):778-84 (2003).
Espevik et al., Transforming growth factor-beta 1 (TGF-beta 1) and recombinant human tumor necrosis factor-alpha reciprocally regulate the generation of lymphokine-activated killer cell activity. Comparison between natural porcine platelet-derived TGF-beta 1 and TGF-beta 2, and recombinant human TGF-beta 1, J. Immunol., 140(7):2312-6 (1988).
Ewert et al., Biophysical properties of camelid V(HH) domains compared to those of human V(H)3 domains, Biochemistry, 41(11):3628-36 (2002).
Fastenberg et al., The role of cellular proliferation in an experimental model of massive periretinal proliferation, Am. J. Ophthalmol., 93(5):565-72 (1982).

(56) References Cited

OTHER PUBLICATIONS

Ferrara et al., Modulation of therapeutic antibody effector functions by glycosylation engineering: influence of Golgi enzyme localization domain and co-expression of heterologous beta1, 4-N-acetylglucosaminyltransferase III and Golgi alpha-mannosidase II, Biotechnol. Bioeng., 93(5):851-61 (2006).
Field et al., Purification of a RAS-responsive adenylyl cyclase complex from *Saccharomyces cerevisiae* by use of an epitope addition method, Mol. Cell Biol., 8(5):2159-65 (1988).
Flavell et al., The polarization of immune cells in the tumour environment by TGFbeta, Nat. Rev. Immunol., 10(8):554-67 (2010).
Fleer et al., Stable multicopy vectors for high-level secretion of recombinant human serum albumin by Kluyveromyces yeasts, Biotechnology (NY): 9(10):968-75 (1991).
Florini et al., Transforming growth factor-beta. A very potent inhibitor of myoblast differentiation, identical to the differentiation inhibitor secreted by Buffalo rat liver cells, J. Biol. Chem., 261(35):16509-13 (1986).
Friedman et al., Antitumor activity of the single-chain immunotoxin BR96 sFv-PE40 against established breast and lung tumor xenografts, J. Immunol., 150(7):3054-61 (1991).
Fuchs et al., Targeting recombinant antibodies to the surface of *Escherichia coli*: fusion to a peptidoglycan associated lipoprotein, Bio/Technology, 9:1369-73 (Dec. 1991).
Garrard et al., Fab assembly and enrichment in a monovalent phage display system, Bio/Technology, 9(12):1373-7 (1991).
Gioia et al., UniProt Accession A8FJDF4 (Feb. 8, 2011); downloaded from the Internet at: <http://www.uniprot.org/uniprot/A8FJD4.txt?version=17> on Sep. 17, 2012.
Gram et al., In vitro selection and affinity maturation of antibodies from a naive combinatorial immunoglobulin library, Proc. Natl. Acad. Sci. USA, 89(8):3576-80 (1992).
Greenberg et al., A new antigen receptor gene family that undergoes rearrangement and extensive somatic diversification in sharks, Nature, 374(6518):168-73 (1995).
Gruber et al., Efficient tumor cell lysis mediated by a bispecific single chain antibody expressed in *Escherichia coli*, J. Immunol., 152(11):5368-74 (1994).
Guss et al., Structure of the IgG-binding regions of streptococcal protein G, EMBO J., 5(7):1567-75 (1986).
Hamers-Casterman et al., Naturally occurring antibodies devoid of light chains, Nature, 363(6428):446-8 (1993).
Han et al., Favorable treatment outcome with neutralizing anti-transforming growth factor beta antibodies in experimental diabetic kidney disease, Perit. Dial. Int., 19 Suppl 2:S234-7 (1999).
Hanes et al., In vitro selection and evolution of functional proteins by using ribosome display, Proc. Natl. Acad. Sci. USA, 94(10):4937-42 (1997).
Hank et al., Activation of human effector cells by a tumor reactive recombinant anti-ganglioside GD2 interleukin-2 fusion protein (ch14.18-IL2), Clin. Cancer Res., 2(12):1951-9 (1996).
Hawinkels et al., Exploring anti-TGF-β therapies in cancer and fibrosis, Growth Factors, 29(4):140-52 (2011).
Heng et al., Making cell-permeable antibodies (Transbody) through fusion of protein transduction domains (PTD) with single chain variable fragment (scFv) antibodies: potential advantages over antibodies expressed within the intracellular environment (Intrabody), Med. Hypotheses, 64(6):1105-8 (2005).
Hinman et al., Preparation and characterization of monoclonal antibody conjugates of the calicheamicins: a novel and potent family of antitumor antibiotics, Cancer Res., 53(14):3336-42 (1993).
Hoefer et al., Anti-(transforming growth factor beta) antibodies with predefined specificity inhibit metastasis of highly tumorigenic human xenotransplants in nu/nu mice, Cancer Immunol. Immunother., 41(5):302-8 (1995).
Holley et al., Purification of kidney epithelial cell growth inhibitors, Proc. Natl. Acad. Sci. USA, 77(10):5989-92 (1980).
Holliger et al., "Diabodies": small bivalent and bispecific antibody fragments, Proc. Natl. Acad. Sci. USA, 90(14):6444-8 (1993).
Holliger et al., Engineered antibody fragments and the rise of single domains, Nat. Biotechnol., 23(9):1126-36 (2005).
Hoogenboom et al., By-passing immunisation. Human antibodies from synthetic repertoires of germline VH gene segments rearranged in vitro, J. Mol. Biol., 227(2):381-8 (1992).
Hoogenboom et al., Multi-subunit proteins on the surface of filamentous phage: methodologies for displaying antibody (Fab) heavy and light chains, Nucleic Acids Res., 19(15):413-7 (1991).
Hu et al., A chimeric Lym-1/interleukin 2 fusion protein for increasing tumor vascular permeability and enhancing antibody uptake, Cancer Res., 56(21):4998-5004 (1996).
Huls et al., Tumor cell killing by in vitro affinity-matured recombinant human monoclonal antibodies, Cancer Immunol. Immunother., 50(3):163-71 (2001).
Huse et al., Generation of a large combinatorial library of the immunoglobulin repertoire in phage lambda, Science, 246-1275-81 (1989).
Huston et al., Protein engineering of antibody binding sites: recovery of specific activity in an anti-digoxin single-chain Fv analogue produced in *Escherichia coli*, Proc. Natl. Acad. Sci. USA, 85(16):5879-83 (1988).
International Search Report and Written Opinion for corresponding international application No. PCT/US12/40545, mailing date Oct. 2, 2012.
Isaacs et al., Therapy with monoclonal antibodies. II. The contribution of Fc gamma receptor binding and the influence of C(H)1 and C(H)3 domains on in vivo effector function, J. Immunol., 161(8):3862-9 (1998).
Ishida et al., Production of human monoclonal and polyclonal antibodies in TransChromo animals, Cloning Stem Cells, 4(1):91-102 (2002).
Israels et al., Role of transforming growth factor-beta in chronic lymphocytic leukemia, Leuk. Res., 17(1)81-7 (1993).
Jespers et al., Guiding the selection of human antibodies from phage display repertoires to a single epitope of an antigen, Bio/Technology, 12(9):899-903 (1994).
Jones et al., Replacing the complementarity-determining regions in a human antibody with those from a mouse, Nature, 321(6069):522-5 (1986).
Kabat et al., Sequences of Proteins of Immunological Interest, Bethesda, MD: U.S. Dept. of Health and Human services, Public Health Service, National Institutes of Health (1987 and 1991).
Kettleborough et al., Humanization of a mouse monoclonal antibody by CDR-grafting: the importance of framework residues on loop conformation, Protein Eng., 4(7):773-83 (1991).
Kohler et al., Continuous cultures of fused cells secreting antibody of predefined specificity, Nature, 256(5517):495-7 (1975).
Kostelny et al., Formation of a bispecific antibody by the use of leucine zippers, J. Immunol., 148(5):1547-53 (1992).
Kuan et al., Recombinant immunotoxin containing a disulfide-stabilized Fv directed at erbB2 that does not require proteolytic activation, Biochemistry, 35(9):2872-7 (1996).
Lee et al., Beta transforming growth factors are potential regulators of B lymphopoiesis, J. Exp. Med., 166(5):1290-9 (1987).
Lefranc et al., IMGT unique numbering for immunoglobulin and T cell receptor variable domains and Ig superfamily V-like domains, Dev. Comp. Immunol., 27(1):55-77 (2003).
Li et al., Cancer-expanded myeloid-derived suppressor cells induce anergy of NK cells through membrane-bound TGF-beta 1, J. Immunol., 182(1):240-9 (2009).
Li et al., Lyn mitigates mouse airway remodeling by downregulating the TGF-β3 isoform in house dust mite models, J. Immunol., 191(11):5359-70 (2013).
Lindmark et al., Binding of immunoglobulins to protein A and immunoglobulin levels in mammalian sera, J. Immunol. Methods, 62(1):1-13 (1983).
Ling et al., Attenuation of renal ischemia-reperfusion injury in inducible nitric oxide synthase knockout mice, Am. J. Physiol., 277(3 Pt. 2):F383-90 (1999).

(56) References Cited

OTHER PUBLICATIONS

Ling et al., Therapeutic role of TGF-beta-neutralizing antibody in mouse cyclosporin A nephropathy: morphologic improvement associated with functional preservation, J. Am. Soc. Nephrol., 14(2):377-88 (2003).
Liu et al., Eradication of large colon tumor xenografts by targeted delivery of maytansinoids, Proc. Natl. Acad. Sci. USA, 93(16):8618-23 (1996).
Lode et al., Targeted therapy with a novel enediyene antibiotic calicheamicin $\Theta^1$ effectively suppresses growth and dissemination of liver metastases in a syngeneic model of murine neuroblastoma, Cancer Res., 58:2925-8 (1998).
Low et al., Mimicking somatic hypermutation: affinity maturation of antibodies displayed on bacteriophage using a bacterial mutator strain, J. Mol. Biol., 260(3):359-68 (1996).
Lucas et al., UniProt Accession F2JKF8 (May 31, 2011): downloaded from the Internet at: <http://www.uniprot.org/uniprot/F2JKF8.txt?version=1> on Sep. 17, 2012.
Lutjen-Drecoll, Morphological changes in glaucomatous eyes and the role of TGFbeta2 for the pathogenesis of the disease, Exp. Eye Res., 81(1):1-4 (2005).
MacLellan et al., Genetic dissection of cardiac growth control pathways, Annu. Rev. Physiol., 62:289-319 (2000).
Mandler et al., Immunoconjugates of geldanamycin and anti-HER2 monoclonal antibodies: antiproliferative activity on human breast carcinoma cell lines, J. Natl. Cancer Inst., 92(19)1573-81 (2000).
Mandler et al., Synthesis and evaluation of antiproliferative activity of a geldanamycin-Herceptin immunoconjugate, Bioorg. Med. Chem. Lett., 10(10):1025-8 (2000).
Mani et al., The epithelial-mesenchymal transition generates cells with properties of stem cells, Cell, 133(4):704-15 (2008).
Marks et al., By-passing immunization: building high affinity human antibodies by chain shuffling, Biotechnology, 10(7):779-83 (1992).
Massey, Catalytic antibodies catching on, Nature, 328:457-8 (1987).
Mather et al., Culture of testicular cells in hormone-supplemented serum-free medium, Ann NY Acad. Sci., 383:44-68 (1982).
Mead et al., Evaluation of anti-TGF-beta2 antibody as a new postoperative anti-scarring agent in glaucoma surgery, Invest. Ophthalmol. Vis. Sci., 44(8):3394-401 (2003).
Mhashilkar et al., Inhibition of HIV-1 Tat-mediated LTR transactivation and HIV-1 infection by anti-Tat single chain intrabodies, EMBO J., 14(7):1542-51 (1995).
Miyazono et al., Tumour promoting functions of TGF-β in CML-initiating cells, *J. Biochem.*, 152(5)383-5 (2012).
Morrison et al., Chimeric human antibody molecules: mouse antigen-binding domains with human constant region domains, Proc. Natl. Acad. Sci. USA, 81(21):6851-5 (1984).
Morrison et al., Genetically engineered antibody molecules, Adv. Immunol., 44:65-92 (1989).
Nagaraj et al., Targeting the transforming growth factor-beta signaling pathway in human cancer, Expert Opin. Investig. Drugs, 19(1):77-91 (2010).
Nam et al., Transforming growth factor beta subverts the immune system into directly promoting tumor growth through interleukin-17, Cancer Res., 68(10):3915-23 (2008).
Neri et al., High-affinity antigen binding by chelating recombinant antibodies (CRAbs), J. Mol. Biol., 246(3):367-73 (1995).
Neuberger et al., Recombinant antibodies possessing novel effector functions, Nature, 312(5995):604-8 (1984).
Nguyen et al., The specific variable domain of camel heavy-chain antibodies is encoded in the germline, J. Mol. Biol., 275(3):413-8 (1998).
Nicholls et al., Characterization of single-chain antibody (sFv)-toxin fusion proteins produced in vitro in rabbit reticulocyte lysate, J. Biol. Chem., 268(7):5302-8 (1993).
Nicolet et al., Expression of a tumor-reactive antibody-interleukin 2 fusion protein after in vivo particle-mediated gene delivery, Cancer Gene Ther., 2(3):161-70 (1995).

Niitsu et al., Expression of TGF-beta gene in adult T cell leukemia, *Blood*, 71(1):263-6 (1988).
Nishimiya et al., Thermodynamic consequences of grafting enhanced affinity toward the mutated antigen onto an antibody. The case of anti-lysozyme antibody, HyHEL-10, J. Biol. Chem., 275(17):12813-20 (2000).
Nuttall et al., Isolation of the new antigen receptor from wobbegong sharks, and use as a scaffold for the display of protein loop libraries, Mol. Immunol., 38(4):313-26 (2001).
Olafsen et al., Characterization of engineered anti-p185HER-2 (scFv-CH3)2 antibody fragments (minibodies) for tumor targeting, Protein Eng. Des. Sel., 17(4):315-23 (2004).
Oshima et al., Gene transfer of soluble TGF-beta type II receptor inhibits experimental proliferative vitreoretinopathy, Gene Ther., 9(18):1214-20 (2002).
Padlan, a possible procedure for reducing the immunogenicity of antibody variable domains while preserving their ligand-binding properties, Mol. Immunol., 28(4-5):489-98 (1991).
Padlan, Anatomy of the antibody molecule, Mol. Immunol., 31(3):169-217 (1994).
Pastan et al., Immunotoxin therapy of cancer, Nat. Rev. Cancer, 6(7):559-65 (2006).
Paul (ed.), Fundamental Immunology, Third Edition, pp. 292-5, New York: Raven Press (1993).
Petit-Koskas et al., Inhibition of the proliferative response of human B lymphocytes to B cell growth factor by transforming growth factor-beta, Eur. J. Immunol., 18(1):111-6 (1988).
Pircher et al., Beta-transforming growth factor is stored in human blood platelets as a latent high molecular weight complex, Biochem. Biophys. Res. Commun., 136(1):30-7 (1986).
Pohlers et al., TGF-beta and fibrosis in different organs—molecular pathway imprints, Biochim. Biophys. Acta., 1792(8):746-56 (2009).
Poljak, Production and structure of diabodies, Structure, 2(12):1121-3 (1994).
Portolano et al., Lack of promiscuity in autoantigen-specific H and L chain combinations as revealed by human H and L chain "roulette", J. Immunol., 150(3):880-7 (1993).
Prud-homme, Pathobiology of transforming growth factor 6 in cancer, fibrosis, and immunologic disease, and therapeutic considerations, Laboratory Investigation, 87:1077-91 (2007).
Rajpal et al., A general method for greatly improving the affinity of antibodies by using combinatorial libraries, Proc. Natl. Acad. Sci. USA, 102(24):8466-71 (2005).
Raju, Terminal sugars of Fc glycans influence antibody effector functions of IgGs, Curr. Opin. Immunol., 20(4):471-8 (2008).
Ranges et al., Inhibition of cytotoxic T cell development by transforming growth factor beta and reversal by recombinant tumor necrosis factor alpha, J. Exp. Med., 166(4):991-8 (1987).
Reichman et al., Single domain antibodies: comparison of camel VH and camelised human VH domains, J. Immunol. Methods, 231:25-38 (1999).
Reyes et al., Expression of human beta-interferon cDNA under the control of a thymidine kinase promoter from herpes simplex virus, Nature, 297(5867):598-601 (1982).
Riechmann et al., Reshaping human antibodies for therapy, Nature, 332(6162):323-7 (1988).
Roberts et al., New class of transforming growth factors potentiated by epidermal growth factor: isolation from non-neoplastic tissues, Proc. Natl. Acad. Sci. USA, 78(9):5339-43 (1983).
Roberts et al., Transforming growth factor-beta: possible roles in carcinogenesis, Br. J. Cancer, 57(6):594-600 (1988).
Rudikoff et al., Single amino acid substitution altering antigen-binding specificity, *Proc. Natl. Acad. Sci. USA*, 79(6):1979-83 (1982).
Saika et al., Expression of Smad7 in mouse eyes accelerates healing of corneal tissue after exposure to alkali, Am. J. Pathol., 166(5):1405-18 (2005).
Saika et al., Smad3 signaling is required for epithelial-mesenchymal transition of lens epithelium after injury, Am. J. Pathol., 164(2):651-63 (2004).
Sarmay et al., Mapping and comparison of the interaction sites on the Fc region of IgG responsible for triggering antibody dependent

(56) References Cited

OTHER PUBLICATIONS cellular cytotoxicity (ADCC) through different types of human Fc gamma receptor, Mol. Immunol., 29(5):633-9 (1992).
Schier et al., Isolation of high-affinity monomeric human anti-c-erbB-2 single chain Fv using affinity-driven selection, J. Mol. Biol., 255(1):28-43 (1996).
Schmidt et al., A bivalent single-chain antibody-toxin specific for ErbB-2 and the EGF receptor, Int. J. Cancer, 65(4):538-46 (1996).
Schoonjans et al., Fab chains as an efficient heterodimerization scaffold for the production of recombinant bispecific and trispecific antibody derivatives, J. Immunol., 165(12):7050-7 (2000).
Schuurman et al., The inter-heavy chain disulfide bonds of IgG4 are in equilibrium with intra-chain disulfide bonds, Mol. Immunol., 38(1):1-8 (2001).
Sergeeva et al., Display technologies: application for the discovery of drug and gene delivery agents, Adv. Drug Deliv Rev., 58(15):1622-54 (2006).
Seyedin et al., Purification and characterization of two cartilage-inducing factors from bovine demineralized bone, Proc. Natl. Acad. Sci. USA, 82(8):2267-71 (1986).
Shalaby et al., Development of humanized bispecific antibodies reactive with cytotoxic lymphocytes and tumor cells overexpressing the HER2 protooncogene, J. Exp. Med., 175(1):217-25 (1992).
Shields et al., High resolution mapping of the binding site on human IgG1 for Fc gamma RI, Fc gamma RII, Fc gamma RIII, and FcRn and design of IgG1 variants with improved binding to the Fc gamma R, J. Biol. Chem., 276(9):6591-604 (2001).
Shields et al., Lack of fucose on human IgG1 N-linked oligosaccharide improves binding to human Fcgamma RIII and antibody-dependent cellular toxicity, J. Biol. Chem., 277(30):26733-40 (2002).
Shih et al., A fluorouridine-anti-CEA immunoconjugate is therapeutically effective in a human colonic cancer xenograft model, Int. J. Cancer, 46(6):1101-6 (1990).
Shih et al., Site-specific linkage of methotrexate to monoclonal antibodies using an intermediate carrier, Int. J. Cancer, 41(6):832-9 (1988).
Shinkawa et al., The absence of fucose but not the presence of galactose or bisecting N-acetylglucosamine of human IgG1 complex-type oligosaccharides shows the critical role of enhancing antibody-dependent cellular cytotoxicity, J. Biol. Chem., 278(5):3466-73 (2003).
Shire et al. (eds.), Current Trends in Monoclonal Antibody Development and Manufacturing, Springer/AAPS Press (2010).
Sing et al., Transforming growth factor beta selectively inhibits normal and leukemic human bone marrow cell growth in vitro, Blood, 72(5):1504-11 (1988).
Singer et al., Cutaneous wound healing, N. Engl. J. Med., 341(10):738-46 (1999).
Singh et al., Successful shape-based virtual screening: the discovery of a potent inhibitor of the type I TGFbeta receptor kinase (TbetaRI), Bioorg. Med. Chem. Lett., 13(24):4355-9 (2003).
Sojar et al., A chemical method for the deglycosylation of proteins, Arch. Biochem. Biophys., 259(1):52-7 (1987).
Sporn et al., Transforming growth factor-beta: biological function and chemical structure, Science, 233(4763):532-4 (1986).
Sporn et al., Transforming growth factor-beta: recent progress and new challenges, J. Cell Biol., 119(5):1017-21 (1992).
Steplewski et al., Biological activity of human-mouse IgG1, IgG2, IgG3, and IgG4 chimeric monoclonal antibodies with antitumor specificity, Proc. Natl. Acad. Sci. USA, 85(13):4852-6 (1988).
Stevenson et al., A chimeric antibody with dual Fc regions (bisFabFc) prepared by manipulations at the IgG hinge, Anticancer Drug Des., 3(4):219-30 (1989).
Stinchcomb et al., Isolation and characterisation of a yeast chromosomal replicator, Nature, 282(5734):39-43 (1979).
Studnicka et al., Human-engineered monoclonal antibodies retain full specific binding activity by preserving non-CDR complementarity-modulating residues, Protein Eng., 7(6):805-14 (1994).
Szczepanski et al., Blast-derived microvesicles in sera from patients with acute myeloid leukemia suppress natural killer cell function via membrane-associated transforming growth factor-beta1, Haematologica, 96(9):1302-9 (2011).
Thomas et al., TGF-beta directly targets cytotoxic T cell functions during tumor evasion of immune surveillance, Cancer Cell, 8(5):369-80 (2005).
Thompson et al., An anti-CD3 single-chain immunotoxin with a truncated diphtheria toxin avoids inhibition by pre-existing antibodies in human blood, J. Biol. Chem., 270(47):28037-41 (1995).
Tutt et al., Trispecific F(ab')3 derivatives that use cooperative signaling via the TCR/CD3 complex and CD2 to activate and redirect resting cytotoxic T cells, J. Immunol., 147(1):60-9 (1991).
Umana et al., Engineered glycoforms of an antineuroblastoma IgG1 with optimized antibody-dependent cellular cytotoxic activity, Nat. Biotechnol., 17(2):176-80 (1999).
Vallera et al., Anti-graft-versus-host disease effect of DT390-anti-CD3sFv, a single-chain Fv fusion immunotoxin specifically targeting the CD3 epsilon moiety of the T-cell receptor, Blood, 88(6):2342-53 (1996).
Van Assche et al., Medical therapy for Crohn's disease strictures, Inflamm. Bowel Dis., 10(1):55-60 (2004).
Verhoeyen et al., Reshaping human antibodies: grafting an antilysozyme activity, Science, 239(4847):1534-6 (1988).
Virnekas et al., Trinucleotide phosphoramidites: ideal reagents for the synthesis of mixed oligonucleotides for random mutagenesis, Nucleic Acids Res., 22(25):5600-7 (1994).
Ward et al., Binding activities of a repertoire of single immunoglobulin variable domains secreted from *Escherichia coli*, Nature, 341(6242):544-6 (1989).
Watkins, Screening of phage-expressed antibody libraries by capture lift, Methods Mol. Biol., 178:187-93 (2002).
Wels et al., EGF receptor and p185erbB-2-specific single-chain antibody toxins differ in their cell-killing activity on tumor cells expressing both receptor proteins, Int. J. Cancer, 60(1):137-44 (1995).
Westergren-Thorsson et al., Altered expression of small proteoglycans, collagen, and transforming growth factor-beta 1 in developing bleomycin-induced pulmonary fibrosis in rats, J. Clin. Invest., 92(2):632-7 (1993).
Wheeler et al., Intrabody-based strategies for inhibition of vascular endothelial growth factor receptor-2: effects on apoptosis, cell growth, and angiogenesis, FASEB J., 17(12):1733-5 (2003).
Willems et al., Optimizing expression and purification from cell culture medium of trispecific recombinant antibody derivatives, J. Chromatogr. B Analyt. Technol. Biomed. Life Sci., 786(1-2):161-76 (2003).
William et al., *Fundamental Immunol.*, Ch. 8. 292-5 (1993).
Wilson et al., Bleomycin and IL-1beta-mediated pulmonary fibrosis is IL-17A dependent, J. Exp. Med., 207(3):535-52 (2010).
Winter et al., Making antibodies by phage display technology, Annu. Rev. Immunol., 12:433-55 (1994).
Wittrup, Protein engineering by cell-surface display, Curr. Opin. Biotechnol., 12(4):395-9 (2001).
Wolff et al., Monoclonal antibody homodimers: enhanced antitumor activity in nude mice, Cancer Res., 53(11):2560-5 (1993).
Wrana et al., TGF beta signals through a heteromeric protein kinase receptor complex, Cell, 71(6):1003-14 (1992).
Wrann et al., T cell suppressor factor from human glioblastoma cells is a 12.5-kd protein closely related to transforming growth factor-beta, EMBO J., 6(6):1633-6 (1987).
Xiang et al., Induction of myeloid-derived suppressor cells by tumor exosomes, Int. J. Cancer, 124(11):2621-33 (2009).
Xu et al., Residue at position 331 in the IgG1 and IgG4 CH2 domains contributes to their differential ability to bind and activate complement, J. Biol. Chem., 269(5):3469-74 (1994).
Yamamoto et al., Sustained expression of TGF-beta 1 underlies development of progressive kidney fibrosis, Kidney Int., 45(3):916-27 (1994).
Yamane-Ohnuki et al., Establishment of FUT8 knockout Chinese hamster ovary cells: an ideal host cell line for producing completely defucosylated antibodies with enhanced antibody-dependent cellular cytotoxicity, Biotechnol. Bioeng., 87(5):614-22 (2004).

(56) References Cited

OTHER PUBLICATIONS

Yang et al., A genetically engineered fusion protein M4/TNF with increased bifunctional activity refolded in the presence of protein disulfide isomerase, Hum. Antibodies Hybridomas, 6(4):129-36 (1995).

Yang et al., CDR walking mutagenesis for the affinity maturation of a potent human anti-HIV-1 antibody into the picomolar range, J. Mol. Biol., 254(3):392-403 (1995).

Yang et al., TGF-beta and immune cells: an important regulatory axis in the tumor microenvironment and progression, Trends Immunol., 31(6):220-7 (2010).

Yaniv, Enhancing elements for activation of eukaryotic promoters, Nature, 297(5861):17-8 (1982).

Yu et al., Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells, Int. J. Cancer, 56(2):244-8 (1994).

Zaccolo et al., The effect of high-frequency random mutagenesis on in vitro protein evolution: a study on TEM-1 beta-lactamase, J. Mol. Biol., 285(2):775-83 (1999).

Zapata et al., Engineering linear F(ab')2 fragments for efficient production in *Escherichia coli* and enhanced antiproliferative activity, Protein Eng., 8(10):1057-62 (1995).

Zhao et al., Immune protection function of multipotent mesenchymal stromal cells: role of transforming growth factor-β1. *Cancer Invest.*, 30(9):646-56 (2012).

*$p<0.05$

SEQUENCE LISTING

```
<160> NUMBER OF SEQ ID NOS: 30

<210> SEQ ID NO 1
<211> LENGTH: 366
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Clone XPA.42.068 heavy chain

<400> SEQUENCE: 1
caggttcagc tggtgcagtc tggggctgag gtgaagaagc ctggggcctc agtgaaggtc        60
tcctgcaagg cttctggata caccttcacc ggctactata tgcactgggt gcgacaggcc       120
cctggacaag ggcttgagtg gatgggatgg atcaacccta cactggtgg cacaaactat       180 gcacagaagt tcagggcag ggtcaccatg accagggaca cgtccatcag cacagcctac       240
atggagctga gcaggctgag atctgacgac acggccgttt attactgtgc gagatcattc       300
ctgtggctgg ttccctctga tgcttttgat atctggggcc aagggacaat ggtcaccgtc       360
tcttca                                                                  366

<210> SEQ ID NO 2
<211> LENGTH: 122
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 heavy chain
<220> FEATURE:
<221> NAME/KEY: MISC_FEATURE
<222> LOCATION: (26)..(33)
<223> OTHER INFORMATION: H-CDR1
```

```
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(111)
<223> OTHER INFORMATION: H-CDR3

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Thr Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Phe Leu Trp Leu Val Pro Ser Asp Ala Phe Asp Ile Trp
            100                 105                 110

Gly Gln Gly Thr Met Val Thr Val Ser Ser
        115                 120

<210> SEQ ID NO 3
<211> LENGTH: 327
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Clone XPA.42.068 light chain

<400> SEQUENCE: 3
tcttctgagc tgactcagcc accctcagtg tccgtggccc caggagagaa ggccaggatt      60
acctgtgggg ggaataacat tggacgtaaa agtgtacatt ggtaccagca gaggccaggc     120
caggcccctg ttgtggtcct ctactatgat agagtcagac cctcagggat ccctgagcga     180
ttttctggct ccaactctgg gaacacggcc accctgacca tcaccagggt cgaagccggg     240
gatgaggccg actattttg tcaggtgtgg gataacacta gtgagcatgt ggtcttcggc      300
ggaggcaccc agctgaccgt cctaggc                                          327

<210> SEQ ID NO 4
<211> LENGTH: 109
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 light chain
<220> FEATURE:
<221> NAME/KEY: MISC_FEATURE
<222> LOCATION: (26)..(31)
<223> OTHER INFORMATION: L-CDR1
<220> FEATURE:
<221> NAME/KEY: MISC_FEATURE
<222> LOCATION: (49)..(51)
<223> OTHER INFORMATION: L-CDR2
<220> FEATURE:
```

<221> NAME/KEY: MISC_FEATURE
<222> LOCATION: (88)..(97)
<223> OTHER INFORMATION: L-CDR3

<400> SEQUENCE: 4

Ser Ser Glu Leu Thr Gln Pro Pro Ser Val Ser Val Ala Pro Gly Glu
1               5                   10                  15

Lys Ala Arg Ile Thr Cys Gly Gly Asn Asn Ile Gly Arg Lys Ser Val
            20                  25                  30

His Trp Tyr Gln Gln Arg Pro Gly Gln Ala Pro Val Val Leu Tyr
        35                  40                  45

Tyr Asp Arg Val Arg Pro Ser Gly Ile Pro Glu Arg Phe Ser Gly Ser
    50                  55                  60

Asn Ser Gly Asn Thr Ala Thr Leu Thr Ile Thr Arg Val Glu Ala Gly
65              70                  75                  80

Asp Glu Ala Asp Tyr Phe Cys Gln Val Trp Asp Asn Ser Glu His
                85                  90                  95

Val Val Phe Gly Gly Gly Thr Gln Leu Thr Val Leu Gly
            100                 105

<210> SEQ ID NO 5
<211> LENGTH: 363
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Clone XPA.42.089 heavy chain

<400> SEQUENCE: 5
caggtgcagc tggtacagtc tggggctgag gtgaagaagc ctgggtcctc ggtgaaggtc       60
tcctgcaagg cttctggagg caccttcagc agctatgcta tcagctgggt gcgacaggcc      120
cctggacaag gcttgagtg gatgggaggg atcatcccta tctttggtac agcaaactac       180
gcacagaagt tccagggcag agtcacgatt accgcggacg aatccacgag cacagcctac      240
atggagctga gcagcctgag atctgaggac acggccgtgt attactgtgc gaggggacta      300
tgggaggttc gggcccttcc gtcggtctac tggggccagg gaaccctggt caccgtctcc      360
tca                                                                    363

<210> SEQ ID NO 6
<211> LENGTH: 121
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(110)
<223> OTHER INFORMATION: H-CDR3

<400> SEQUENCE: 6

```
Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Trp Glu Val Arg Ala Leu Pro Ser Val Tyr Trp Gly
            100                 105                 110

Gln Gly Thr Leu Val Thr Val Ser Ser
        115                 120
```

<210> SEQ ID NO 7
<211> LENGTH: 327
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Clone XPA.42.089 light chain

<400> SEQUENCE: 7

```
tcctatgagc tgacacagcc accctcagtg tccgtggccc cgggacagac ggccagaatt    60
acctgtgggg caaatgacat tggaagtaaa agtgtccact ggtaccagca gaaggcaggc   120
caggcccctg tactggtcgt ctctgaagat atcatccggc cctcagggat ccctgagcga   180
atctctggct ccaactctgg gaacacggcc accctgacca tcagcagggt cgaagccggg   240
gatgaggccg actattactg tcaagtttgg gataggata gtgatcaata tgtctttgga   300
actgggacca aggtcaccgt cctaggc                                       327
```

<210> SEQ ID NO 8
<211> LENGTH: 109
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 light chain
<220> FEATURE:
<221> NAME/KEY: MISC_FEATURE
<222> LOCATION: (26)..(31)
<223> OTHER INFORMATION: L-CDR1
<220> FEATURE:
<221> NAME/KEY: MISC_FEATURE
<222> LOCATION: (49)..(51)
<223> OTHER INFORMATION: L-CDR2
<220> FEATURE:
<221> NAME/KEY: MISC_FEATURE
<222> LOCATION: (88)..(97)
<223> OTHER INFORMATION: L-CDR3

<400> SEQUENCE: 8

```
Ser Tyr Glu Leu Thr Gln Pro Pro Ser Val Ser Val Ala Pro Gly Gln
1               5                   10                  15

Thr Ala Arg Ile Thr Cys Gly Ala Asn Asp Ile Gly Ser Lys Ser Val
            20                  25                  30
```

His Trp Tyr Gln Gln Lys Ala Gly Gln Ala Pro Val Leu Val Ser
        35                  40                  45

Glu Asp Ile Ile Arg Pro Ser Gly Ile Pro Glu Arg Ile Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Arg Asp Ser Asp Gln
                 85                  90                  95

Tyr Val Phe Gly Thr Gly Thr Lys Val Thr Val Leu Gly
            100                 105

<210> SEQ ID NO 9
<211> LENGTH: 366
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Clone XPA.42.681 heavy chain

<400> SEQUENCE: 9
caggttcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag ggcttgagtg gatgggatgg atcaaccctaa acactggtgg cacaaactat     180
gcacagaagt ttcagggcag ggtcaccatg accagggaca cgtccatcag cacagcctac     240
atggagctga gcaggctgag atctgacgac acggccgttt attactgtgc gagatcattc     300
ctgtggctgg ttccctctga tgcttttgat atctggggcc aagggacaat ggtcaccgtc     360
tcttca                                                                 366

<210> SEQ ID NO 10
<211> LENGTH: 122
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.681 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(111)
<223> OTHER INFORMATION: H-CDR3

<400> SEQUENCE: 10

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Trp Ile Asn Pro Asn Thr Gly Gly Thr Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Phe Leu Trp Leu Val Pro Ser Asp Ala Phe Asp Ile Trp
            100                 105                 110

Gly Gln Gly Thr Met Val Thr Val Ser Ser
        115                 120

<210> SEQ ID NO 11
<211> LENGTH: 327
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Clone XPA.42.681 light chain

<400> SEQUENCE: 11
tcctatgtgc tgactcagcc accctcagtg tccgtggccc caggaaagac ggccaggatt    60
acctgtgggg gaaacaacat tggatttaga agtgtgcact ggtaccaaca gaagtcaggc   120
caggcccctg tcctggtcat ctatttgat cgcgcccggc cctcagggat ccctgagcga    180
ttctctgcct ccaactctga gaacacggcc accctgacca tcaggagggt cgaagccggg   240
gatgaggccg actattactg tcaggtgtgg gatagtgaca gtgatgatct agtcttcggc   300
ggaggcaccc agctgaccgt cctaggt                                       327

<210> SEQ ID NO 12
<211> LENGTH: 109
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.681 light chain
<220> FEATURE:
<221> NAME/KEY: MISC_FEATURE
<222> LOCATION: (26)..(31)
<223> OTHER INFORMATION: L-CDR1
<220> FEATURE:
<221> NAME/KEY: MISC_FEATURE
<222> LOCATION: (49)..(51)
<223> OTHER INFORMATION: L-CDR2
<220> FEATURE:
<221> NAME/KEY: MISC_FEATURE
<222> LOCATION: (88)..(98)
<223> OTHER INFORMATION: L-CDR3

<400> SEQUENCE: 12

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Phe Arg Ser Val
            20                  25                  30

His Trp Tyr Gln Gln Lys Ser Gly Gln Ala Pro Val Leu Val Ile Tyr
        35                  40                  45

Phe Asp Arg Ala Arg Pro Ser Gly Ile Pro Glu Arg Phe Ser Ala Ser
    50                  55                  60

Asn Ser Glu Asn Thr Ala Thr Leu Thr Ile Arg Arg Val Glu Ala Gly
65                  70                  75                  80

Asp Glu Ala Asp Tyr Tyr Cys Gln Val Trp Asp Ser Asp Ser Asp Asp

```
                    85                  90                  95

Leu Val Phe Gly Gly Gly Thr Gln Leu Thr Val Leu Gly
            100                 105

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 - H-CDR1

<400> SEQUENCE: 13

Gly Tyr Thr Phe Thr Gly Tyr Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 - H-CDR2

<400> SEQUENCE: 14

Ile Asn Pro Asn Thr Gly Gly Thr
1               5

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 - H-CDR3

<400> SEQUENCE: 15

Ala Arg Ser Phe Leu Trp Leu Val Pro Ser Asp Ala Phe Asp Ile
1               5                   10                  15

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 - L-CDR1

<400> SEQUENCE: 16

Asn Ile Gly Arg Lys Ser
1               5

<210> SEQ ID NO 17
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 - L-CDR2
```

```
<400> SEQUENCE: 17

Tyr Asp Arg
1

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 - L-CDR3

<400> SEQUENCE: 18

Gln Val Trp Asp Asn Thr Ser Glu His Val
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 - H-CDR1

<400> SEQUENCE: 19

Gly Gly Thr Phe Ser Ser Tyr Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 - H-CDR2

<400> SEQUENCE: 20

Ile Ile Pro Ile Phe Gly Thr Ala
1               5

<210> SEQ ID NO 21
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 - H-CDR3

<400> SEQUENCE: 21

Ala Arg Gly Leu Trp Glu Val Arg Ala Leu Pro Ser Val Tyr
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<223> OTHER INFORMATION: Clone XPA.42.089 - L-CDR1

<400> SEQUENCE: 22

Asp Ile Gly Ser Lys Ser
1               5

<210> SEQ ID NO 23
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 - L-CDR2

<400> SEQUENCE: 23

Glu Asp Ile
1

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 - L-CDR3

<400> SEQUENCE: 24

Gln Val Trp Asp Arg Asp Ser Asp Gln Tyr
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42-681 - H-CDR1

<400> SEQUENCE: 25

Gly Tyr Thr Phe Thr Gly Tyr Tyr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42-681 - H-CDR2

<400> SEQUENCE: 26

Ile Asn Pro Asn Thr Gly Gly Thr
1               5

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<223> OTHER INFORMATION: Clone XPA.42-681 - H-CDR3

<400> SEQUENCE: 27

Ala Arg Ser Phe Leu Trp Leu Val Pro Ser Asp Ala Phe Asp Ile
1               5                   10                  15

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42-681 - L-CDR1

<400> SEQUENCE: 28

Asn Ile Gly Phe Arg Ser
1               5

<210> SEQ ID NO 29
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42-681 - L-CDR2

<400> SEQUENCE: 29

Phe Asp Arg
1

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42-681 - L-CDR3

<400> SEQUENCE: 30

Gln Val Trp Asp Ser Asp Ser Asp Asp Leu Val
1               5                   10
```

TGF-BETA-SPECIFIC ANTIBODIES AND METHODS OF USE THEREOF FOR TREATMENT

CROSS REFERENCE TO RELATED APPLICATIONS

This is application is a continuation of U.S. patent application Ser. No. 14/038,436, filed Sep. 26, 2013, now U.S. Pat. No. 9,145,458, issued Sep. 29, 2015, which is a continuation of U.S. patent application Ser. No. 13/486,983, filed Jun. 1, 2012, now U.S. Pat. No. 8,569,462, issued Oct. 29, 2013, which claims the priority benefit of U.S. Provisional Patent Application No. 61/493,230, filed Jun. 3, 2011, herein incorporated by reference.

FIELD OF THE INVENTION

The present disclosure relates, in general, to materials and methods for antibodies specific for transforming growth factor beta (TGFβ), including TGFβ1, TGFβ2 and/or TGFβ3, and uses of these antibodies in the treatment of subjects having cancer, an eye disease, condition or disorder, fibrosis, including fibrosis of the eye or ophthalmic fibroses, and other conditions or disorders related to TGFβ expression.

BACKGROUND

The transforming growth factor beta (TGFβ) protein family consists of three distinct isoforms found in mammals (TGFβ1, TGFβ2, and TGFβ3). The TGFβ proteins activate and regulate multiple gene responses that influence disease states, including cell proliferative, inflammatory, and cardiovascular conditions. TGFβ is a multifunctional cytokine originally named for its ability to transform normal fibroblasts to cells capable of anchorage-independent growth. The TGFβ molecules are produced primarily by hematopoietic and tumor cells and can regulate, i.e., stimulate or inhibit, the growth and differentiation of cells from a variety of both normal and neoplastic tissue origins (Sporn et al., Science, 233: 532 (1986)), and stimulate the formation and expansion of various stromal cells.

The TGFβs are known to be involved in many proliferative and non-proliferative cellular processes such as cell proliferation and differentiation, embryonic development, extracellular matrix formation, bone development, wound healing, hematopoiesis, and immune and inflammatory responses. See e.g., Pircher et al, Biochem. Biophys. Res. Commun., 136: 30-37 (1986); Wakefield et al., Growth Factors, 1: 203-218 (1989); Roberts and Sporn, pp 419-472 in Handbook of Experimental Pharmacology eds M. B. Sporn & A. B. Roberts (Springer, Heidelberg, 1990); Massague et al., Annual Rev. Cell Biol., 6: 597-646 (1990); Singer and Clark, New Eng. J. Med., 341: 738-745 (1999). Also, TGFβ is used in the treatment and prevention of diseases of the intestinal mucosa (WO 2001/24813). TGFβ is also known to have strong immunosuppressuve effects on various immunologic cell types, including cytotoxic T lymphocyte (CTL) inhibition (Ranges et al., J. Exp. Med., 166: 991, 1987), Espevik et al., J. Immunol., 140: 2312, 1988), depressed B cell lymphopoiesis and kappa light-chain expression (Lee et al., J. Exp. Med., 166: 1290, 1987), negative regulation of hematopoiesis (Sing et al., Blood, 72: 1504, 1988), down-regulation of HLA-DR expression on tumor cells (Czarniecki et al., J. Immunol., 140: 4217, 1988), and inhibition of the proliferation of antigen-activated B lymphocytes in response to B-cell growth factor (Petit-Koskas et al., Eur. J. Immunol., 18: 111, 1988). See also U.S. Pat. No. 7,527,791.

Antibodies to TGFβ have been described in U.S. Pat. Nos. 7,527,791; 7,927,593; 7,494,651; 7,369,111; 7,151,169; 6,492,497; 6,419,928; 6,090,383; 5,783,185; 5,772,998; 5,571,714; and 7,723,486.

SUMMARY OF THE INVENTION

The present disclosure provides methods and compositions for the treatment of disease or disorders associated with TGFβ expression. The disclosure provides antibodies that bind TGFβ1, TGFβ2 and TGFβ3. It is provided that the antibodies described herein can have differential affinity for any or all of the TGFβ isoforms. Further, it was discovered herein that the disclosed TGFβ-specific antibodies unexpectedly modulate immune cells in tumors (e.g., infiltrate into tumors) and are contemplated for treatment of tumors associated with TGFβ expression, as well as other conditions or disorders associated with TGFβ expression.

In one aspect, the disclosure provides an antibody that binds transforming growth factor beta (TGFβ)1, TGFβ2 and TGFβ3 comprising: (a) a heavy chain complementary determining repeat (CDR)1 amino acid sequence set forth in Table 1 or SEQ ID NOs: 13, 19 and 25, or a variant thereof in which one or two amino acids have been changed; (b) a heavy chain CDR2 amino acid sequence set forth in Table 1 or SEQ ID NOs: 14, 20 and 26 that is from the same heavy chain variable region as (a), or a variant thereof in which one or two amino acids have been changed; and (c) a heavy chain CDR3 amino acid sequence set forth in Table 1 or SEQ ID NOs: 15, 21 and 27 that is from the same heavy chain variable region as (a), or a variant thereof in which one or two amino acids have been changed.

In a related aspect, the disclosure provides an antibody that binds transforming growth factor beta (TGFβ)1, TGFβ2 and TGFβ3 comprising: (a) a heavy chain CDR1 amino acid sequence set forth in Table 1 or SEQ ID NOs: 13, 19 and 25, or a variant thereof having at least 70% identity thereto; (b) a heavy chain CDR2 amino acid sequence set forth in Table 1 or SEQ ID NOs: 14, 20 and 26 that is from the same heavy chain variable region as (a), or a variant thereof having at least 70% identity thereto; and (c) a heavy chain CDR3 amino acid sequence set forth in Table 1 or SEQ ID NOs: 15, 21 and 27 that is from the same heavy chain variable region as (a), or a variant thereof having at least 70% identity thereto.

In a further aspect, the disclosure contemplates an antibody that binds transforming growth factor beta (TGFβ)1, TGFβ2 and TGFβ3 comprising: (a) a heavy chain CDR1 amino acid sequence set forth in Table 1 or SEQ ID NOs: 13, 19 and 25, or a variant thereof having at least 70% identity thereto; (b) an independently selected heavy chain CDR2 amino acid sequence set forth in Table 1 or SEQ ID NOs: 14, 20 and 26, or a variant thereof having at least 70% identity thereto; and (c) an independently selected heavy chain CDR3 amino acid sequence set forth in Table 1 or SEQ ID NOs: 15, 21 and 27, or a variant thereof having at least 70% identity thereto.

In certain embodiments, at least two of the heavy chain CDR1, CDR2 or CDR3 amino acid sequences are set forth in Table 1 or SEQ ID NOs: 13-15, 19-21 and 25-27. In a related embodiment, three of the heavy chain CDR1, CDR2 and CDR3 amino acid sequences are set forth in Table 1 or SEQ ID NOs: 13-15, 19-21 and 25-27.

In some embodiments, it is contemplated that the antibody comprises an amino acid sequence at least 85% identical to a heavy chain variable region amino acid sequence set forth in Table 1 or SEQ ID NOs: 2, 6 and 10. In a related embodiment, the antibody comprises an amino acid sequence at least 95% identical to a heavy chain variable region amino acid sequence set forth in Table 1 or SEQ ID NOs: 2, 6 and 10.

In still other embodiments, the antibody comprises a polypeptide sequence having an amino acid sequence at least 70% identical over all three HCDRs in a heavy chain variable region, the amino acid sequences of HCDR1, HCDR2 and HCDR3 set forth in SEQ ID NOs: 13-15, 19-21 and 25-27.

In certain embodiments, one or more heavy chain framework amino acids have been replaced with corresponding amino acid(s) from another human antibody amino acid sequence.

It is contemplated that an antibody described herein further comprises any one of the light chain CDR amino acid sequences set forth in Table 1 or SEQ ID NOs: 16-18, 22-24 and 28-30. In some embodiments, an antibody comprises at least two of the light chain CDR amino acid sequences set forth in Table 1 or SEQ ID NOs: 16-18, 22-24 and 28-30. In other embodiments, an antibody comprises at least three of the light chain CDR amino acid sequences set forth in Table 1 or SEQ ID NOs: 16-18, 22-24 and 28-30.

In another aspect, an antibody described herein comprises (a) a light chain CDR1 amino acid sequence set forth in Table 1 or SEQ ID NOs: 16, 22 and 28, or a variant thereof in which one or two amino acids have been changed; (b) a light chain CDR2 amino acid sequence set forth in Table 1 or SEQ ID NOs: 17, 23 and 29 that is from the same light chain variable region as (a), or a variant thereof in which one or two amino acids have been changed; and (c) a light chain CDR3 amino acid sequence set forth in Table 1 or SEQ ID NOs: 18, 24 and 30 that is from the same light chain variable region as (a), or a variant thereof in which one or two amino acids have been changed.

In alternative embodiments, an antibody contemplated herein comprises: (a) a light chain CDR1 amino acid sequence set forth in Table 1 or SEQ ID NOs: 16, 22 and 28, or a variant thereof in which one or two amino acids have been changed; (b) an independently selected light chain CDR2 amino acid sequence set forth in Table 1 or SEQ ID NOs: 17, 23 and 29, or a variant thereof in which one or two amino acids have been changed; and (c) an independently selected light chain CDR3 amino acid sequence set forth in Table 1 or SEQ ID NOs: 18, 24 and 30, or a variant thereof in which one or two amino acids have been changed.

In certain embodiments, at least two of the light chain CDR1, CDR2 or CDR3 amino acid sequences are set forth in Table 1 or SEQ ID NOs: 16-18, 22-24 and 28-30.

It is further contemplated that an antibody described herein comprises a polypeptide sequence having an amino acid sequence at least 70% identical over all three LCDRs of a light chain variable region, the amino acid sequences of LCDR1, LCDR2 and LCDR3 set forth in SEQ ID NOs: 16-18, 22-24 and 28-30.

In one embodiment, an antibody contemplated herein comprises an amino acid sequence at least 70% identical to a light chain variable region amino acid sequence set forth in Table 1 or SEQ ID NOs: 4, 8 and 12. In a related embodiment, the antibody comprises an amino acid sequence at least 85% identical to a light chain variable region amino acid sequence set forth in Table 1 or SEQ ID NOs: 4, 8 and 12. In a further embodiment, the antibody comprises an amino acid sequence at least 95% identical to a light chain variable region amino acid sequence set forth in Table 1 or SEQ ID NOs: 4, 8 and 12. In still another embodiment, the antibody comprises a light chain variable region amino acid sequence set forth in Table 1 or SEQ ID NOs: 4, 8 and 12.

In a further embodiment, an antibody described herein comprises (i) an amino acid sequence at least 70% identical over all three LCDRs, of a light chain variable region, the amino acid sequences of LCDR1, LCDR2 and LCDR3 set forth in SEQ ID NOs: 16-18, 22-24 and 28-30 and (ii) an amino acid sequence at least 70% identical over all three HCDRs of a heavy chain variable region, the amino acid sequences of HCDR1, HCDR2 and HCDR3 set forth in SEQ ID NOs: 13-15, 19-21 and 25-27.

In another aspect, the disclosure provides an antibody that binds transforming growth factor beta (TGFβ)1, TGFβ2 and TGFβ3 comprising a light chain variable region and/or a heavy chain variable region, wherein (a) the light chain variable region comprises at least a CDR1 selected from SEQ ID NOs: 16, 22 and 28 or sequences at least 80% identical thereto, a CDR2 selected from SEQ ID NOs: 17, 23 and 29 or sequences at least 80% identical thereto, and/or a CDR3 selected from SEQ ID NOs: 18, 24 and 30 or sequences at least 80% identical thereto; and/or wherein (b) the heavy chain variable region comprises at least a CDR1 selected from SEQ ID NOs: 13, 19 and 25 or sequences at least 80% identical thereto, a CDR2 selected from SEQ ID NOs: 14, 20 and 26 or sequences at least 80% identical thereto, and/or a CDR3 selected from SEQ ID NOs: 15, 21 and 27 or sequences at least 80% identical thereto. In one embodiment, the light chain variable region comprises at least a CDR1 selected from SEQ ID NO: 16 or sequences at least 90% identical thereto, a CDR2 selected from SEQ ID NO: 17 or sequences at least 90% identical thereto, and a CDR3 selected from SEQ ID NO: 18 or sequences at least 90% identical thereto; and/or the heavy chain variable region comprises at least a CDR1 selected from SEQ ID NO: 13 or sequences at least 90% identical thereto, a CDR2 selected from SEQ ID NO: 14 or sequences at least 90% identical thereto, and a CDR3 selected from SEQ ID NO: 15 or sequences at least 90% identical thereto.

In a related embodiment, the light chain variable region comprises at least a CDR1 selected from SEQ ID NO: 22 or sequences at least 90% identical thereto, a CDR2 selected from SEQ ID NO: 23 or sequences at least 90% identical thereto, and a CDR3 selected from SEQ ID NO: 24 or sequences at least 90% identical thereto; and/or the heavy chain variable region comprises at least a CDR1 selected from SEQ ID NO: 19 or sequences at least 90% identical thereto, a CDR2 selected from SEQ ID NO: 20 or sequences at least 90% identical thereto, and a CDR3 selected from SEQ ID NO: 21 or sequences at least 90% identical thereto.

In certain embodiments, the light chain variable region comprises at least a CDR1 selected from SEQ ID NO: 28 or sequences at least 90% identical thereto, a CDR2 selected from SEQ ID NO: 29 or sequences at least 90% identical thereto, and a CDR3 selected from SEQ ID NO: 30 or sequences at least 90% identical thereto; and/or the heavy chain variable region comprises at least a CDR1 selected from SEQ ID NO: 25 or sequences at least 90% identical thereto, a CDR2 selected from SEQ ID NO: 26 or sequences at least 90% identical thereto, and a CDR3 selected from SEQ ID NO: 27 or sequences at least 90% identical thereto.

It is contemplated that the percent identity of any one of the above antibody sequences can be at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to a heavy or light chain variable region or any of HCDR1, HCDR2, HCDR3, LCDR1, LCDR2 or LCDR3 disclosed herein.

In some embodiments, an antibody of the disclosure further comprises a heavy chain constant region, wherein the heavy chain constant region is a modified or unmodified IgG, IgM, IgA, IgD, IgE, a fragment thereof, or combinations thereof.

In certain embodiments, an antibody is provided in which one or more light chain framework amino acids have been replaced with corresponding amino acid(s) from another human antibody amino acid sequence.

In one aspect, the antibody of the disclosure is selected from the group consisting of XPA.42.089, XPA.42.068 and XPA.42.681. Heavy and light chain amino acid sequences of XPA.42.089 are set out in SEQ ID NOs: 6 and 8, respectively. Heavy and light chain amino acid sequences of XPA.42.068 are set out in SEQ ID NOs: 2 and 4, respectively, and heavy and light chain amino acid sequences of XPA.42.681 are set out in SEQ ID NOs: 10 and 12, respectively.

In one embodiment, an antibody described herein further comprises a human light chain constant region attached to said light chain variable region. In some embodiments, the light chain constant region is a modified or unmodified lambda light chain constant region, a kappa light chain constant region, a fragment thereof, or combinations thereof.

In a preferred embodiment, the disclosure provides an antibody specific for TGFβ1, TGFβ2 and TGFβ3 with an affinity Kd of $10^{-6}$ M or less. In exemplary embodiments, an anti-TGFβ antibody described herein binds at least one isoform of TGFβ with an affinity of $10^{-6}$ M, $10^{-7}$ M, $10^{-8}$ M, $10^{-9}$ M or less, or optionally binds two TGFβ isoforms, or all of TGFβ1, 2, or 3 with an affinity of $10^{-6}$ M, $10^{-7}$ M, $10^{-8}$ M, $10^{-9}$ M, $10^{-10}$ M, $10^{-11}$ M, or $10^{-12}$ M or less for one or more of the isoforms. In other embodiments, an antibody described herein binds to TGFβ1 and TGFβ2 with at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% higher affinity (e.g., preferentially binds to TGFβ1 and TGFβ2) compared to binding to TGFβ3. Alternatively, an antibody described herein, binds each of TGFβ isoforms TGFβ1, TGFβ2 and TGFβ3 with an affinity within 3-fold, 5-fold or 10-fold of each other. In certain embodiments, the antibody binds to TGFβ1 and TGFβ2 with greater affinity than TGFβ3. In certain embodiments, the affinity is measured by surface plasmon resonance or KINEXA assay.

In some embodiments, the antibody neutralizes activity of TGFβ1 and TGFβ2 to a greater extent than TGFβ3. In some embodiments, antibody neutralization of TGFβ1 and TGFβ2 is at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% more potent that neutralization of TGFβ3. Exemplary neutralization assays contemplated herein include, but are not limited to, an interleukin-11 release assay and an HT-2 cell proliferation assay. In addition, a TGFβ activity assay can be carried out to determine if an antibody disclosed herein inhibits one TGFβ isoform preferentially, including a pSMAD phosphorylation assay or an rhLAP binding assay. In a further embodiment, the antibody has a lower IC50 (i.e., better binding, greater potency) for TGFβ1 and TGFβ2 compared to TGFβ3.

In another aspect, the disclosure provides an isolated nucleic acid molecule comprising a nucleotide sequence that encodes the heavy chain and/or light chain as described herein.

In a further aspect, the disclosure provides an expression vector comprising a nucleic acid molecule contemplated herein operably linked to an expression control sequence. Also contemplated is a host cell comprising an expression vector or a nucleic acid molecule of the disclosure. In certain embodiments, the disclosure provides a host cell comprising a nucleic acid molecule encoding a heavy chain and a light chain variable region, wherein the heavy chain and light chain nucleic acids are expressed by different nucleic acids or on the same nucleic acid.

In a related aspect, the disclosure provides a method of using the host cell as described herein to produce an antibody, the method comprising culturing the host cell under suitable conditions and recovering said antibody. Also provided is an antibody produced by the method disclosed herein.

The disclosure further contemplates a sterile pharmaceutical composition comprising the antibody as disclosed herein and a pharmaceutically acceptable carrier.

In another aspect, the disclosure provides a method for treating a disease, condition or disorder associated with TGFβ expression comprising the step of administering to a subject in need thereof a therapeutically effective amount of an antibody or a pharmaceutical composition contemplated herein. In certain embodiments, the disease, condition or disorder is selected from the group consisting of a cancer, an eye (e.g., ocular, optic, ophthalmic or ophthalmological) disease, condition or disorder, a disease condition or disorder associated with fibrosis, e.g., fibroproliferative diseases, conditions or disorders, or disease, conditions or disorders having an associated fibrosis.

Fibroproliferative diseases, conditions or disorders or diseases having an associated fibrosis include those that affect any organ or tissue in the body, including, but not limited to the skin, lung, kidney, heart, brain and eye. Fibroproliferative diseases, conditions or disorders or diseases having an associated fibrosis include, but are not limited to pulmonary fibrosis, idiopathic pulmonary fibrosis, peribronchiolar fibrosis, interstitial lung disease, chronic obstructive pulmonary disease (COPD), small airway disease (e.g., obstructive bronchiolitis), emphysema, adult or acute respiratory distress syndrome (ARDS), acute lung injury (ALI), pulmonary fibrosis due to infectious or toxic agents, kidney fibrosis, glomerulonephritis (GN) of all etiologies, mesangial proliferative GN, immune GN, crescentic GN, glomerulosclerosis, tubulointerstitial injury, renal interstitial fibrosis, renal fibrosis and all causes of renal interstitial fibrosis, renal fibrosis resulting from complications of drug exposure, including cyclosporin treatment of transplant recipients, HIV-associated nephropathy, transplant necropathy, diabetic kidney disease, diabetic nephropathy, nephrogenic systemic fibrosis, diabetes, idiopathic retroperitoneal fibrosis, scleroderma, liver fibrosis, hepatic diseases associated with excessive scarring and progressive sclerosis, liver cirrhosis due to all etiologies, disorders of the biliary tree, hepatic dysfunction attributable to infections, fibrocystic diseases, cardiovascular diseases, congestive heart failure, dilated cardiomyopathy, myocarditis, vascular stenosis cardiac fibrosis, post-infarction cardiac fibrosis, post myocardial infarction, left ventricular hypertrophy, veno-occlusive disease, restenosis, post-angioplasty restenosis, arteriovenous graft failure, atherosclerosis, hypertension, hypertensive heart disease, cardiac hypertrophy, hypertrophic cardiomyopathy, heart failure, disease of the aorta, progressive systemic sclerosis; polymyositis; systemic lupus erythematosus; dermatomyositis, fascists, Raynaud's syndrome, rheumatoid arthritis, proliferative vitreoretinopathy, vitreoretinopathy of any etiology, fibrosis associated with ocular surgery, treatment of glaucoma, retinal reattachment, cataract extraction, or drainage procedures of any kind, scarring in the cornea and conjunctiva, fibrosis in the corneal endothelium, alkali burn, (e.g., alkali burn to the cornea) post-cataract surgery fibrosis of the lens capsule, excess scarring in the tissue around the extraocular muscles in the strabismus surgery, anterior subcapsular cataract and posterior capsule opacification, anterior segment fibrotic diseases of the eye, fibrosis of the corneal stroma, fibrosis associated with corneal opacification, fibrosis of the trabecular network, fibrosis associated with glaucoma, posterior segment fibrotic diseases of the eye, fibrovascular scarring, fibrosis in retinal or choroidal vasculature of the eye, retinal fibrosis, epiretinal fibrosis, retinal gliosis, subretinal fibrosis, fibrosis associated with age related macular degeneration, post-retinal and glaucoma surgery, tractional retinal detachment in association with contraction of the tissue in diabetic retinopathy, Peyronie's disease, systemic sclerosis, post-spinal cord injury, osteoporosis, Camurati-Engelmann disease, Crohn's disease, scarring, Marfan syndrome, premature ovarian failure, Alzheimer's Disease, Parkinson's Disease, fibrosis due to surgical incisions or mechanical trauma, fibrosis associated with ocular surgery, and excessive or hypertrophic scar or keloid formation in the dermis occurring during wound healing resulting from trauma or surgical wounds.

Exemplary eye diseases (e.g., ocular, optic, ophthalmic or ophthalmological diseases), conditions or disorders, include but are not limited to, fibroproliferative disorders, fibrosis of the eye, ophthalmic fibroses, retinal dysfunction, fibrosis associated with retinal dysfunction, wet or dry macular degeneration, proliferative vitreoretinopathy, vitreoretinopathy of any etiology, fibrosis associated with ocular surgery such as treatment of glaucoma, retinal reattachment, cataract extraction, or drainage procedures of any kind, scarring in the cornea and conjunctiva, fibrosis in the corneal endothelium, alkali burn (e.g., alkali burn to the cornea), post-cataract surgery fibrosis of the lens capsule, excess scarring in the tissue around the extraocular muscles in the strabismus surgery, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), fibrosis associated with post-retinal and glaucoma surgery, tractional retinal detachment in association with contraction of the tissue in diabetic retinopathy.

Exemplary fibroproliferative disease, condition, or disorders of the eye, fibrosis of the eye, ocular fibrosis or ophthalmic fibroses include, but are not limited to, proliferative vitreoretinopathy, vitreoretinopathy of any etiology, fibrosis associated with retinal dysfunction, fibrosis associated with wet or dry macular degeneration, fibrosis associated with ocular surgery such as treatment of glaucoma, retinal reattachment, cataract extraction, or drainage procedures of any kind, scarring in the cornea and conjunctiva, fibrosis in the corneal endothelium, fibrosis associated with alkali burn, post-cataract surgery fibrosis of the lens capsule, excess scarring the tissue around the extraocular muscles in the strabismus surgery, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), fibrosis associated with post-retinal and glaucoma surgery, tractional retinal detachment in association with contraction of the tissue in diabetic retinopathy.

In various embodiments, the fibroproliferative disease, condition, or disorders of the eye is selected from the group consisting of proliferative vitreoretinopathy, fibrosis associated with ocular surgery, post-cataract surgery fibrosis of the lens, fibrosis of the corneal stroma and alkali burn.

In a related aspect, the disclosure provides a method for treating cancer comprising administering to a subject in need thereof a therapeutically effective amount of an antibody or a pharmaceutical composition contemplated herein. In certain embodiments, the cancer is selected from the group consisting of lung cancer, prostate cancer, breast cancer, hepatocellular cancer, esophageal cancer, colorectal cancer, pancreatic cancer, bladder cancer, kidney cancer, ovarian cancer, stomach cancer, fibrotic cancer, glioma and melanoma.

In some embodiments, the antibody or composition increases the number of natural killer (NK) cells in a tumor. In various embodiments, the antibody or composition increases cytolytic activity of NK cells. For example, in various embodiments, the antibody or composition described herein increases perforin and granzyme production by NK cells. In one embodiment, the antibody is XPA.42.089 or XPA.42.681.

In various embodiments, the antibody or composition described herein decreases the number of regulatory T cells in a tumor and/or inhibits regulatory T cell function. For example, in various embodiments, the antibody or composition described herein inhibits inhibits the ability of Tregs to down-regulate an immune response or to migrate to a site of an immune response.

In various embodiments, the antibody or composition increases the number of cytotoxic T cells in a tumor and/or enhances CTL activity, e.g., boosts, increases or promotes CTL activity. For example, in various embodiments, the antibody or composition described herein increases perforin and granzyme production by CTL and increases cytolytic activity of the CTL. In one embodiment, the antibody is XPA.42.068, XPA.42.089 or XPA.42.681.

In another embodiment, the antibody or composition decreases the number of monocyte-derived stem cells (MDSC) in a tumor and/or inhibits MDSC function. For example, in various embodiments, the antibody or composition described herein inhibits the ability of MDSCs to suppress an immune response, inhibits immune suppressive activity of MDSCs, and/or inhibits the ability of MDSCs to promote expansion and/or function of Tregs. In various embodiments, the antibody is selected from the group consisting of XPA.42.089, XPA.42.068 and XPA.42.681.

In various embodiments, the antibody decreases the number of dendritic cells (DC) in a tumor and/or inhibits the tolerogenic function (e.g., tolerogenic effect) of dendritic cells. For example, in various embodiments, the antibody or composition described herein decreases the toleragenic effect of CD8+ dendritic cells. In one embodiment, the antibody is XPA.42.089 or XPA.42.681.

In another aspect, the disclosure provides a method for treating fibrosis comprising administering to a subject in need thereof a therapeutically effective amount of an antibody or a pharmaceutical composition contemplated herein.

In various embodiments, the antibody is administered with a second agent. In one embodiment, the second agent is selected from the group consisting of an extracellular matrix degrading protein, an anti-fibrotic agent, surgical therapy, chemotherapy, a cytotoxic agent, or radiation therapy. Exemplary second agents are disclosed in greater detail in the Detailed Description.

In various embodiments, therapy is administered on a period basis, for example, hourly, daily, weekly, every 2 weeks, every 3 weeks, monthly, or at a longer interval. In a related embodiment, in exemplary treatments, the antibody disclosed herein may be administered at a dose of about 1 mg/day, 5 mg/day, 10 mg/day, 20 mg/day, 50 mg/day, 75 mg/day, 100 mg/day, 150 mg/day, 200 mg/day, 250 mg/day, 500 mg/day or 1000 mg/day. These concentrations may be administered as a single dosage form or as multiple doses.

Also contemplated is a composition comprising any of the foregoing antibodies or compositions of the disclosure that bind TGFβ, or use thereof in preparation of a medicament, for treatment of any of the disorders described herein associated with TGFβ expression. Syringes, e.g., single use or pre-filled syringes, sterile sealed containers, e.g. vials, bottle, vessel, and/or kits or packages comprising any of the foregoing antibodies or compositions, optionally with suitable instructions for use, are also contemplated.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment", "some embodiments", "certain embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the invention. Where examples of values falling within ranges are disclosed, any of these examples are contemplated as possible endpoints of a range, any and all numeric values between such endpoints are contemplated, and any and all combinations of upper and lower endpoints are envisioned.

BRIEF DESCRIPTION OF THE DRAWINGS

(FIG. 2A) TGFβ 1; (FIG. 2B) TGFβ 2; (FIG. 2C) TGFβ 3.

DETAILED DESCRIPTION

Figure 1:
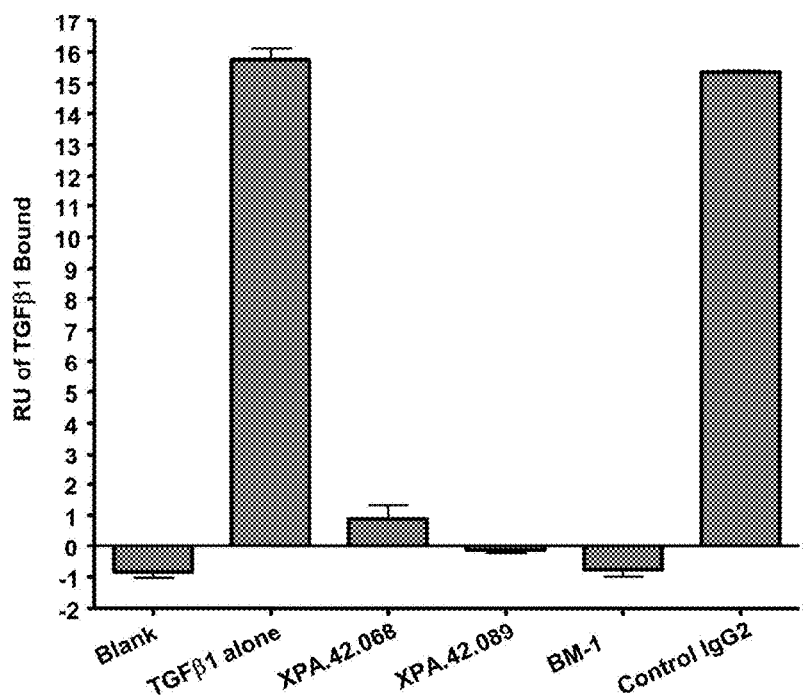
FIG. 1 is a graph showing competition of TGFβ1 binding to rhLAP by TGFβ antibodies.

The present disclosure provides therapeutics to treat conditions or disorders associated with TGFβ expression, for example, cancer and fibrosis. The present disclosure provides molecules or agents that interact with TGFβ and inhibit one or more of its functional effects, such as for example signaling through binding partners of TGFβ. The compositions disclosed herein advantageously have the ability to modulate immune cell activity in tumors, thereby providing, in one aspect, a method to treat cancer by affecting a cell population that directly or indirectly affects growth of the tumor.

In order that the disclosure may be more completely understood, several definitions are set forth.

As used herein, "target" or "target antigen" refers to any or all of the TGF-β molecules, including TGFβ1, TGFβ2 and TGFβ3.

As used herein "TGFβ" refers to any one or more isoforms of TGFβ, including TGFβ1, TGFβ2 and TGFβ3 or variants thereof. Likewise, the term "TGFβ receptor," unless otherwise indicated, refers to any receptor that binds at least one TGFβ isoform As used herein, the "desired biological activity" of an anti-target antibody is the ability to bind to TGFβ and inhibit one or more of its functional effects.

As used herein, a "condition" or "disorder associated with target expression" is a condition or disorder in which target activity is detrimental and includes diseases and other disorders in which high levels of target have been shown to be or are suspected of being either responsible for the pathophysiology of the disorder or a factor that contributes to a worsening of the disorder, as well as diseases and other disorders in which high levels of target expression are associated with undesirable clinical signs or symptoms. Such disorders may be evidenced, for example, by an increase in the levels of target secreted and/or on the cell surface and/or increased signalling in the affected cells or tissues of a subject suffering from the disorder. An increase in target levels may be detected, for example, using an target specific antibody as described herein.

Exemplary diseases, conditions or disorders associated with TGFβ expression that can be treated with an antibody substance that binds TGFβ (e.g., antibodies of the present disclosure) include cancers, such as lung cancer, prostate cancer, breast cancer, hepatocellular cancer, esophageal cancer, colorectal cancer, pancreatic cancer, bladder cancer, kidney cancer, ovarian cancer, stomach cancer, fibrotic cancer, glioma, and melanoma, eye (e.g., ocular, optic, ophthalmic or ophthalmological) diseases, conditions or disorders, disease conditions or disorders associated with fibrosis, e.g., fibroproliferative diseases, conditions or disorders, or diseases, conditions or disorders having an associated fibrosis.

Fibroproliferative diseases, conditions or disorders, or diseases conditions or disorders having an associated fibrosis, include those that affect any organ or tissue in the body, including, but not limited to the skin, lung, kidney, heart, brain and eye. Fibroproliferative diseases, conditions or disorders or diseases having an associated fibrosis include but are not limited to, pulmonary fibrosis, idiopathic pulmonary fibrosis, peribronchiolar fibrosis, interstitial lung disease, chronic obstructive pulmonary disease (COPD), small airway disease (e.g., obstructive bronchiolitis), emphysema, adult or acute respiratory distress syndrome (ARDS), acute lung injury (ALI), pulmonary fibrosis due to infectious or toxic agents, kidney fibrosis, glomerulonephritis (GN) of all etiologies, e.g., mesangial proliferative GN, immune GN, and crescentic GN, glomerulosclerosis, tubulointerstitial injury, renal interstitial fibrosis, renal fibrosis and all causes of renal interstitial fibrosis, renal fibrosis resulting from complications of drug exposure, including cyclosporin treatment of transplant recipients, e.g. cyclosporin treatment, HIV-associated nephropathy, transplant necropathy, diabetic kidney disease (e.g., diabetic nephropathy), nephrogenic systemic fibrosis, diabetes, idiopathic retroperitoneal fibrosis, scleroderma, liver fibrosis, hepatic diseases associated with excessive scarring and progressive sclerosis, including liver cirrhosis due to all etiologies, disorders of the biliary tree, hepatic dysfunction attributable to infections, fibrocystic diseases, cardiovascular diseases, such as congestive heart failure; dilated cardiomyopathy, myocarditis, vascular stenosis cardiac fibrosis (e.g., post-infarction cardiac fibrosis), post myocardial infarction, left ventricular hypertrophy, veno-occlusive disease, restenosis (e.g., post-angioplasty restenosis), arteriovenous graft failure, atherosclerosis, hypertension, hypertensive heart disease, cardiac hypertrophy, hypertrophic cardiomyopathy, heart failure, disease of the aorta, progressive systemic sclerosis, polymyositis, systemic lupus erythematosus, dermatomyositis, fascists, Raynaud's syndrome, rheumatoid arthritis, proliferative vitreoretinopathy, vitreoretinopathy of any etiology or fibrosis associated with ocular surgery such as treatment of glaucoma, retinal reattachment, cataract extraction, or drainage procedures of any kind, scarring in the cornea and conjunctiva, fibrosis in the corneal endothelium, alkali burn (e.g., alkali burn to the cornea), post-cataract surgery fibrosis of the lens capsule, excess scarring the tissue around the extraocular muscles in the strabismus surgery, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), fibrosis associated with post-retinal and glaucoma surgery, tractional retinal detachment in association with contraction of the tissue in diabetic retinopathy, Peyronie's disease, systemic sclerosis, post-spinal cord injury, osteoporosis, Camurati-Engelmann disease, Crohn's disease, scarring, Marfan syndrome, premature ovarian failure, Alzheimer's Disease and Parkinson's Disease, fibrosis due to surgical incisions or mechanical trauma, fibrosis associated with ocular surgery; and excessive or hypertrophic scar or keloid formation in the dermis occurring during wound healing resulting from trauma or surgical wounds.

Exemplary eye diseases, (e.g., ocular, optic, ophthalmic or ophthalmological diseases), conditions or disorders, include but are not limited to, fibroproliferative disorders, fibrosis of the eye, ophthalmic fibroses, retinal dysfunction, fibrosis associated with retinal dysfunction, wet or dry macular degeneration, proliferative vitreoretinopathy, vitreoretinopathy of any etiology, fibrosis associated with ocular surgery such as treatment of glaucoma, retinal reattachment, cataract extraction, or drainage procedures of any kind, scarring in the cornea and conjunctiva, fibrosis in the corneal endothelium, alkali burn (e.g., alkali burn to the cornea), post-cataract surgery fibrosis of the lens capsule, excess scarring in the tissue around the extraocular muscles in the strabismus surgery, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), fibrosis associated with post-retinal and glaucoma surgery, tractional retinal detachment in association with contraction of the tissue in diabetic retinopathy.

Exemplary fibroproliferative diseases, conditions or disorders of the eye, fibrosis of the eye, ocular fibrosis or ophthalmic fibroses include, but are not limited to, proliferative vitreoretinopathy, vitreoretinopathy of any etiology, fibrosis associated with retinal dysfunction, fibrosis associated with wet or dry macular degeneration, fibrosis associated with ocular surgery such as treatment of glaucoma, retinal reattachment, cataract extraction, or drainage procedures of any kind, scarring in the cornea and conjunctiva, fibrosis in the corneal endothelium, fibrosis associated with alkali burn, post-cataract surgery fibrosis of the lens capsule, excess scarring the tissue around the extraocular muscles in the strabismus surgery, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), fibrosis associated with post-retinal and glaucoma surgery, tractional retinal detachment in association with contraction of the tissue in diabetic retinopathy.

In various embodiments, the fibroproliferative disease, condition, or disorders of the eye is selected from the group consisting of proliferative vitreoretinopathy, fibrosis associated with ocular surgery, post-cataract surgery fibrosis of the lens, fibrosis of the corneal stroma and alkali burn.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa (κ) and lambda (λ) light chains. Heavy chains are classified as mu (μ), delta (Δ), gamma (γ), alpha (α), and epsilon (ε), and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., J. Mol. Biol. 196:901-917, 1987).

Immunoglobulin variable domains exhibit the same general structure of relatively conserved framework regions (FR) joined by three hypervariable regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk (J. Mol. Biol. 196:901-917, 1987); Chothia et al., (Nature 342:878-883, 1989).

The hypervariable region of an antibody refers to the CDR amino acid residues of an antibody which are responsible for antigen-binding. The hypervariable region comprises amino acid residues from a CDR [e.g., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)] and/or those residues from a hypervariable loop (e.g., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., J. Mol. Biol. 196: 901-917 (1987)]. CDRs have also been identified and numbered according to ImMunoGenTics (IMGT) numbering (Lefranc, M.-P., The Immunologist, 7, 132-136 (1999); Lefranc, M.-P. et al., Dev. Comp. Immunol., 27, 55-77 (2003), which describes the CDR locations in the light and heavy chain variable domains as follows: CDR1, approximately residues 27 to 38; CDR2, approximately residues 56 to 65; and, CDR3, approximately residues 105 to 116 (germline) or residues 105 to 117 (rearranged). In one embodiment, it is contemplated that the CDRs are located at approximately residues 26-31 (L1), 49-51 (L2) and 88-98 (L3) in the light chain variable domain and approximately residues 26-33 (H1), 50-58 (H2) and 97-111 (H3) in the heavy chain variable domain of an antibody heavy or light chain of approximately similar length to those disclosed herein. However, one of skill in the art understands that the actual location of the CDR residues may vary from the projected residues described above when the sequence of the particular antibody is identified.

Framework or FR residues are those variable domain residues other than the hypervariable region residues.

"Heavy chain variable region" as used herein refers to the region of the antibody molecule comprising at least one complementarity determining region (CDR) of said antibody heavy chain variable domain. The heavy chain variable region may contain one, two, or three CDR of said antibody heavy chain.

"Light chain variable region" as used herein refers to the region of an antibody molecule, comprising at least one complementarity determining region (CDR) of said antibody light chain variable domain. The light chain variable region may contain one, two, or three CDR of said antibody light chain, which may be either a kappa or lambda light chain depending on the antibody.

The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as a one, two, three, four, five or six CDR sequences, as long as the antibody retains the desired biological activity.

"Monoclonal antibody" refers to an antibody obtained from a population of substantially homogeneous antibodies, i.e., the individual antibodies comprising the population are identical except for possible naturally occurring mutations that may be present in minor amounts.

"Antibody variant" as used herein refers to an antibody polypeptide sequence that contains at least one amino acid substitution, deletion, or insertion in the variable region of the reference antibody variable region domains. Variants may be substantially homologous or substantially identical to the unmodified antibody.

A "chimeric antibody," as used herein, refers to an antibody containing sequence derived from two different antibodies (see, e.g., U.S. Pat. No. 4,816,567) which typically originate from different species. Most typically, chimeric antibodies comprise human and rodent antibody fragments, generally human constant and mouse variable regions.

A "neutralizing antibody" is an antibody molecule which is able to eliminate or significantly reduce a biological function of a target antigen to which it binds. Accordingly, a "neutralizing" anti-target antibody is capable of eliminating or significantly reducing a biological function, such as enzyme activity, ligand binding, or intracellular signaling.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, an antibody that "specifically binds" is "target specific", is "specific for" target or is "immunoreactive" with the target antigen refers to an antibody or antibody substance that binds the target antigen with greater affinity than with similar antigens. In one aspect of the disclosure, the target-binding polypeptides, or fragments, variants, or derivatives thereof, will bind with a greater affinity to human target as compared to its binding affinity to target of other, i.e., non-human, species, but binding polypeptides that recognize and bind orthologs of the target are within the scope provided.

For example, a polypeptide that is an antibody or fragment thereof "specific for" its cognate antigen indicates that the variable regions of the antibodies recognize and bind the polypeptide of interest with a detectable preference (i.e., able to distinguish the polypeptide of interest from other known polypeptides of the same family, by virtue of measurable differences in binding affinity, despite the possible existence of localized sequence identity, homology, or similarity between family members). It will be understood that specific antibodies may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody for use in the methods of the present disclosure are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies for use in the methods can be produced using any method known in the art.

The term "epitope" refers to that portion of any molecule capable of being recognized by and bound by a selective binding agent at one or more of the antigen binding regions. Epitopes usually consist of chemically active surface groupings of molecules, such as, amino acids or carbohydrate side chains, and have specific three-dimensional structural characteristics as well as specific charge characteristics. Epitopes as used herein may be contiguous or non-contiguous. Moreover, epitopes may be mimetic (mimotopes) in that they comprise a three dimensional structure that is identical to the epitope used to generate the antibody, yet comprise none or only some of the amino acid residues found in the target that were used to stimulate the antibody immune response. As used herein, a mimotope is not considered a different antigen from the epitope bound by the selective binding agent; the selective binding agent recognizes the same three-dimensional structure of the epitope and mimotope.

The term "derivative" when used in connection with antibody substances and polypeptides of the present disclosure refers to polypeptides chemically modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins. Derivatives retain the binding properties of underivatized molecules of the disclosure.

"Detectable moiety" or a "label" refers to a composition detectable by spectroscopic, photochemical, biochemical, immunochemical, or chemical means. For example, useful labels include 32P, 35S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample.

The term "therapeutically effective amount" is used herein to indicate the amount of target-specific composition of the disclosure that is effective to ameliorate or lessen symptoms or signs of disease associated with target protein expression.

The terms "treat", "treating" and "treatment", as used with respect to methods herein refer to eliminating, reducing, suppressing or ameliorating, either temporarily or permanently, either partially or completely, a clinical symptom, manifestation or progression of an event, disease or condition associated with TGFβ expression. Such treating need not be absolute to be useful.

The present disclosure provides a target-specific antibody, which may comprise those exemplary sequences set out in Table 1, fragments, variants and derivatives thereof, pharmaceutical formulations including a target-specific antibody recited above, methods of preparing the pharmaceutical formulations, and methods of treating patients with the pharmaceutical formulations and compounds.

Depending on the amino acid sequence of the constant domain of their heavy chains, immunoglobulins can be assigned to different classes, IgA, IgD, IgE, IgG and IgM, which may be further divided into subclasses or isotypes, e.g. IgG1, IgG2, IgG3, IgG4, IgA1 and IgA2. The subunit structures and three-dimensional configurations of different classes of immunoglobulins are well known. Different isotypes have different effector functions; for example, IgG1 and IgG3 isotypes have ADCC activity. An antibody disclosed herein, if it comprises a constant domain, may be of any of these subclasses or isotypes.

The antibodies of the present disclosure may exhibit binding affinity to one or more TGFβ antigens of a Kd of less than or equal to about $10^{-5}$ M, less than or equal to about $10^{-6}$ M, or less than or equal to about $10^{-7}$ M, or less than or equal to about $10^{-8}$ M, or less than or equal to about $10^{-9}$ M, $10^{-10}$ M, $10^{-11}$ M, or $10^{-12}$ M or less. Such affinities may be readily determined using conventional techniques, such as by equilibrium dialysis; by using surface plasmon resonance (SPR) technology (e.g., the BIAcore 2000 instrument, using general procedures outlined by the manufacturer); by radioimmunoassay using 125I labeled target antigen; or by another method set forth in the examples below or known to the skilled artisan. The affinity data may be analyzed, for example, by the method of Scatchard et al., (Ann N.Y. Acad. Sci., 51:660, 1949).

A KinExA kinetic exclusion assay is also useful to measure the affinity of an antibody for its antigen. KinExA technology measures binding events in the solution phase, rather than binding events between a solution phase and a solid phase. In addition, while many methods for measuring binding events require at least one reactant to be modified through immobilization or labeling, the KinExA method does not require modification of molecules under study. The KinExA method is believed to allow a wider range of binding constants to be measured than other methods currently available. Additional description about KinExA devices and operation for antibody characterization is available from the manufacturer (Sapidyne Instruments, Inc., Boise, Id.) and can be found in the published literature, for example U.S. Pat. No. 6,664,114 and Darling et al., "Kinetic Exclusion Assay Technology: Characterization of Molecular Interactions." Assay and Drug Development Technologies, 2004, 2:647-657.

Transforming Growth Factor β

TGFβ is a disulfide linked dimer that is synthesized as a preproprotein of about 400 amino acids (aa) which is cleaved prior to secretion to produce mature TGFβ. The N-terminal cleavage fragment, known as the "latency-associated peptide" (LAP), may remain noncovalently bound to the dimer, thereby inactivating TGFβ. TGFβ isolated in vivo, is found predominantly in the inactive, "latent" form, i.e., associated with LAP. Latent TGFβ complex may be activated in several ways, for example, by binding to a cell surface receptor called the cation-independent mannose-6-phosphate/insulin-like growth factor II receptor. Binding occurs through mannose-6-phosphate residues attached at glycosylation sites within LAP. Upon binding to the receptor, TGFβ is released in its mature form. Mature, active TGFβ is then free to bind to its receptor and exert its biological functions. The major TGFβ binding domain in the type II TGFβ receptor has been mapped to a 19 amino acid sequence (Demetriou et al., J. Biol. Chem., 271:12755, 1996). See also U.S. Pat. No. 7,867,496.

Currently, there are five known isoforms of TGFβ (TGFβ1 to TGFβ5; TGFβ1-3 are mammalian, TGFβ4 is found in chicken; and TGFβ5 found in frog), all of which are homologous among each other (60-80% identity), form homodimers of about 25 kDa, and act upon common TGFβ receptors (TGFβ-RI, TGFβ-RII, TGFβ-RIIB, and TGFβ-RIII). The structural and functional aspects of TGFβ as well as TGFβ receptors are well-known in the art (see, for example, Cytokine Reference, eds. Oppenheim et al., Academic Press, San Diego, Calif., 2001). TGFβ is well-conserved among species. For example, the amino acid sequences of rat and human mature TGFβ1s are nearly identical. See also U.S. Pat. No. 7,867,496.

TGFβ1 plays an important role in the process of wound healing in biological tissues (New Engl. J. Med., Vol. 331, p. 1286, 1994 and J. Cell. Biol., Vol. 119, p. 1017, 1992). At the site of wounded tissue, biological reactions such as infiltration of inflammatory cells and fibroblast cells, production of extracellular matrix (ECM) and vascularization, and cell growth for the subsequent tissue regeneration occur to repair the injured tissue. See also U.S. Pat. No. 7,579,186.

TGFβ2 deficient mice demonstrate significant developmental defects, including heart, lung, craniofacial, limb, spine, eye, ear and urogenital defects (Dunker et al., Eur J Biol 267:6982-8, 2001). TGFβ3 deficient mice demonstrate almost 100% lethality by 24 hrs after birth. These mice show significant palate impairment and delayed pulmonary development (Dunker et al., supra). TGFβ2 has also been implicated in the development of glaucoma (Luthen-Driscoll, Experimental Eye Res 81:1-4, 2005), fibrosis associated with Crohn's Disease (Van Assche et al., Inflamm Bowel Dis. 10:55-60, 2004), in wound healing and diabetic nephropathy (Pohlers et al., Biochim Biophys Acta 1792:746-56, 2009)

It has been observed that many human tumors (deMartin et al., EMBO J., 6: 3673 (1987), Kuppner et al., Int. J. Cancer, 42: 562 (1988)) and many tumor cell lines (Derynck et al., Cancer Res., 47: 707 (1987), Roberts et al., Br. J. Cancer, 57: 594 (1988)) produce TGFβ and suggests a possible mechanism for those tumors to evade normal immunological surveillance.

TGFβ isoform expression in cancer is complex and variable with different combinations of TGFβ isoforms having different roles in particular cancers. See e.g., U.S. Pat. No. 7,927,593. For example, TGFβ1 and TGFβ3 may play a greater role in ovarian cancer and its progression than TGFβ2; while TGFβ1 and TGFβ2 expression is greater in higher grade chondrosarcoma tumors than TGFβ3. In human breast cancer, TGFβ1 and TGFβ3 are highly expressed, with TGFβ3 expression appearing to correlate with overall survival—patients with node metastasis and positive TGFβ3 expression have poor prognostic outcomes. However, in colon cancer, TGFβ1 and TGFβ2 are more highly expressed than TGFβ3 and are present at greater circulating levels than in cancer-free individuals. In gliomas, TGFβ2 is important for cell migration.

TGFβ expression has also been implicated in the onset of various tissue fibroses, such as nephrosclerosis, pulmonary fibrosis and cirrhosis; as well as the onset of various states, such as chronic hepatitis, rheumatoid arthritis, vascular restenosis, and keloid of skin. Fibroses contemplated, including fibroses associated with a disease or disorder (e.g., fibroproliferative diseases or disorders), or treatment of a disease or disorder, include, but are not limited to, pulmonary fibrosis, idiopathic pulmonary fibrosis, peribronchiolar fibrosis, interstitial lung disease, chronic obstructive pulmonary disease (COPD), small airway disease (e.g., obstructive bronchiolitis), emphysema, adult or acute respiratory distress syndrome (ARDS), acute lung injury (ALI); pulmonary fibrosis due to infectious or toxic agents, kidney fibrosis, glomerulonephritis (GN) of all etiologies, e.g., mesangial proliferative GN, immune GN, and crescentic GN, glomerulosclerosis, tubulointerstitial injury, renal interstitial fibrosis, renal fibrosis and all causes of renal interstitial fibrosis, renal fibrosis resulting from complications of drug exposure, including cyclosporin treatment of transplant recipients, e.g. cyclosporin treatment, HIV-associated nephropathy; transplant necropathy, diabetic kidney disease (e.g., diabetic nephropathy), nephrogenic systemic fibrosis, diabetes, idiopathic retroperitoneal fibrosis, scleroderma, liver fibrosis, hepatic diseases associated with excessive scarring and progressive sclerosis, including liver cirrhosis due to all etiologies, disorders of the biliary tree, hepatic dysfunction attributable to infections, fibrocystic diseases, cardiovascular diseases, such as congestive heart failure; dilated cardiomyopathy, myocarditis, vascular stenosis, cardiac fibrosis (e.g., post-infarction cardiac fibrosis), post myocardial infarction, left ventricular hypertrophy, veno-occlusive disease, restenosis (e.g., post-angioplasty restenosis), arteriovenous graft failure, atherosclerosis, hypertension, hypertensive heart disease, cardiac hypertrophy, hypertrophic cardiomyopathy, heart failure, disease of the aorta, progressive systemic sclerosis; polymyositis, systemic lupus erythematosus, dermatomyositis, fascists, Raynaud's syndrome, rheumatoid arthritis, proliferative vitreoretinopathy, vitreoretinopathy of any etiology, fibrosis associated with ocular surgery such as treatment of glaucoma, fibrosis associated with retinal dysfunction, retinal reattachment, cataract extraction or drainage procedures of any kind, scarring in the cornea and conjunctiva, fibrosis in the corneal endothelium, fibrosis associated with alkali burn, post-cataract surgery fibrosis of the lens capsule, excess scarring the tissue around the extraocular muscles in the strabismus surgery, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), post-retinal and glaucoma surgery, tractional retinal detachment in association with contraction of the tissue in diabetic retinopathy, Peyronie's disease, systemic sclerosis, post-spinal cord injury, osteoporosis, Camurati-Engelmann disease, Crohn's disease, scarring, Marfan syndrome, premature ovarian failure, Alzheimer's Disease and Parkinson's Disease, fibrosis due to surgical incisions or mechanical trauma, fibrosis associated with ocular surgery; and excessive or hypertrophic scar or keloid formation in the dermis occurring during wound healing resulting from trauma or surgical wounds.

In pulmonary fibrosis and nephrosclerosis, the concentration of TGFβ is high and leads to the progress of the morbid states, such as fibrosis (Yamamoto et al., Kidney Int. 45:916-27, 1994 and Westergren-Thorsson et al., J. Clin. Invest. 92:632-7, 1993). The persistent tissue injury has been presumed to continuously transduce signals to express TGFβ, to suppress the negative regulation signal for TGFβ expression by ECM, or cause both events synergistically in pulmonary fibrosis and nephrosclerosis. Suppressing TGFβ activity and extracellular matrix accumulation in diagnosis and treatment of fibrotic diseases, using a inhibitor of TGFβ is disclosed in WO 1991/04748, WO 1993/10808 and WO 2000/40227. Neutralizing anti-TGF-beta antibodies have been used in the treatment of experimental diabetic kidney disease (Han and Ziyadeh, Peritoneal dialysis international, 19 Suppl 2: S234-237 (1999)). See also U.S. Pat. No. 7,527,791 further describing use of inhibitors of TGFβ in various indications, hereby incorporated by reference.

Exemplary eye diseases (e.g., ocular, optic, ophthalmic or ophthalmological diseases), conditions or disorders, include but are not limited to, fibroproliferative disorders, fibrosis of the eye, ophthalmic fibroses, retinal dysfunction, fibrosis associated with retinal dysfunction, wet or dry macular degeneration, proliferative vitreoretinopathy, vitreoretinopathy of any etiology, fibrosis associated with ocular surgery such as treatment of glaucoma, retinal reattachment, cataract extraction, or drainage procedures of any kind, scarring in the cornea and conjunctiva, fibrosis in the corneal endothelium, alkali burn (e.g., alkali burn to the cornea), post-cataract surgery fibrosis of the lens capsule, excess scarring in the tissue around the extraocular muscles in the strabismus surgery, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), fibrosis associated with post-retinal and glaucoma surgery, tractional retinal detachment in association with contraction of the tissue in diabetic retinopathy.

Exemplary fibroproliferative diseases, conditions or disorders of the eye, fibrosis of the eye, ocular fibrosis or ophthalmic fibroses include, but are not limited to, proliferative vitreoretinopathy, vitreoretinopathy of any etiology, fibrosis associated with retinal dysfunction, fibrosis associated with wet or dry macular degeneration, fibrosis associated with ocular surgery such as treatment of glaucoma, retinal reattachment, cataract extraction, or drainage procedures of any kind, scarring in the cornea and conjunctiva, fibrosis in the corneal endothelium, fibrosis associated with alkali burn, post-cataract surgery fibrosis of the lens capsule, excess scarring the tissue around the extraocular muscles in the strabismus surgery, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), fibrosis associated with post-retinal and glaucoma surgery, tractional retinal detachment in association with contraction of the tissue in diabetic retinopathy.

In various embodiments, the fibroproliferative disease, condition, or disorders of the eye is selected from the group consisting of proliferative vitreoretinopathy, fibrosis associated with ocular surgery, post-cataract surgery fibrosis of the lens, fibrosis of the corneal stroma and alkali burn.

Antibody Polypeptides

The present disclosure encompasses amino acid molecules encoding target specific antibodies. In exemplary embodiments, a target specific antibody of the disclosure can comprise a human kappa (κ) or a human lambda (λ) light chain or an amino acid sequence derived therefrom, or a human heavy chain or a sequence derived therefrom, or both heavy and light chains together in a single chain, dimeric, tetrameric or other form. In some embodiments, a heavy chain and a light chain of a target specific immunoglobulin are different amino acid molecules. In other embodiments, the same amino acid molecule contains a heavy chain variable region and a light chain variable region of a target specific antibody.

In some embodiments, the amino acid sequence of the human anti-target antibody comprises one or more CDRs of the amino acid sequence of the mature (i.e., missing signal sequence) light chain variable region (VL) of antibodies XPA.42.068, XPA.42.089 and XPA.42.681 set out in Table 1 or SEQ ID NOs: 4,8 and 12 or variants thereof, including CDR grafted, modified, humanized, chimeric, or Human Engineered antibodies or any other variants described herein. In some embodiments, the VL comprises the amino acid sequence from the beginning of the CDR1 to the end of the CDR3 of the light chain of any one of the foregoing antibodies.

In one embodiment, the target specific antibody comprises a light chain CDR1, CDR2 or CDR3 ((LCDR1, LCDR2, LCDR3), each of which are independently selected from the CDR1, CDR2 and CDR3 regions of an antibody having a light chain variable region comprising the amino acid sequence of the VL region set out in SEQ ID NOs: 4,8 and 12, a nucleic acid encoding the VH region set out in SEQ ID NOs: 4, 8, and 12, or encoded by a nucleic acid molecule encoding the VL region set out in SEQ ID NOs: 3, 7, and 11. In one embodiment, the light chain CDR1 is from approximately residues 24-34, CDR2 is from approximately residues 50-56 and CDR3 extends from approximately residues 89-97, according to Chothia numbering. In an alternate embodiment, it is contemplated that the heavy chain CDRs are located at approximately residues 27 to 38 (CDR1); approximately residues 56 to 65 (CDR2); and, approximately residues 105 to 116 (germline) or residues 105 to 117 (CDR3) according to ImMunoGenTics (IMGT) numbering. In one embodiment, it is contemplated that the light chain CDRs are located at approximately residues 26-31 (L1), 49-51 (L2) and 88-97 (L3) in the light chain variable domain of an antibody light chain of approximately similar length to those disclosed herein. A polypeptide of the target specific antibody may comprise the CDR1, CDR2 and CDR3 regions of an antibody comprising the amino acid sequence of the VL region selected from the group consisting of XPA.42.068, XPA.42.089 and XPA.42.681.

In some embodiments, the human target specific antibody comprises one or more CDRs of the amino acid sequence of the mature (i.e., missing signal sequence) heavy chain variable region (VH) of antibody XPA.42.068, XPA.42.089 and XPA.42.681 set out in Table 1 or SEQ ID NOs: 2, 6 and 10 or variants thereof. In some embodiments, the VH comprises the amino acid sequence from the beginning of the CDR1 to the end of the CDR3 of any one of the heavy chain of the foregoing antibodies.

In one embodiment, the target specific antibody comprises a heavy chain CDR1, CDR2 or CDR3 (HCDR1, HCDR2, HCDR3), each of which are independently selected from the CDR1, CDR2 and CDR3 regions of an antibody having a heavy chain variable region comprising the amino acid sequence of the VH region set out in SEQ ID NOs: 2, 6, and 10, a nucleic acid encoding the VH region set out in SEQ ID NOs: 2, 6, and 10, or encoded by a nucleic acid molecule encoding the VH region set out in SEQ ID NOs: 1, 5, and 9. It is further contemplated that a target specific antibody comprises a heavy chain CDR1, CDR2 or CDR3, each of which are independently selected from the CDR1, CDR2 and CDR3 regions of an antibody having a heavy chain variable region comprising the amino acid sequence of the VH region set out in SEQ ID NOs: 2, 6, and 10. In one embodiment, the heavy chain CDRs are located according to Chothia numbering: CDR1 is from approximately residues 26-35, CDR2 is from approximately residues 50-58 and CDR3 extends from approximately residues 95-102 (or 95-111 or 95-118). In an alternate embodiment, it is contemplated that the heavy chain CDRs are located at CDR1, approximately residues 27 to 38 (CDR1); approximately residues 56 to 65 (CDR2); and, CDR3, approximately residues 105 to 116 (germline) or residues 105 to 117 CDR3) according to ImMunoGenTics (IMGT) numbering. In one embodiment, it is contemplated that the heavy chain CDRs are located at approximately residues 26-33 (H1), 50-58 (H2) and 97-111 (H3) in the heavy chain variable domain of an antibody heavy chain of approximately similar length to those disclosed herein. A polypeptide of the target specific antibody may comprise the CDR1, CDR2 and CDR3 regions of an antibody comprising the amino acid sequence of the VH region selected from the group consisting of XPA.42.068, XPA.42.089 and XPA.42.681.

In another embodiment, the antibody comprises a mature light chain variable region as disclosed above and a mature heavy chain variable region as disclosed above, optionally paired as set forth in Table 1.

In exemplary embodiments, the disclosure contemplates:

a monoclonal antibody that retains any one, two, three, four, five, or six of HCDR1, HCDR2, HCDR3, LCDR1, LCDR2, or LCDR3 of any one of SEQ ID NOs: 13, 19 and 25; 14, 20 and 26; 15, 21 and 27 and SEQ ID NOs: 16, 22 and 28; 17, 23 and 29; and 18, 24 and 30, respectively, optionally including one or two mutations in any of such CDR(s), e.g., a conservative or non-conservative substitution, and optionally paired as set forth in Table 1;

a monoclonal antibody that retains all of HCDR1, HCDR2, HCDR3, or the heavy chain variable region of any one of SEQ ID NOs: 13, 19 and 25; 14, 20 and 26; and 15, 21 and 27, optionally including one or two mutations in any of such CDR(s), optionally further comprising any suitable heavy chain constant region, e.g., IgG1, IgG2, IgG3, IgG4, IgM, IgA1, IgA2, or IgE, a human sequence thereof, or a hybrid thereof;

a monoclonal antibody that retains all of LCDR1, LCDR2, LCDR3, or the light chain variable region of any one SEQ ID NOs: 16, 22 and 28; 17, 23 and 29; and 18, 24 and 30, optionally including one or two mutations in any of such CDR(s), optionally further comprising any suitable light chain constant region, e.g., a kappa or lambda light chain constant region, a human sequence thereof, or a hybrid thereof.

In some embodiments, the antibody comprises all three light chain CDRs, all three heavy chain CDRs, or all six CDRs of the light and heavy chain, paired as set forth in Table 1. In some exemplary embodiments, two light chain CDRs from an antibody may be combined with a third light chain CDR from a different antibody. Alternatively, a LCDR1 from one antibody can be combined with a LCDR2 from a different antibody and a LCDR3 from yet another antibody, particularly where the CDRs are highly homologous. Similarly, two heavy chain CDRs from an antibody may be combined with a third heavy chain CDR from a different antibody; or a HCDR1 from one antibody can be combined with a HCDR2 from a different antibody and a HCDR3 from yet another antibody, particularly where the CDRs are highly homologous.

In some embodiments, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the heavy chain variable region set out in SEQ ID NOs: 2, 6, and 10 and/or an amino acid sequence an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the light chain variable region set out in SEQ ID NOs: 4,8 and 12, the antibody further comprising at least one, two, three, four, five or all of HCDR1, HCDR2, HCDR3, LCDR1, LCDR2 or LCDR3. In some embodiments, the amino acid sequence with percentage identity to the light chain variable region may comprise one, two or three of the light chain CDRs. In other embodiments, the amino acid sequence with percentage identity to the heavy chain variable region may comprise one, two, or three of the heavy chain CDRs.

In another embodiment, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to all three HCDRs in the heavy chain variable region of an antibody sequence in Table 1, the CDRs set out in SEQ ID NOs: 13, 19 and 25; 14, 20 and 26; and 15, 21 and 27.

In a related embodiment, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the all three LCDRs in the light chain variable region of an antibody sequence in Table 1, the CDRs set out in SEQ ID NOs: 16, 22 and 28; 17, 23 and 29; and 18, 24 and 30.

In a further embodiment, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the all six CDRs in the heavy chain and light chain variable regions of an antibody sequence in Table 1, the CDRs set out in SEQ ID NOs: 13, 19 and 25; 14, 20 and 26; and 15, 21 27; 16, 22 and 28; 17, 23 and 29; and 18, 24 and 30.

It is contemplated that the antibodies of the disclosure may have one, or two or more amino acid substitutions in the CDR regions of the antibody, e.g., non-conservative or conservative substitutions.

In a related embodiment, the residues of the framework are altered. The heavy chain framework regions which can be altered lie within regions designated H-FR1, H-FR2, H-FR3 and H-FR4, which surround the heavy chain CDR residues, and the residues of the light chain framework regions which can be altered lie within the regions designated L-FR1, L-FR2, L-FR3 and L-FR4, which surround the light chain CDR residues. An amino acid within the framework region may be replaced, for example, with any suitable amino acid identified in a human framework or human consensus framework.

In exemplary embodiments, an anti-TGFβ antibody described herein specifically binds at least one isoform of TGFβ selected from the group consisting of TGFβ1, TGFβ2, and TGFβ3. In other embodiments, the anti-TGFβ antibody specifically binds: (a) TGFβ1, TGFβ2, and TGFβ3 ("pan-reactive antibody" or "pan-binding antibody"); (b) TGFβ1 and TGFβ2; (c) TGFβ1 and TGFβ3; and (d) TGFβ2 and TGFβ3. In exemplary embodiments, an anti-TGFβ antibody described herein binds at least one isoform of TGFβ with an affinity of $10^{-6}$ M, $10^{-7}$ M, $10^{-8}$ M, $10^{-9}$ M, $10^{-10}$ M, $10^{-11}$ M, or $10^{-12}$ M or less (lower meaning higher binding affinity), or optionally binds two TGFβ isoforms, or all of TGFβ1, 2, or 3 with an affinity of $10^{-6}$ M. $10^{-7}$ M, $10^{-8}$ M, $10^{-9}$ M, $10^{-10}$ M, $10^{-11}$ M, or $10^{-12}$ M or less for one or more of the isoforms. In other embodiments, an antibody described herein binds to TGFβ1 and TGFβ2 with at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% higher affinity (e.g., preferentially binds to TGFβ1 and TGFβ2) compared to binding to TGFβ3. Alternatively, an antibody described herein, binds each of TGFβ isoforms TGFβ1, TGFβ2 and TGFβ3 with an affinity within 3-fold, 5-fold or 10-fold of each other.

In some embodiments, antibody neutralization of TGFβ1 and TGFβ2 is at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% more potent that neutralization of TGFβ3.

Heavy and light chain amino acid sequences of XPA.42.089 are set out in SEQ ID NOs: 6 and 8, respectively. Heavy and light chain amino acid sequences of XPA.42.068 are set out in SEQ ID NOs: 2 and 4, respectively, and heavy and light chain amino acid sequences of XPA.42.681 are set out in SEQ ID NOs: 10 and 12, respectively.

Antibody Nucleic Acids

The present disclosure also encompasses nucleic acid molecules encoding target specific antibodies. In some embodiments, different nucleic acid molecules encode a heavy chain variable region and a light chain variable region of a target specific antibody. In other embodiments, the same nucleic acid molecule encodes a heavy chain and a light chain variable regions of a target specific antibody. In one embodiment, the nucleic acid encodes a target specific antibody of the present disclosure, as well as any of the polypeptides encoded by the nucleic acids described herein.

In one aspect, a nucleic acid molecule of the present disclosure comprises a nucleotide sequence that encodes the VL amino acid sequence of antibodies XPA.42.068, XPA.42.089 and XPA.42.681 set out in SEQ ID NOs: 4, 8 and 12 or a portion thereof. In a related aspect, the VL amino acid sequence is a consensus sequence. In some embodiments, the nucleic acid encodes the amino acid sequence of the light chain CDRs of said antibody. In some embodiments, said portion is a contiguous portion comprising CDR1-CDR3. In one embodiment, said portion comprises at least one, two or three of a light chain CDR1, CDR2, or CDR3 region, optionally with a different human or human consensus framework, and optionally with 1, or up to 2, or up to 3 mutations in the collective 3 CDRs.

In one embodiment the present disclosure provides antigen-binding compounds, including functional fragments, having a variable region amino acid sequence set forth in any one of SEQ ID NOs: 2, 6, and 10 and 4, 8 and 12. In a related embodiment, an aforementioned antigen binding compound is selected from the group consisting of a fully assembled tetrameric antibody, a monoclonal antibody a humanized antibody; a human antibody; a chimeric antibody; a multispecific antibody, an antibody fragment, Fab, F(ab')2; Fv; scFv or single-chain antibody fragment; a diabody; triabody, tetrabody, minibody, linear antibody; chelating recombinant antibody, a tribody or bibody, an intrabody, a nanobody, a small modular immunopharmaceutical (SMIP), a binding-domain immunoglobulin fusion protein, a camelized antibody, a VHH containing antibody, or a variant or derivative of any one of these antibodies, that comprise one or more CDR sequences of the disclosure and exhibit the desired biological activity, or a mixture of two or more antibodies. The antigen binding compounds of the present disclosure preferably retain binding affinity of $10^{-6}$, $10^{-7}$, $10^{-8}$, $10^{-9}$, $10^{-10}$ M, $10^{-11}$ M or less for one or more of TGFβ1, TGFβ2 and TGFβ3, as measured by surface plasmon resonance.

In one aspect, the antibodies of the present disclosure comprise a heavy chain variable region or light chain variable region as set out in amino acid sequences SEQ ID NOs: 2, 6, and 10 and SEQ ID NOs: 4, 8 and 12, respectively, as paired in Table 1. It is further contemplated that the antibodies may comprise all or part of the antibodies set out in the above amino acid sequences. In one embodiment, the antibodies comprise at least one of CDR1, CDR2, or CDR3 of the heavy chain of SEQ ID NOs: 2, 6, and 10, or at least one of CDR1, CDR2 or CDR3 of the light chain of SEQ ID NOs: 4, 8 and 12, as paired in Table 1.

In one embodiment, the heavy chain comprises an amino acid sequence identified as a heavy chain CDR3 sequence. Such a "heavy chain CDR3 sequence" (HCDR3) includes an amino acid sequence identified as a heavy chain CDR3 sequence set out in Table 1 and SEQ ID NOs: 15, 21 and 27. Alternatively, the HCDR3 sequence comprises an amino acid sequence that contains one or more amino acid changes (e.g., substitution, insertion or deletion) compared to any HCDR3 amino acid sequence identified in Table 1. Preferable substitutions include a substitution to an amino acid at the corresponding position within another HCDR3 of Table 1. Alternatively, the HCDR3 sequence may comprise a consensus amino acid sequence of the HCDR3 described herein.

The heavy chain comprising a HCDR3 sequence described above may further comprise a "heavy chain CDR1 sequence" (HCDR1), which includes any of the amino acid sequences identified as an HCDR1 in SEQ ID NOs: 13, 19 and 25 and Table 1, amino acid sequences that contain one or more amino acid changes compared to any HCDR1 identified in SEQ ID NOs: 13, 19 and 25 and Table 1, preferably a substitution to an amino acid at the corresponding position within another HCDR1 of Table 1, or a consensus sequence of the HCDR1 described herein.

Alternatively, the heavy chain comprising a HCDR3 sequence described above may further comprise a "heavy chain CDR2 sequence" (HCDR2), which includes any of the amino acid sequences identified as an HCDR2 in SEQ ID NOs: 14, 20 and 26 and Table 1, amino acid sequences that contain one or more amino acid changes compared to any HCDR2 identified in SEQ ID NOs: 14, 20 and 26 and Table 1, preferably a substitution to an amino acid at the corresponding position within another HCDR2 of Table 1, or a consensus sequence of the HCDR2 described herein.

The heavy chain comprising a heavy chain CDR3 sequence described above may also comprise both (a) a heavy chain CDR1 sequence described above and (b) a heavy chain CDR2 sequence of the invention described above.

One aspect of the present disclosure provides an antibody that binds target antigen comprising a heavy chain that comprises any one, two, and/or three of the heavy chain CDR sequences described below.

Any of the heavy chain CDR sequences described above may also include amino acids added to either end of the CDRs. Preparation of variants and derivatives of antibodies and antigen-binding compounds of the present invention, including affinity maturation or preparation of variants or derivatives containing amino acid analogs, is described in further detail herein. Exemplary variants include those containing a conservative or non-conservative substitution of a corresponding amino acid within the amino acid sequence, or a replacement of an amino acid with a corresponding amino acid of a different human antibody sequence.

Antibodies comprising any one of the heavy chains described above may further comprise a light chain, preferably a light chain that binds to target antigen, and most preferably a light chain comprising light chain CDR sequences described below.

Another aspect of the present disclosure provides an antibody that binds target antigen comprising a light chain that comprises any one, two, and/or three of the light chain CDR sequences described below.

Preferably the light chain comprises an amino acid sequence identified as a light chain CDR3 sequence. Such a "light chain CDR3 sequence" (LCDR3) includes an amino acid sequence identified as a light chain CDR3 sequence in Table 1 and within SEQ ID NOs: 18, 24 and 30. Alternatively, the light chain CDR3 sequence comprises an amino acid sequence that contains one or more amino acid changes (e.g., a substitution, insertion or deletion) compared to any light chain CDR3 amino acid sequence identified in Table 1. Preferable substitutions include a substitution to an amino acid at the corresponding position within another light chain CDR3 of Table 1.

The light chain comprising a light chain CDR3 sequence described above may further comprise a "light chain CDR1 sequence", which includes any of the amino acid sequences identified as a light chain CDR1 in SEQ ID NOs: 16, 22, and 28 or Table 1, amino acid sequences that contain one or more amino acid changes compared to any light chain CDR1 identified in SEQ ID NOs: 16, 22, and 28 or Table 1, preferably a substitution to an amino acid at the corresponding position within another light chain CDR1 of Table 1.

Alternatively, the light chain comprising a light chain CDR3 sequence described above may further comprise a "light chain CDR2 sequence", which includes any of the amino acid sequences identified as a light chain CDR2 in SEQ ID NOs: 17, 23 and 29 or Table 1, amino acid sequences that contain one or more amino acid changes compared to any light chain CDR2 identified in Table 1, preferably a substitution to an amino acid at the corresponding position within another light chain CDR2 of SEQ ID NOs: 17, 23 and 29 or Table 1.

In a related aspect, the present disclosure contemplates a purified polypeptide comprising at least one HCDR of SEQ ID NOs: 13-15, 19-21 and 25-27 or LCDR of SEQ ID NOs: 16-18, 22-24 and 28-30, wherein the framework regions of the heavy chain variable region and the framework regions of the light chain variable region comprise framework regions from a human antibody. In another embodiment, the framework regions of the heavy chain variable region and the framework regions of the light chain variable region are chemically altered by amino acid substitution to be more homologous to a different human antibody sequence. For example, within each heavy chain framework region (H-FR1-4) it is contemplated that at least one, at least two, at least three, at least four, at least five, or at least six native framework region residues of the heavy chain variable region have been altered by amino acid substitution, and wherein within each light chain framework region (L-FR1-4), at least one, at least two, at least three, at least four, at least five or at least six native framework residues of the light chain variable region have been altered by amino acid substitution.

The light chain comprising a light chain CDR3 sequence described above may also comprise both (a) a light chain CDR1 sequence described above and (b) a light chain CDR2 sequence described above.

Antibodies comprising any one of the light chain variable regions described above may further comprise a heavy chain variable region, optionally paired as described in Table 1, preferably a heavy chain variable region that binds to target antigen, and most preferably a heavy chain variable region comprising heavy chain CDR sequences described above.

In yet another embodiment, the antibody comprises a heavy chain variable region selected from the group consisting of SEQ ID NOs: 2, 6, and 10 and a light chain variable region selected from the group consisting of SEQ ID NOs: 4, 8 and 12.

In a related aspect, the nucleic acid molecule comprises a nucleotide sequence that encodes the light chain amino acid sequence of one of SEQ ID NOs: 4, 8 and 12 or a portion thereof. In one embodiment, the nucleic acid molecule comprises the light chain nucleotide sequence of any one of SEQ ID NOs: 3, 7 and 11 or a portion thereof. Nucleic acid molecules of the disclosure further include all nucleic acid sequences, including the sequences in SEQ ID NOs: 1, 3, 5, 7, 9 and 11 and nucleic acid sequences comprises degenerate codons based on the diversity of the genetic code, encoding an amino acid sequence of the heavy and light chain variable regions of an antibody described herein or any HCDRs or LCDRs described herein, and as set out in SEQ ID NOs: 2, 4, 6, 8, 10, 12 and 13-30, as well as nucleic acids that hybridize under highly stringent conditions, such as those described herein, to a nucleic acid sequence encoding an amino acid sequence of the heavy and light chain variable regions of an antibody described herein or any HCDRs or LCDRs described herein, and as set out in SEQ ID NOs: 2, 4, 6, 8, 10, 12 and 13-30.

In some embodiments, the nucleic acid molecule encodes a VL amino acid sequence that is at least 60, 65, 70, 75, 80, 85, 90, 91, 92, 93, 94, 95, 96 97, 98 or 99% identical to a VL amino acid sequence set out in SEQ ID NOs: 4, 8 and 12. Nucleic acid molecules of the disclosure include nucleic acids that hybridize under highly stringent conditions, such as those described herein, to a nucleic acid sequence encoding the light chain variable region amino acid sequence of SEQ ID NOs: 4, 8 and 12, or that has the light chain variable region nucleic acid sequence of SEQ ID NOs: 3, 7 and 11.

It is further contemplated that a nucleic acid molecule of the disclosure comprises a nucleotide sequence that encodes the VH amino acid sequence of any one of antibodies XPA.42.068, XPA.42.089 and XPA.42.681, or a portion thereof. In some embodiments, the nucleic acid encodes the amino acid sequence of the heavy chain CDRs of said antibody. In some embodiments, said portion is a contiguous portion comprising heavy chain CDR1-CDR3. In one embodiment, said portion comprises at least one, two or three of a heavy chain CDR1, CDR2, or CDR3 region, optionally with a different human or human consensus framework, and optionally with 1, or up to 2, or up to 3 mutations in the collective 3 CDRs.

In a related aspect, the nucleic acid molecule comprises a nucleotide sequence that encodes the heavy chain amino acid sequence of one of heavy chain of SEQ ID NOs: 2, 6, and 10 or a portion thereof. In one embodiment, the nucleic acid molecule comprises the heavy chain nucleotide sequence of SEQ ID NOs: 1, 5 and 9 or a portion thereof.

In some embodiments, the nucleic acid molecule encodes a VH amino acid sequence that is at least 70%, 75%, 80%, 85%, 90%, 95%, 96%, 97%, 98% or 99% identical to a VH amino acid sequence set out in SEQ ID NOs: 2, 6, and 10. In a related aspect, the VH amino acid sequence is a consensus sequence. Nucleic acid molecules of the disclosure further include nucleic acids that hybridize under highly stringent conditions, such as those described herein, to a nucleic acid sequence encoding the heavy chain variable region amino acid sequence of SEQ ID NOs: 2, 6, and 10, or that has the heavy chain variable region nucleic acid sequence of any one of SEQ ID NOs: 1, 5 and 9.

It is further contemplated that the nucleic acids of the disclosure may encode a full-length light chain or heavy chain of an antibody selected from XPA.42.068, XPA.42.089 and XPA.42.681 wherein a full-length light chain or full-length heavy chain comprises a light chain constant region or a heavy chain constant region, respectively, light chain constant regions optionally include unmodified or modified kappa or lambda regions, and heavy constant regions include unmodified or modified constant regions of any of the classes, such as IgG1, IgG2, IgG3, IgG4, IgM, IgA, IgD, or IgE.

In one aspect, the full length light chain antibody comprises the sequences set out in SEQ ID NOs: 4, 8 and 12. It is further contemplated that the nucleotide encoding the full-length light chain encodes the sequences SEQ ID NOs: 4, 8 and 12, and comprises the nucleotides sequence set forth in SEQ ID NOs: 3, 7 and 11.

In one aspect, the full length heavy chain antibody comprises the sequences in any one of SEQ ID NOs: 2, 6, and 10. It is further contemplated that the nucleotide encoding the full-length heavy chain encodes the sequences heavy chain of SEQ ID NOs: 2, 6, and 10 and comprises the nucleotides sequence set forth in any one of SEQ ID NOs: 1, 5 and 9.

In further embodiments, the disclosure provides an antibody that binds transforming growth factor beta (TGFβ)1, TGFβ2 and TGFβ3 comprising a light chain variable region and/or a heavy chain variable region, wherein (a) the light chain variable region comprises at least a CDR1 selected from SEQ ID NOs: 16, 22 and 28 or sequences at least 80% identical thereto, a CDR2 selected from SEQ ID NOs: 17, 23 and 29 or sequences at least 80% identical thereto, and/or a CDR3 selected from SEQ ID NOs: 18, 24 and 30 or sequences at least 80% identical thereto; and/or wherein (b) the heavy chain variable region comprises at least a CDR1 selected from SEQ ID NOs: 13, 19 and 25 or sequences at least 80% identical thereto, a CDR2 selected from SEQ ID NOs: 14, 20 and 26 or sequences at least 80% identical thereto, and/or a CDR3 selected from SEQ ID NOs: 15, 21 and 27 or sequences at least 80% identical thereto.

In a related embodiment, the light chain variable region comprises at least a CDR1 selected from SEQ ID NO: 16 or sequences at least 90% identical thereto, a CDR2 selected from SEQ ID NO: 17 or sequences at least 90% identical thereto, and a CDR3 selected from SEQ ID NO: 18 or sequences at least 90% identical thereto; and/or the heavy chain variable region comprises at least a CDR1 selected from SEQ ID NO: 13 or sequences at least 90% identical thereto, a CDR2 selected from SEQ ID NO: 14 or sequences at least 90% identical thereto, and a CDR3 selected from SEQ ID NO: 15 or sequences at least 90% identical thereto.

In another embodiment, the light chain variable region comprises at least a CDR1 selected from SEQ ID NO: 22 or sequences at least 90% identical thereto, a CDR2 selected from SEQ ID NO: 23 or sequences at least 90% identical thereto, and a CDR3 selected from SEQ ID NO: 24 or sequences at least 90% identical thereto; and/or the heavy chain variable region comprises at least a CDR1 selected from SEQ ID NO: 19 or sequences at least 90% identical thereto, a CDR2 selected from SEQ ID NO: 20 or sequences at least 90% identical thereto, and a CDR3 selected from SEQ ID NO: 21 or sequences at least 90% identical thereto.

In yet another embodiment, the light chain variable region comprises at least a CDR1 selected from SEQ ID NO: 28 or sequences at least 90% identical thereto, a CDR2 selected from SEQ ID NO: 29 or sequences at least 90% identical thereto, and a CDR3 selected from SEQ ID NO: 30 or sequences at least 90% identical thereto; and/or the heavy chain variable region comprises at least a CDR1 selected from SEQ ID NO: 25 or sequences at least 90% identical thereto, a CDR2 selected from SEQ ID NO: 26 or sequences at least 90% identical thereto, and a CDR3 selected from SEQ ID NO: 27 or sequences at least 90% identical thereto.

In exemplary embodiments, an antibody of the disclosure comprises a human kappa (κ) or a human lambda (λ) light chain or an amino acid sequence derived therefrom, or a human heavy chain or a sequence derived therefrom, or both heavy and light chains together in a single chain, dimeric, tetrameric or other form.

Monoclonal Antibodies

Monoclonal antibody refers to an antibody obtained from a population of substantially homogeneous antibodies. Monoclonal antibodies are generally highly specific, and may be directed against a single antigenic site, in contrast to conventional (polyclonal) antibody preparations that typically include different antibodies directed against the same or different determinants (epitopes). In addition to their specificity, the monoclonal antibodies are advantageous in that they are synthesized by the homogeneous culture, uncontaminated by other immunoglobulins with different specificities and characteristics.

Monoclonal antibodies may be made by the hybridoma method first described by Kohler et al. (Nature, 256:495-7, 1975) (Harlow & Lane; Antibodies: A Laboratory Manual, Cold Spring Harbor Laboratory Press: Cold Spring Harbor, N.Y. (1988); Goding, Monoclonal Antibodies: Principles and Practice, pp. 59-103 (Academic Press, 1986), or may be made by recombinant DNA methods (see, e.g., U.S. Pat. No. 4,816,567). The monoclonal antibodies may also be isolated from phage antibody libraries using the techniques described in, for example, Clackson et al., (Nature 352:624-628, 1991) and Marks et al., (J. Mol. Biol. 222:581-597, 1991). Additional methods for producing monoclonal antibodies are well-known to a person of ordinary skill in the art.

Monoclonal antibodies, such as those produced by the above methods, are suitably separated from culture medium, ascites fluid, or serum by conventional immunoglobulin purification procedures such as, for example, protein A-Sepharose, hydrophobic interaction chromatography (HIC), ion exchange chromatography, hydroxyapatite chromatography, gel electrophoresis, dialysis, and/or affinity chromatography.

It is further contemplated that antibodies of the present disclosure may be used as smaller antigen binding fragments of the antibody that are well-known in the art and described herein.

Antibody Fragments

Antibody fragments comprise a portion of an intact full length antibody, preferably an antigen binding or variable region of the intact antibody. Examples of antibody fragments include Fab, Fab', F(ab')2, and Fv fragments; diabodies; linear antibodies; single-chain antibody molecules (e.g., scFv); multispecific antibody fragments such as bispecific, trispecific, etc. antibodies (e.g., diabodies, triabodies, tetrabodies); minibody; chelating recombinant antibody; tribodies or bibodies; intrabodies; nanobodies; small modular immunopharmaceuticals (SMIP), binding-domain immunoglobulin fusion proteins; camelized antibodies; VHH containing antibodies; and other polypeptides formed from antibody fragments. See for example Holliger & Hudson (Nat. Biotech. 23:1126-36 (2005)).

Papain digestion of antibodies produces two identical antigen-binding fragments, called "Fab" fragments, monovalent fragments consisting of the VL, VH, CL and CH domains each with a single antigen-binding site, and a residual "Fc" fragment, whose name reflects its ability to crystallize readily. Pepsin treatment yields a F(ab')2 fragment, a bivalent fragment comprising two Fab fragments linked by a disulfide bridge at the hinge region, that has two "Single-chain Fv" or "scFv" antibody fragments comprise the VH and VL domains of antibody, wherein these domains are present in a single polypeptide chain. Preferably, the Fv polypeptide further comprises a polypeptide linker between the VH and VL domains that enables the Fv to form the desired structure for antigen binding, resulting in a single-chain antibody (scFv), in which a VL and VH region are paired to form a monovalent molecule via a synthetic linker that enables them to be made as a single protein chain (Bird et al., Science 242:423-426, 1988, and Huston et al., Proc. Natl. Acad. Sci. USA 85:5879-5883, 1988). For a review of scFv see Pluckthun, in The Pharmacology of Monoclonal Antibodies, vol. 1 13, Rosenburg and Moore eds., Springer-Verlag, New York, pp. 269-315 (1994). An Fd fragment consists of the VH and CH1 domains.

Additional antibody fragments include a domain antibody (dAb) fragment (Ward et al., Nature 341:544-546, 1989) which consists of a VH domain. Diabodies are bivalent antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., Proc. Natl. Acad. Sci. USA 90:6444-6448, 1993, and Poljak et al., Structure 2:1121-1123, 1994). Diabodies can be bispecific or monospecific.

Functional heavy-chain antibodies devoid of light chains are naturally occurring in nurse sharks (Greenberg et al., Nature 374:168-73, 1995), wobbegong sharks (Nuttall et al., Mol Immunol. 38:313-26, 2001) and Camelidae (Hamers-Casterman et al., Nature 363: 446-8, 1993; Nguyen et al., J. Mol. Biol. 275: 413, 1998), such as camels, dromedaries, alpacas and llamas. The antigen-binding site is reduced to a single domain, the VHH domain, in these animals. These antibodies form antigen-binding regions using only heavy chain variable region, i.e., these functional antibodies are homodimers of heavy chains only having the structure H2L2 (referred to as "heavy-chain antibodies" or "HCAbs"). Camelid VHH reportedly recombines with IgG2 and IgG3 constant regions that contain hinge, CH2, and CH3 domains and lack a CH1 domain (Hamers-Casterman et al., supra). For example, llama IgG1 is a conventional (H2L2) antibody isotype in which VH recombines with a constant region that contains hinge, CH1, CH2 and CH3 domains, whereas the llama IgG2 and IgG3 are heavy chain-only isotypes that lack CH1 domains and that contain no light chains. Camelid VHH domains have been found to bind to antigen with high affinity (Desmyter et al., J. Biol. Chem. 276:26285-90, 2001) and possess high stability in solution (Ewert et al., Biochemistry 41:3628-36, 2002). Classical VH-only fragments are difficult to produce in soluble form, but improvements in solubility and specific binding can be obtained when framework residues are altered to be more VHH-like. (See, e.g., Reichman, et al., J Immunol Methods 1999, 231:25-38.) Methods for generating antibodies having camelid heavy chains are described in, for example, in U.S. Patent Publication Nos. 20050136049 and 20050037421.

The variable domain of an antibody heavy-chain is the smallest fully functional antigen-binding fragment with a molecular mass of only 15 kDa, this entity is referred to as a nanobody (Cortez-Retamozo et al., Cancer Research 64:2853-57, 2004). A nanobody library may be generated from an immunized dromedary as described in Conrath et al., (Antimicrob Agents Chemother 45: 2807-12, 2001) or using recombinant methods as described in Revets et al, Expert Opin. Biol. Ther. 5(1):111-24 (2005).

Production of bispecific Fab-scFv ("bibody") and trispecific Fab-(scFv)(2) ("tribody") are described in Schoonjans et al. (J Immunol. 165:7050-57, 2000) and Willems et al. (J Chromatogr B Analyt Technol Biomed Life Sci. 786:161-76, 2003). For bibodies or tribodies, a scFv molecule is fused to one or both of the VL-CL (L) and VH-CH1 (Fd) chains, e.g., to produce a tribody two scFvs are fused to C-term of Fab while in a bibody one scFv is fused to C-term of Fab.

A "minibody" consisting of scFv fused to CH3 via a peptide linker (hingeless) or via an IgG hinge has been described in Olafsen, et al., Protein Eng Des Sel. 17(4):315-23, 2004.

Intrabodies are single chain antibodies which demonstrate intracellular expression and can manipulate intracellular protein function (Biocca, et al., EMBO J. 9:101-108, 1990; Colby et al., Proc Natl Acad Sci USA. 101:17616-21, 2004). Intrabodies, which comprise cell signal sequences which retain the antibody construct in intracellular regions, may be produced as described in Mhashilkar et al (EMBO J 14:1542-51, 1995) and Wheeler et al. (FASEB J. 17:1733-5. 2003). Transbodies are cell-permeable antibodies in which a protein transduction domain (PTD) is fused with single chain variable fragment (scFv) antibodies Heng et al., (Med Hypotheses. 64:1105-8, 2005).

Further contemplated are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

Thus, a variety of compositions comprising one, two, and/or three CDRs (e.g., a single CDR alone or in tandem, 2, 3, or other multiple repeats of the CDRs; or combinations of 2 or 3 CDRs alone or in tandem repeats; optionally, with a spacer amino acid sequence between the CDRs or repeats) of a heavy chain variable region or a light chain variable region of an antibody may be generated by techniques known in the art.

Multispecific Antibodies

In some embodiments, it may be desirable to generate multispecific (e.g. bispecific) anti-target antibody having binding specificities for at least two different epitopes of the same or different molecules. Exemplary bispecific antibodies may bind to two different epitopes of the target molecule. Alternatively, a target-specific antibody arm may be combined with an arm which binds to a cell surface molecule, such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the target. Bispecific antibodies may also be used to localize cytotoxic agents to cells which express or take up the target. These antibodies possess a target-binding arm and an arm which binds the cytotoxic agent (e.g., saporin, anti-interferon-60, vinca alkaloid, ricin A chain, methotrexate or radioactive isotope hapten). Bispecific antibodies can be prepared as full length antibodies or antibody fragments (e.g., F(ab')2 bispecific antibodies).

According to another approach for making bispecific antibodies, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., (Science 229:81-83, 1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from E. coli can be chemically coupled in vitro to form bispecific antibodies. (Shalaby et al., J. Exp. Med. 175:217-225 (1992))

Shalaby et al., J. Exp. Med. 175:217-225 (1992) describe the production of a fully humanized bispecific antibody F(ab')2 molecule. Each Fab' fragment was separately secreted from E. coli and subjected to directed chemical coupling in vitro to form the bispecfic antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. (Kostelny et al., J. Immunol. 148:1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al. (Proc. Natl. Acad. Sci. USA 90:6444-48, 1993) has provided an alternative mechanism for making bispecific antibody fragments.

The fragments comprise a heavy chain variable region (VH) connected to a light-chain variable region (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See Gruber et al., J. Immunol. 152: 5368 (1994).

Alternatively, the bispecific antibody may be a "linear antibody" produced as described in Zapata et al. Protein Eng. 8:1057-62 (1995). Linear antibodies comprise a pair of tandem Fd segments (VH-CH1-VH-CH1) which form a pair of antigen binding regions. Linear antibodies can be bispecific or monospecific.

In a further embodiment, the bispecific antibody may be a chelating recombinant antibody (CRAb). A chelating recombinant antibody recognizes adjacent and non-overlapping epitopes of the target antigen, and is flexible enough to bind to both epitopes simultaneously (Neri et al., J Mol Biol. 246:367-73, 1995).

Antibodies with more than two valencies are also contemplated. For example, trispecific antibodies can be prepared. (Tutt et al., J. Immunol. 147:60, 1991).

Chimeric and Humanized Antibodies

Because chimeric or humanized antibodies are less immunogenic in humans than the parental non-human (e.g., mouse) monoclonal antibodies, they can be used for the treatment of humans with far less risk of anaphylaxis.

Chimeric monoclonal antibodies, in which the variable Ig domains of a non-human (e.g., mouse) monoclonal antibody are fused to human constant Ig domains, can be generated using standard procedures known in the art (See Morrison et al., Proc. Natl. Acad. Sci. USA 81, 6841-6855 (1984); and, Boulianne et al, Nature 312, 643-646, (1984)).

Humanized antibodies may be achieved by a variety of methods including, for example: (1) grafting the non-human complementarity determining regions (CDRs) onto a human framework and constant region (a process referred to in the art as humanizing through "CDR grafting"), (2) transplanting the entire non-human variable domains, but "cloaking" them with a human-like surface by replacement of surface residues (a process referred to in the art as "veneering"), or, alternatively, (3) substituting human amino acids at positions determined to be unlikely to adversely effect either antigen binding or protein folding, but likely to reduce immunogenicity in a human environment (e.g., HUMAN ENGINEERING™). In the present disclosure, humanized antibodies will include both "humanized," "veneered" and "HUMAN ENGINEERED™" antibodies. These methods are disclosed in, e.g., Jones et al., Nature 321:522 525 (1986); Morrison et al., Proc. Natl. Acad. Sci., U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31:169-217 (1994); Studnicka et al. U.S. Pat. No. 5,766,886; Studnicka et al., (Protein Engineering 7: 805-814, 1994; Co et al., J. Immunol. 152, 2968-2976 (1994); Riechmann, et al., Nature 332:323-27 (1988); and Kettleborough et al., Protein Eng. 4:773-783 (1991) each of which is incorporated herein by reference.

CDR grafting involves introducing one or more of the six CDRs from the mouse heavy and light chain variable Ig domains into the appropriate four framework regions of human variable Ig domains. This technique (Riechmann, et al., Nature 332:323-27 (1988)), utilizes the conserved framework regions (FR1-FR4) as a scaffold to support the CDR loops which are the primary contacts with antigen. A disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen binding site (e.g., Co et al., J. Immunol. 152, 2968-2976 (1994)).

Human Antibodies from Transgenic Animals

Human antibodies to target protein can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598 6,657,103 and 6,833,268.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (Nat. Biotechnol. 14:845-851 (1996)), which contains gene sequences from unrearranged human antibody genes that code for the heavy and light chains of human antibodies. Immunization of a HuMAb-MOUSE® enables the production of fully human monoclonal antibodies to the target protein.

Also, Ishida et al. (Cloning Stem Cells. 4:91-102 (2002)) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TCMOUSE™ with various human antigens produces antibody responses comprising human antibodies. See also Jakobovits et al., Proc. Natl. Acad. Sci. USA, 90:2551 (1993); Jakobovits et al., Nature, 362:255-258 (1993); Bruggermann et al., Year in Immunol., 7:33 (1993); and U.S. Pat. No. 5,591,669, U.S. Pat. No. 5,589,369, U.S. Pat. No. 5,545,807; and U.S. Patent Publication No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human Antibodies from Display Technology

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments-usually Fv or Fab fragments-in bacteria and thus lack effector functions. Effector functions can be introduced by one of two strategies: The fragments can be engineered, for example, into complete antibodies for expression in mammalian cells, or into bispecific antibody fragments with a second binding site capable of triggering an effector function.

The present disclosure contemplates a method for producing target-specific antibody or antigen-binding portion thereof comprising the steps of synthesizing a library of human antibodies on phage, screening the library with target protein or a portion thereof, isolating phage that bind target, and obtaining the antibody from the phage. By way of example, one method for preparing the library of antibodies for use in phage display techniques comprises the steps of immunizing a non-human animal comprising human immunoglobulin loci with target antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant target-specific antibodies of the disclosure may be obtained in this way.

In another example, antibody producing cells can be extracted from non-immunized animals, RNA isolated from the extracted cells and reverse transcribed to produce cDNA, which is amplified using a primer, and inserted into a phage display vector such that antibodies are expressed on the phage. Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach. Antibodies of the disclosure can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. See e.g., U.S. Pat. No. 5,969,108. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum. Antibod. Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nuc Acid Res 19:4133-4137; and Barbas et al. (1991) Proc. Natl. Acad. Sci. USA 88:7978-7982.

In one embodiment, to isolate human antibodies specific for the target antigen with the desired characteristics, a human VH and VL library are screened to select for antibody fragments having the desired specificity. The antibody libraries used in this method are preferably scFv libraries prepared and screened as described herein and in the art (McCafferty et al., PCT Publication No. WO 92/01047, McCafferty et al., (Nature 348:552-554 (1990)); and Griffiths et al., (EMBO J 12:725-734 (1993)). The scFv antibody libraries preferably are screened using target protein as the antigen.

Alternatively, the Fd fragment (VH-CH1) and light chain (VL-CL) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); Winter, G., et al., Annu. Rev. Immunol. 12, 433-455 (1994); U.S. patent publication no. 20020004215 and WO 92/01047; U.S. patent publication no. 20030190317; and U.S. Pat. Nos. 6,054,287 and 5,877,293.

Watkins, "Screening of Phage-Expressed Antibody Libraries by Capture Lift," Methods in Molecular Biology, Antibody Phage Display: Methods and Protocols 178:187-193 (2002), and U.S. patent publication no. 20030044772, published Mar. 6, 2003, describe methods for screening phage-expressed antibody libraries or other binding molecules by capture lift, a method involving immobilization of the candidate binding molecules on a solid support.

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, f1, If1, Ike, ZJ/Z, Ff and one of the class II phages Xf, Pf1 and Pf3. The phage may be M13, or fd or a derivative thereof.

Once initial human VL and VH segments are selected, "mix and match" experiments, in which different pairs of the initially selected VL and VH segments are screened for target binding, are performed to select preferred VL/VH pair combinations. Additionally, to further improve the quality of the antibody, the VL and VH segments of the preferred VL/VH pair(s) can be randomly mutated, preferably within the any of the CDR1, CDR2 or CDR3 region of VH and/or VL, in a process analogous to the in vivo somatic mutation process responsible for affinity maturation of antibodies during a natural immune response. This in vitro affinity maturation can be accomplished by amplifying VL and VH regions using PCR primers complimentary to the VH CDR1, CDR2, and CDR3, or VL CDR1, CDR2, and CDR3, respectively, which primers have been "spiked" with a random mixture of the four nucleotide bases at certain positions such that the resultant PCR products encode VL and VH segments into which random mutations have been introduced into the VH and/or VL CDR3 regions. These randomly mutated VL and VH segments can be rescreened for binding to target antigen.

Following screening and isolation of an target specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the disclosure, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be carried out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3; and phage displaying or encoding a binding molecule fused to a capsid protein.

Antibodies are also generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described therein. This technique is also disclosed in Marks et al, (Bio/Technology, 10:779-783 (1992)).

Methods for display of peptides on the surface of yeast, microbial and mammalian cells have also been used to identify antigen specific antibodies. See, for example, U.S. Pat. Nos. 5,348,867; 5,723,287; 6,699,658; Wittrup, Curr Op. Biotech. 12:395-99 (2001); Lee et al, Trends in Biotech. 21(1) 45-52 (2003); Surgeeva et al, Adv. Drug Deliv. Rev. 58: 1622-54 (2006). Antibody libraries may be attached to yeast proteins, such as agglutinin, effectively mimicking the cell surface display of antibodies by B cells in the immune system.

In addition to phage display methods, antibodies may be isolated using in vitro display methods and microbial cell display, including ribosome display and mRNA display (Amstutz et al, Curr. Op. Biotech. 12: 400-05 (2001)). Selection of polypeptide using ribosome display is described in Hanes et al., (Proc. Natl Acad Sci USA, 94:4937-4942 (1997)) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

Amino Acid Sequence Variants

It is contemplated that modified polypeptide compositions comprising one, two, three, four, five, and/or six CDRs of an antibody are generated, wherein a CDR is altered to provide increased specificity or affinity to the target molecule. Sites within antibody CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the target site. For example, using the conserved framework sequences surrounding the CDRs, PCR primers complementary to these consensus sequences are generated to amplify the antigen-specific CDR sequence located between the primer regions. Techniques for cloning and expressing nucleotide and polypeptide sequences are well-established in the art [see e.g. Sambrook et al., Molecular Cloning: A Laboratory Manual, 2nd Edition, Cold Spring Harbor, N.Y. (1989)]. The amplified CDR sequences are ligated into an appropriate plasmid. The plasmid comprising one, two, three, four, five and/or six cloned CDRs optionally contains additional polypeptide encoding regions linked to the CDR.

Antibody substances comprising the modified CDRs are screened for binding affinity for the original antigen. Additionally, the antibody or polypeptide is further tested for its ability to neutralize the activity of the target antigens. For example, antibodies of the disclosure may be analyzed as set out in the Examples to determine their ability to interfere with the biological activity of target antigen.

Modifications may be made by conservative or nonconservative amino acid substitutions described in greater detail below. "Insertions" or "deletions" are preferably in the range of about 1 to 20 amino acids, more preferably 1 to 10 amino acids. The variation may be introduced by systematically making substitutions of amino acids in an antibody polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for altering antibody sequences and expressing antibody polypeptide compositions useful in the disclosure are described in greater detail below.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue or the antibody (including antibody fragment) fused to an epitope tag or a salvage receptor epitope. Other insertional variants of the antibody molecule include the fusion to a polypeptide which increases the serum half-life of the antibody, e.g. at the N-terminus or C-terminus.

The term "epitope tagged" refers to the antibody fused to an epitope tag. The epitope tag polypeptide has enough residues to provide an epitope against which an antibody there against can be made, yet is short enough such that it does not interfere with activity of the antibody. The epitope tag preferably is sufficiently unique so that the antibody there against does not substantially cross-react with other epitopes. Suitable tag polypeptides generally have at least 6 amino acid residues and usually between about 8-50 amino acid residues (preferably between about 9-30 residues). Examples include the flu hemagglutinin (HA) tag polypeptide and its antibody 12CA5 (Field et al., Mol. Cell. Biol. 8: 2159-2165 (1988)); the c-myc tag and the 8F9, 3C7, 6E10, G4, B7 and 9E10 antibodies thereto (Evan et al., Mol. Cell. Biol. 5:3610-16 (1985)); and the Herpes Simplex virus glycoprotein D (gD) tag and its antibody (Paborsky et al., Protein Engineering 3:547-53 (1990)). Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the disclosure.

As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Another type of variant is an amino acid substitution variant. These variants have at least one amino acid residue in the antibody molecule removed and a different residue inserted in its place. Substitutional mutagenesis within any of the hypervariable or CDR regions or framework regions is contemplated. Conservative substitutions involve replacing an amino acid with another member of its class. Nonconservative substitutions involve replacing a member of one of these classes with a member of another class.

Conservative amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E).

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Affinity Maturation

Affinity maturation generally involves preparing and screening antibody variants that have substitutions within the CDRs of a parent antibody and selecting variants that have one or more improved biological properties such as binding affinity relative to the parent antibody. A convenient way for generating such substitutional variants is affinity maturation using phage display. Briefly, several hypervariable region sites (e.g. 6-7 sites) may be mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., J. Mol. Biol. 260, 359-68 (1996) Irving et al., Immunotechnology 2, 127-143 (1996)), and saturation mutagenesis (Nishimiya et al., J. Biol. Chem. 275:12813-20 (2000); Chowdhury, P. S. Methods Mol. Biol. 178, 269-85 (2002)) are typical examples of stochastic mutagenesis methods (Rajpal et al., Proc Natl Acad Sci USA. 102:8466-71 (2005)). Nonstochastic techniques often use alanine-scanning or site-directed mutagenesis to generate limited collections of specific variants. Some methods are described in further detail below.

Affinity Maturation Via Panning Methods—

Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (Cancer Immunol Immunother. 50:163-71 (2001)). Methods of affinity maturation using phage display technologies are described elsewhere herein and known in the art (see e.g., Daugherty et al., Proc Natl Acad Sci USA. 97:2029-34 (2000)).

Look-Through Mutagenesis—

Look-through mutagenesis (LTM) (Rajpal et al., Proc Natl Acad Sci USA. 102:8466-71 (2005)) provides a method for rapidly mapping the antibody-binding site. For LTM, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all variants. After positive selection, clones with improved binding are sequenced, and beneficial mutations are mapped.

Error Prone PCR—

Error-prone PCR involves the randomization of nucleic acids between different selection rounds. The randomization occurs at a low rate by the intrinsic error rate of the polymerase used but can be enhanced by error-prone PCR (Zaccolo et al., J. Mol. Biol. 285:775-783 (1999)) using a polymerase having a high intrinsic error rate during transcription (Hawkins et al., J Mol Biol. 226:889-96 (1992)). After the mutation cycles, clones with improved affinity for the antigen are selected using routine methods in the art.

DNA Shuffling—

Nucleic acid shuffling is a method for in vitro or in vivo homologous recombination of pools of shorter or smaller polynucleotides to produce variant polynucleotides. DNA shuffling has been described in U.S. Pat. No. 6,605,449, U.S. Pat. No. 6,489,145, WO 02/092780 and Stemmer, Proc. Natl. Acad. Sci. USA, 91:10747-51 (1994). Generally, DNA shuffling is comprised of 3 steps: fragmentation of the genes to be shuffled with DNase I, random hybridization of fragments and reassembly or filling in of the fragmented gene by PCR in the presence of DNA polymerase (sexual PCR), and amplification of reassembled product by conventional PCR.

DNA shuffling differs from error-prone PCR in that it is an inverse chain reaction. In error-prone PCR, the number of polymerase start sites and the number of molecules grows exponentially. In contrast, in nucleic acid reassembly or shuffling of random polynucleotides the number of start sites and the number (but not size) of the random polynucleotides decreases over time.

In the case of an antibody, DNA shuffling allows the free combinatorial association of all of the CDR1s with all of the CDR2s with all of the CDR3s, for example. It is contemplated that multiple families of sequences can be shuffled in the same reaction. Further, shuffling generally conserves the relative order, such that, for example, CDR1 will not be found in the position of CDR2. Rare shufflants will contain a large number of the best (e.g. highest affinity) CDRs and these rare shufflants may be selected based on their superior affinity.

The template polynucleotide which may be used in DNA shuffling may be DNA or RNA. It may be of various lengths depending on the size of the gene or shorter or smaller polynucleotide to be recombined or reassembled. Preferably, the template polynucleotide is from 50 bp to 50 kb. The template polynucleotide often should be double-stranded.

It is contemplated that single-stranded or double-stranded nucleic acid polynucleotides having regions of identity to the template polynucleotide and regions of heterology to the template polynucleotide may be added to the template polynucleotide, during the initial step of gene selection. It is also contemplated that two different but related polynucleotide templates can be mixed during the initial step.

Alanine Scanning—

Alanine scanning mutagenesis can be performed to identify hypervariable region residues that contribute significantly to antigen binding. Cunningham and Wells, (Science 244:1081-1085 (1989)). A residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution.

Computer-Aided Design—

Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Alternatively, or in addition, a variety of other affinity maturation techniques known in the art may be used, including for example techniques described in published patent applications WO2009/088933; WO2009/088928; WO2009/088924; as well as Clackson et al., Nature 352:624-628, 1991; Marks et al., Biotechnology 10:779-783, 1992; Virnekas et al., Nucleic Acids Res. 22:5600-5607, 1994; Glaser et al., J. Immunol. 149:3903-3913, 1992; Jackson et al., J. Immunol. 154:3310-3319, 1995; Schier et al., J. Mol. Biol. 255:28-43, 1996; and Yang et al., J. Mol. Biol. 254:392-403, 1995, incorporated by reference herein in their entirety.

Altered Glycosylation

Antibody variants can also be produced that have a modified glycosylation pattern relative to the parent antibody, for example, deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to an antibody by inserting or substituting one or more serine or threonine residues to the sequence of the original antibody.

Fc glycans influence the binding of IgG to Fc receptors and C1q, and are therefore important for IgG effector functions. Antibody variants with modified Fc glycans and altered effector function may be produced. For example, antibodies with modified terminal sugars such as sialic acids, core fucose, bisecting N-acetylglucosamine, and mannose residues may have altered binding to the FcγRIIIa receptor and altered ADCC activity. In a further example, antibodies with modified terminal galactose residues may have altered binding to C1q and altered CDC activity (Raju, Curr. Opin. Immunol. 20: 471-78 (2008).

Also contemplated are antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., Biotechnol Bioeng. 87:614-22 (2004)). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., Mol Immunol. 26:1113-23 (1989)). Some host cell strains, e.g. Lec13 or rat hybridoma YB2/0 cell line naturally produce antibodies with lower fucosylation levels. (Shields et al., J Biol Chem. 277:26733-40 (2002); Shinkawa et al., J Biol Chem. 278: 3466-73 (2003)). An increase in the level of bisected carbohydrate, e.g. through recombinantly producing antibody in cells that overexpress GnTIII enzyme, has also been determined to increase ADCC activity (Umana et al., Nat Biotechnol. 17:176-80 (1999)). It has been predicted that the absence of only one of the two fucose residues may be sufficient to increase ADCC activity (Ferrara et al., Biotechnol Bioeng. 93:851-61 (2006)).

Variants with Altered Effector Function

Other modifications of the antibody are contemplated. In one aspect, it may be desirable to modify the antibody of the disclosure with respect to effector function, for example, to enhance the effectiveness of the antibody in treating cancer. One method for modifying effector function teaches that cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., (J. Exp Med. 176: 1191-1195 (1992)) and Shopes, B. (J. Immunol. 148: 2918-2922 (1992)). Homodimeric antibodies with enhanced anti-tumor activity may also be prepared using heterobifunctional cross-linkers as described in Wolff et al., (Cancer Research 53: 2560-2565 (1993)). Alternatively, an antibody can be engineered which has dual Fc regions and may thereby have enhanced complement lysis and ADCC capabilities. See Stevenson et al., (Anti-Cancer Drug Design 3: 219-230 (1989)). In addition, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Also see Steplewski et al., (Proc Natl Acad Sci USA. 85:4852-56 (1998)), which described chimeric antibodies wherein a murine variable region was joined with human gamma 1, gamma 2, gamma 3, and gamma 4 constant regions.

In certain embodiments of the present disclosure, it may be desirable to use an antibody fragment, rather than an intact antibody, to increase tumor penetration, for example. In this case, it may be desirable to modify the antibody fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, e.g., WO96/32478).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the CL region or VL region, or both, of the antibody fragment. See also International applications WO 97/34631 and WO 96/32478 which describe Fc variants and their interaction with the salvage receptor.

Thus, antibodies of the present disclosure may comprise a human Fc portion, a human consensus Fc portion, or a variant thereof that retains the ability to interact with the Fc salvage receptor, including variants in which cysteines involved in disulfide bonding are modified or removed, and/or in which the a met is added at the N-terminus and/or one or more of the N-terminal 20 amino acids are removed, and/or regions that interact with complement, such as the C1q binding site, are removed, and/or the ADCC site is removed [see, e.g., Sarmay et al., Molec. Immunol. 29:633-9 (1992)].

Previous studies mapped the binding site on human and murine IgG for FcR primarily to the lower hinge region composed of IgG residues 233-239. Other studies proposed additional broad segments, e.g. Gly316-Lys338 for human Fc receptor I, Lys274-Arg301 and Tyr407-Arg416 for human Fc receptor III, or found a few specific residues outside the lower hinge, e.g., Asn297 and Glu318 for murine IgG2b interacting with murine Fc receptor II. The report of the 3.2-Å crystal structure of the human IgG1 Fc fragment with human Fc receptor IIIA delineated IgG1 residues Leu234-Ser239, Asp265-Glu269, Asn297-Thr299, and Ala327-Ile332 as involved in binding to Fc receptor IIIA. It has been suggested based on crystal structure that in addition to the lower hinge (Leu234-Gly237), residues in IgG CH2 domain loops FG (residues 326-330) and BC (residues 265-271) might play a role in binding to Fc receptor IIA. See Shields et al., (J. Biol. Chem., 276:6591-604 (2001)), incorporated by reference herein in its entirety. Mutation of residues within Fc receptor binding sites can result in altered effector function, such as altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position).

Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG1 residues that affected binding to Fc receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A327S, P329A, D265A and D270A reduced binding. In addition to the residues identified above for all FcR, additional IgG1 residues that reduced binding to Fc receptor IIIA by 40% or more are as follows: Ser239, Ser267 (Gly only), His268, Glu293, Gln295, Tyr296, Arg301, Val303, Lys338, and Asp376. Variants that improved binding to FcRIIIA include T256A, K290A, S298A, E333A, K334A, and A339T. Lys414 showed a 40% reduction in binding for FcRIIA and FcRIIB, Arg416 a 30% reduction for FcRIIA and FcRIIIA, Gln419 a 30% reduction to FcRIIA and a 40% reduction to FcRIIB, and Lys360 a 23% improvement to FcRIIIA See also Presta et al., (Biochem. Soc. Trans. 30:487-490, 2001), incorporated herein by reference in its entirety, which described several positions in the Fc region of IgG1 were found which improved binding only to specific Fc gamma receptors (R) or simultaneously improved binding to one type of Fc gamma R and reduced binding to another type. Selected IgG1 variants with improved binding to Fc gamma RIIIa were then tested in an in vitro antibody-dependent cellular cytotoxicity (ADCC) assay and showed an enhancement in ADCC when either peripheral blood mononuclear cells or natural killer cells were used.

For example, U.S. Pat. No. 6,194,551, incorporated herein by reference in its entirety, describes variants with altered effector function containing mutations in the human IgG Fc region, at amino acid position 329, 331 or 322 (using Kabat numbering), some of which display reduced C1q binding or CDC activity. As another example, U.S. Pat. No. 6,737,056, incorporated herein by reference in its entirety, describes variants with altered effector or Fc-gamma-receptor binding containing mutations in the human IgG Fc region, at amino acid position 238, 239, 248, 249, 252, 254, 255, 256, 258, 265, 267, 268, 269, 270, 272, 276, 278, 280, 283, 285, 286, 289, 290, 292, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 (using Kabat numbering), some of which display receptor binding profiles associated with reduced ADCC or CDC activity. Of these, a mutation at amino acid position 238, 265, 269, 270, 327 or 329 are stated to reduce binding to FcRI, a mutation at amino acid position 238, 265, 269, 270, 292, 294, 295, 298, 303, 324, 327, 329, 333, 335, 338, 373, 376, 414, 416, 419, 435, 438 or 439 are stated to reduce binding to FcRII, and a mutation at amino acid position 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 is stated to reduce binding to FcRIII.

U.S. Pat. No. 5,624,821, incorporated by reference herein in its entirety, reports that C1q binding activity of an murine antibody can be altered by mutating amino acid residue 318, 320 or 322 of the heavy chain and that replacing residue 297 (Asn) results in removal of lytic activity.

U.S. Patent Publication No. 20040132101, incorporated by reference herein in its entirety, describes variants with mutations at amino acid positions 240, 244, 245, 247, 262, 263, 266, 299, 313, 325, 328, or 332 (using Kabat numbering) or positions 234, 235, 239, 240, 241, 243, 244, 245, 247, 262, 263, 264, 265, 266, 267, 269, 296, 297, 298, 299, 313, 325, 327, 328, 329, 330, or 332 (using Kabat numbering), of which mutations at positions 234, 235, 239, 240, 241, 243, 244, 245, 247, 262, 263, 264, 265, 266, 267, 269, 296, 297, 298, 299, 313, 325, 327, 328, 329, 330, or 332 may reduce ADCC activity or reduce binding to an Fc gamma receptor.

Chappel et al. (Proc Natl Acad Sci USA. 88:9036-40 (1991)), incorporated herein by reference in its entirety, report that cytophilic activity of IgG1 is an intrinsic property of its heavy chain CH2 domain. Single point mutations at any of amino acid residues 234-237 of IgG1 significantly lowered or abolished its activity. Substitution of all of IgG1 residues 234-237 (LLGG) into IgG2 and IgG4 were required to restore full binding activity. An IgG2 antibody containing the entire ELLGGP sequence (residues 233-238) was observed to be more active than wild-type IgG1.

Isaacs et al. (J Immunol. 161:3862-9 (1998)), incorporated herein by reference in its entirety, report that mutations within a motif critical for Fc gammaR binding (glutamate 233 to proline, leucine/phenylalanine 234 to valine, and leucine 235 to alanine) completely prevented depletion of target cells. The mutation glutamate 318 to alanine eliminated effector function of mouse IgG2b and also reduced the potency of human IgG4.

Armour et al. (Mol Immunol. 40:585-93 (2003)), incorporated by reference herein in its entirety, identified IgG1 variants which react with the activating receptor, FcgammaRIIa, at least 10-fold less efficiently than wildtype IgG1 but whose binding to the inhibitory receptor, FcgammaRIIb, is only four-fold reduced. Mutations were made in the region of amino acids 233-236 and/or at amino acid positions 327, 330 and 331. See also WO 99/58572, incorporated by reference herein in its entirety.

Xu et al. (J Biol Chem. 269:3469-74 (1994)), incorporated by reference herein in its entirety, report that mutating IgG1 Pro331 to Ser markedly decreased C1q binding and virtually eliminated lytic activity. In contrast, the substitution of Pro for Ser331 in IgG4 bestowed partial lytic activity (40%) to the IgG4 Pro331 variant.

Schuurman et al. (Mol Immunol. 38:1-8 (2001)), incorporated by reference herein in its entirety, report that mutating one of the hinge cysteines involved in the inter-heavy chain bond formation, Cys226, to serine resulted in a more stable inter-heavy chain linkage. Mutating the IgG4 hinge sequence Cys-Pro-Ser-Cys to the IgG1 hinge sequence Cys-Pro-Pro-Cys also markedly stabilizes the covalent interaction between the heavy chains.

Angal et al. (Mol Immunol. 30:105-8 (1993)), incorporated by reference herein in its entirety, report that mutating the serine at amino acid position 241 in IgG4 to proline (found at that position in IgG1 and IgG2) led to the production of a homogeneous antibody, as well as extending serum half-life and improving tissue distribution compared to the original chimeric IgG4.

Covalent Modifications

Covalent modifications of the antibody are also included within the scope of this disclosure. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R—N.dbd.C.dbd.N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this disclosure.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 and in Aplin and Wriston, (CRC Crit. Rev. Biochem., pp. 259-306 (1981)).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al., (Arch. Biochem. Biophys. 259: 52 (1987)) and by Edge et al., (Anal. Biochem. 118: 131 (1981)). Enzymatic cleavage of carbohydrate moieties on antibodies can be achieved by the use of a variety of endo- and exo-glycosidases as described by Thotakura et al., (Meth. Enzymol. 138: 350 (1987)).

Another type of covalent modification of the antibody comprises linking the antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

Derivatives

As stated above, derivative refers to polypeptides chemically modified by such techniques as ubiquitination, labeling (e.g., with radionuclides or various enzymes), covalent polymer attachment such as PEGylation (derivatization with polyethylene glycol) and insertion or substitution by chemical synthesis of amino acids such as ornithine. Derivatives of the antibody substance of the invention, such as a bispecific antibody, are also useful as therapeutic agents and may be produced by the methods herein.

The conjugated moiety can be incorporated in or attached to an antibody substance either covalently, or through ionic, van der Waals or hydrogen bonds, e.g., incorporation of radioactive nucleotides, or biotinylated nucleotides that are recognized by streptavadin.

Polyethylene glycol (PEG) may be attached to the antibody substances to provide a longer half-life in vivo. The PEG group may be of any convenient molecular weight and may be linear or branched. The average molecular weight of the PEG will preferably range from about 2 kiloDalton ("kD") to about 100 kDa, more preferably from about 5 kDa to about 50 kDa, most preferably from about 5 kDa to about 10 kDa. The PEG groups will generally be attached to the antibody substances of the disclosure via acylation or reductive alkylation through a natural or engineered reactive group on the PEG moiety (e.g., an aldehyde, amino, thiol, or ester group) to a reactive group on the antibody substance (e.g., an aldehyde, amino, or ester group). Addition of PEG moieties to antibody substances can be carried out using techniques well-known in the art. See, e.g., International Publication No. WO 96/11953 and U.S. Pat. No. 4,179,337.

Ligation of the antibody substance with PEG usually takes place in aqueous phase and can be easily monitored by reverse phase analytical HPLC. The PEGylated substances are purified by preparative HPLC and characterized by analytical HPLC, amino acid analysis and laser desorption mass spectrometry.

Antibody Conjugates

An antibody may be administered in its "naked" or unconjugated form, or may be conjugated directly to other therapeutic or diagnostic agents, or may be conjugated indirectly to carrier polymers comprising such other therapeutic or diagnostic agents. In some embodiments the antibody is conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). Suitable chemotherapeutic agents include: daunomycin, doxorubicin, methotrexate, and vindesine (Rowland et al., (1986) supra). Suitable toxins include: bacterial toxins such as diphtheria toxin; plant toxins such as ricin; small molecule toxins such as geldanamycin (Mandler et al J. Natl. Cancer Inst. 92(19): 1573-81 (2000); Mandler et al., Bioorg. Med. Chem. Letters 10:1025-1028 (2000); Mandler et al., Bioconjugate Chem. 13.786-91 (2002)), maytansinoids (EP 1391213; Liu et al., Proc. Natl. Acad. Sci. USA 93:8618-23 (1996)), auristatins (Doronina et al., Nat. Biotech. 21: 778-84 (2003) and calicheamicin (Lode et al., Cancer Res. 58:2928 (1998); Hinman et al., Cancer Res. 53:3336-3342 (1993)).

Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

Conjugation of antibody moieties is described in U.S. Pat. No. 6,306,393. General techniques are also described in Shih et al., Int. J. Cancer 41:832-839 (1988); Shih et al., Int. J. Cancer 46:1101-1106 (1990); and Shih et al., U.S. Pat. No. 5,057,313. This general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate. Examples of agents to which the antibody can be conjugated include any of the cytotoxic or chemotherapeutic agents described herein.

Alternatively, conjugated antibodies can be prepared by directly conjugating an antibody component with a therapeutic agent. The general procedure is analogous to the indirect method of conjugation except that a therapeutic agent is directly attached to an oxidized antibody component. For example, a carbohydrate moiety of an antibody can be attached to polyethyleneglycol to extend half-life.

Alternatively, a therapeutic agent can be attached at the hinge region of a reduced antibody component via disulfide bond formation, or using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995). A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Antibody Fusion Proteins

Methods of making antibody fusion proteins are well known in the art. See, e.g., U.S. Pat. No. 6,306,393. Antibody fusion proteins comprising an interleukin-2 moiety are described by Boleti et al., Ann. Oncol. 6:945 (1995), Nicolet et al., Cancer Gene Ther. 2:161 (1995), Becker et al., Proc. Nat'l Acad. Sci. USA 93:7826 (1996), Hank et al., Clin. Cancer Res. 2:1951 (1996), and Hu et al., Cancer Res. 56:4998 (1996). In addition, Yang et al., (Hum. Antibodies Hybridomas 6:129 (1995)), describe a fusion protein that includes an F(ab')2 fragment and a tumor necrosis factor alpha moiety. Further examples of antibody fusion proteins are described by Pastan et al, Nat. Reviews Cancer 6: 559-65 (2006).

Methods of making antibody-toxin fusion proteins in which a recombinant molecule comprises one or more antibody components and a toxin or chemotherapeutic agent also are known to those of skill in the art. For example, antibody-*Pseudomonas* exotoxin A fusion proteins have been described by Chaudhary et al., Nature 339:394 (1989), Brinkmann et al., Proc. Nat'l Acad. Sci. USA 88:8616 (1991), Batra et al., Proc. Nat'l Acad. Sci. USA 89:5867 (1992), Friedman et al., J. Immunol. 150:3054 (1993), Wels et al., Int. J. Can. 60:137 (1995), Fominaya et al., J. Biol. Chem. 271:10560 (1996), Kuan et al., Biochemistry 35:2872 (1996), and Schmidt et al., Int. J. Can. 65:538 (1996). Antibody-toxin fusion proteins containing a diphtheria toxin moiety have been described by Kreitman et al., Leukemia 7:553 (1993), Nicholls et al., J. Biol. Chem. 268:5302 (1993), Thompson et al., J. Biol. Chem. 270: 28037 (1995), and Vallera et al., Blood 88:2342 (1996). Deonarain et al., Tumor Targeting 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., Apr. 2-6, 1995, Part 1, BIOT005. As a further example, Dohlsten et al., Proc. Nat'l Acad. Sci. USA 91:8945 (1994), reported an antibody-toxin fusion protein comprising Staphylococcal enterotoxin-A.

Illustrative of toxins which are suitably employed in the preparation of such fusion proteins are ricin, abrin, ribonuclease, DNase I, Staphylococcal enterotoxin-A, pokeweed antiviral protein, gelonin, diphtherin toxin, *Pseudomonas* exotoxin, and *Pseudomonas* endotoxin. See, for example, Pastan et al., Cell 47:641 (1986), and Goldenberg, C A—A Cancer Journal for Clinicians 44:43 (1994). Other suitable toxins are known to those of skill in the art.

Antibodies of the present disclosure may also be used in ADEPT by conjugating the antibody to a prodrug-activating enzyme which converts a prodrug (e.g., a peptidyl chemotherapeutic agent, See WO81/01145) to an active anti-cancer drug. See, for example, WO88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the present disclosure include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as α-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs of the disclosure into free active drugs (See, e.g., Massey, Nature 328: 457-458 (1987). Antibody-abzyme conjugates can be prepared as described herein for delivery of the abzyme to a tumor cell population.

The enzymes above can be covalently bound to the antibodies by techniques well known in the art such as the use of the heterobifunctional crosslinking reagents discussed above. Alternatively, fusion proteins comprising at least the antigen binding region of an antibody of the disclosure linked to at least a functionally active portion of an enzyme of the disclosure can be constructed using recombinant DNA techniques well known in the art (See, e.g., Neuberger et al., Nature 312:604-608 (1984))

Recombinant Production of Antibodies

DNA encoding an antibody of the present disclosure may be isolated and sequenced using conventional procedures (e.g., by using oligonucleotide probes that are capable of binding specifically to genes encoding the heavy and light chains of the antibodies). Usually this requires cloning the DNA or, preferably, mRNA (i.e., cDNA) encoding the antibodies. Cloning and sequencing is carried out using standard techniques, such as for example polymerase chain reaction (PCR), (see, e.g., Sambrook et al. (1989) Molecular Cloning: A Laboratory Guide, Vols 1-3, Cold Spring Harbor Press; Ausubel, et al. (Eds.), Protocols in Molecular Biology, John Wiley & Sons (1994)), which are incorporated herein by reference).

Nucleotide probe reactions and other nucleotide hybridization reactions are carried out at conditions enabling the identification of polynucleotides which hybridize to each other under specified conditions. One exemplary set of conditions is as follows: stringent hybridization at 42° C. in 50% formamide, 5×SSC, 20 mM Na.PO4, pH 6.8; and washing in 1×SSC at 55° C. for 30 minutes. Formula for calculating equivalent hybridization conditions and/or selecting other conditions to achieve a desired level of stringency are well known. It is understood in the art that conditions of equivalent stringency can be achieved through variation of temperature and buffer, or salt concentration as described Ausubel, et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51

As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

One source for RNA used for cloning and sequencing is a hybridoma produced by obtaining a B cell from the transgenic mouse and fusing the B cell to an immortal cell. An advantage of using hybridomas is that they can be easily screened, and a hybridoma that produces a human monoclonal antibody of interest selected. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described further herein and is also well-known in the art. See e.g., Dower et al., WO 91/17271, McCafferty et al., WO 92/01047, and Caton and Koprowski, (Proc. Natl. Acad. Sci. USA, 87:6450-54 (1990)), each of which is incorporated herein by reference. In one embodiment using phage display technology, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard techniques such as panning.

Typically the sequence encoding an entire variable region of the immunoglobulin polypeptide is determined, however, it will sometimes by adequate to sequence only a portion of a variable region, for example, the CDR-encoding portion. Typically the portion sequenced will be at least 30 bases in length, more often based coding for at least about one-third or at least about one-half of the length of the variable region will be sequenced.

Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be placed into expression vectors, which are then transfected into host cells such as *E. coli* cells, simian COS cells, human embryonic kidney 293 cells (e.g., 293E cells), Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art.

Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

In an alternative embodiment, the amino acid sequence of an immunoglobulin of interest may be determined by direct protein sequencing. Suitable encoding nucleotide sequences can be designed according to a universal codon table.

Amino acid sequence variants may be prepared by introducing appropriate nucleotide changes into the encoding DNA, or by peptide synthesis. Such variants include, for example, deletions from, and/or insertions into and/or substitutions of, residues within the amino acid sequences of the antibodies. Any combination of deletion, insertion, and substitution is made to arrive at the final construct, provided that the final construct possesses the desired characteristics. The amino acid changes also may alter post-translational processes of the molecule, such as changing the number or position of glycosylation sites.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

The present disclosure also provides isolated nucleic acid encoding antibodies of the disclosure, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium. Various systems and methods for antibody production are reviewed by Birch & Racher (Adv. Drug Deliv. Rev. 671-685 (2006)).

For recombinant production of the antibodies, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence.

(1) Signal Sequence Component

Antibodies of the present disclosure may be produced recombinantly not only directly, but also as a fusion polypeptide with a heterologous polypeptide, which is preferably a signal sequence or other polypeptide having a specific cleavage site at the N-terminus of the mature protein or polypeptide. The signal sequence selected preferably is one that is recognized and processed (i.e., cleaved by a signal peptidase) by the host cell. If prokaryotic host cells do not recognize and process the native antibody signal sequence, the signal sequence may be substituted by a signal sequence selected, for example, from the group of the pectate lyase (e.g., pelB) alkaline phosphatase, penicillinase, lpp, or heat-stable enterotoxin II leaders. For yeast secretion the native signal sequence may be substituted by, e.g., the yeast invertase leader, α factor leader (including *Saccharomyces* and *Kluyveromyces* α-factor leaders), or acid phosphatase leader, the *C. albicans* glucoamylase leader, or the signal described in WO90/13646. In mammalian cell expression, mammalian signal sequences as well as viral secretory leaders, for example, the herpes simplex gD signal, are available.

The DNA for such precursor region is ligated in reading frame to DNA encoding the antibody.

(2) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins are useful for cloning vectors in mammalian cells. Generally, the origin of replication component is not needed for mammalian expression vectors (the SV40 origin may typically be used only because it contains the early promoter).

(3) Selective Marker Component

Expression and cloning vectors may contain a selective gene, also termed a selectable marker. Typical selection genes encode proteins that (a) confer resistance to antibiotics or other toxins, e.g., ampicillin, neomycin, methotrexate, tetracycline, G418, geneticin, histidinol, or mycophenolic acid (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs methotrexate, neomycin, histidinol, puromycin, mycophenolic acid and hygromycin.

Another example of suitable selectable markers for mammalian cells are those that enable the identification of cells competent to take up the antibody-encoding nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody of the disclosure, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282: 39 (1979)). The trp1 gene provides a selection marker for a mutant strain of yeast lacking the ability to grow in tryptophan, for example, ATCC No. 44076 or PEP4-1. Jones, (Genetics 85:12 (1977)). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene. Ura3-deficient yeast strains are complemented by plasmids bearing the ura3 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* Van den Berg, (Bio/Technology, 8:135 (1990)). Stable multi-copy expression vectors for secretion of mature recombinant human serum albumin by industrial strains of *Kluyveromyces* have also been disclosed (Fleer et al, Bio/Technology, 9:968-975 (1991)).

(4) Promoter Component

Expression and cloning vectors usually contain a promoter that is recognized by the host organism and is operably linked to the antibody-encoding nucleic acid. Promoters suitable for use with prokaryotic hosts include the arabinose (e.g., araB) promoter phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody of the disclosure.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as Abelson leukemia virus, polyoma virus, fowlpox virus, adenovirus (such as Adenovirus 2), bovine papilloma virus, avian sarcoma virus, most preferably cytomegalovirus, a retrovirus, hepatitis-B virus, Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297: 598-601 (1982) on expression of human β-interferon cDNA in mouse cells under the control of a thymidine kinase promoter from herpes simplex virus. Alternatively, the rous sarcoma virus long terminal repeat can be used as the promoter.

(5) Enhancer Element Component

Transcription of a DNA encoding the antibody of this disclosure by higher eukaryotes is often increased by inserting an enhancer sequence into the vector. Many enhancer sequences are known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

(6) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein. Another is the mouse immunoglobulin light chain transcription terminator.

(7) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastors* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, petunia, tomato, tobacco, lemna, and other plant cells can also be utilized as hosts.

Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, (Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y Acad. Sci. 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies that bind target.

(8) Culturing the Host Cells

The host cells used to produce the antibody of this disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., (Meth. Enz. 58: 44, 1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(9) Purification of Antibody

When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. (Science 240:1041-43, 1988; ICSU Short Reports 10:105 (1990); and Proc. Natl. Acad. Sci. USA 90:457-461 (1993) describe a procedure for isolating antibodies which are secreted to the periplasmic space of *E. coli*. [See also, (Carter et al., Bio/Technology 10:163-167 (1992)].

The antibody composition prepared from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62: 1-13, 1983). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH 3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE® chromatography on an anion or cation exchange resin (such as a polyaspartic acid column), chromatofocusing, SDS-PAGE, and ammonium sulfate precipitation are also available depending on the antibody to be recovered.

Screening Methods

Effective therapeutics depend on identifying efficacious agents devoid of significant toxicity. Antibodies may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety.

In one embodiment of the present disclosure, methods of screening for antibodies which modulate the activity of a target antigen comprise contacting test antibodies with a target polypeptide and assaying for the presence of a complex between the antibody and the target ligand. In such assays, the ligand is typically labeled. After suitable incubation, free ligand is separated from that present in bound form, and the amount of free or uncomplexed label is a measure of the ability of the particular antibody to bind to the target ligand.

In another embodiment of the present disclosure, high throughput screening for antibody fragments or CDRs having suitable binding affinity to a target polypeptide is employed. Briefly, large numbers of different small peptide test compounds are synthesized on a solid substrate. The peptide test antibodies are contacted with a target polypeptide and washed. Bound polypeptides are then detected by methods well known in the art. Purified antibodies of the disclosure can also be coated directly onto plates for use in the aforementioned drug screening techniques. In addition, non-neutralizing antibodies can be used to capture the target and immobilize it on the solid support.

Methods for assessing neutralizing biological activity of TGFβ and anti-TGFβ antibodies are known in the art. See, e.g., U.S. Pat. No. 7,867,496. Examples of in vitro bioassays include: (1) induction of colony formation of NRK cells in soft agar in the presence of EGF (Roberts et al. (1981) Proc. Natl. Acad. Sci. USA, 78:5339-5343); (2) induction of differentiation of primitive mesenchymal cells to express a cartilaginous phenotype (Seyedin et al. (1985) Proc. Natl. Acad. Sci. USA, 82:2267-2271); (3) inhibition of growth of Mv1Lu mink lung epithelial cells (Danielpour et al. (1989) J. Cell. Physiol., 138:79-86) and BBC-1 monkey kidney cells (Holley et al. (1980) Proc. Natl. Acad. Sci. USA, 77:5989-5992); (4) inhibition of mitogenesis of C3H/HeJ mouse thymocytes (Wrann et al. (1987) EMBO J., 6:1633-1636); (5) inhibition of differentiation of rat L6 myoblast cells (Florini et al. (1986) J. Biol. Chem., 261:16509-16513); (6) measurement of fibronectin production (Wrana et al. (1992) Cell, 71:1003-1014); (7) induction of plasminogen activator inhibitor I (PAI-1) promoter fused to a luciferase reporter gene (Abe et al. (1994) Anal. Biochem., 216:276-284); (8) sandwich enzyme-linked immunosorbent assays (Danielpour et al. (1989) Growth Factors, 2:61-71); and (9) cellular assays described in Singh et al. (2003) Bioorg. Med. Chem. Lett., 13(24):4355-4359.

In some embodiments, antibody neutralization of TGFβ1 and TGFβ2 is at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% more potent that neutralization of TGFβ3.

Additional methods for assessing the biological activity and neutralization of TGFβ (e.g., by TGFβ antibodies) are provided in the Examples. For example, neutralization can be measured by neutralization assays and expressed as an IC50 value. The IC50 value can be calculated for a given molecule by determining the concentration of molecule needed to elicit half inhibition of the maximum biological response of a second molecule or cell activity. The lower the IC50, the greater the potency of the molecule to inhibit the desired protein activity. Exemplary neutralization assays contemplated herein include, but are not limited to, an interleukin-11 release assay and an HT-2/IL-4 cell proliferation assay. In addition, a TGFβ activity assay can be carried out to determine if the antibody inhibits one TGFβ isoform preferentially, including a pSMAD phosphorylation assay or an rhLAP binding assay. In a further embodiment, the antibody has a lower IC50 (i.e., better binding, greater potency) for TGFβ1 and TGFβ2 compared to TGFβ3.

Combination Therapy

In one embodiment, an antibody of the present disclosure is administered with a second agent useful to treat a disease or disorder as described herein. If more than one antibody effective at binding to target antigen is identified, it is contemplated that two or more antibodies to different epitopes of the target antigen and/or which bind preferentially to different isoforms of TGFβ may be mixed such that the combination of antibodies together to provide still improved efficacy against a condition or disorder associated with the target polypeptide. Compositions comprising one or more antibody of the invention may be administered to persons or mammals suffering from, or predisposed to suffer from, a condition or disorder to be treated associated with the target polypeptide.

Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

A second agent may be other therapeutic agents, such as cytokines, growth factors, antibodies to other target antigens, anti-inflammatory agents, anti-coagulant agents, agent that inhibit extracellular matrix production, agents that will lower or reduce blood pressure, agents that will reduce cholesterol, triglycerides, LDL, VLDL, or lipoprotein(a) or increase HDL, agents that will increase or decrease levels of cholesterol-regulating proteins, anti-neoplastic drugs or molecules. For patients with a hyperproliferative disorder, such as cancer or a tumor, combination with second therapeutic modalities such as radiotherapy, chemotherapy, photodynamic therapy, or surgery is also contemplated.

It is contemplated the antibody of the present disclosure and the second agent may be given simultaneously, in the same formulation. It is further contemplated that the agents are administered in a separate formulation and administered concurrently, with concurrently referring to agents given within 30 minutes of each other.

In another aspect, the second agent is administered prior to administration of the antibody composition. Prior administration refers to administration of the second agent within the range of one week prior to treatment with the antibody, up to 30 minutes before administration of the antibody. It is further contemplated that the second agent is administered subsequent to administration of the antibody composition. Subsequent administration is meant to describe administration from 30 minutes after antibody treatment up to one week after antibody administration.

It is further contemplated that other adjunct therapies may be administered, where appropriate. For example, the patient may also be administered an extracellular matrix degrading protein, surgical therapy, chemotherapy, a cytotoxic agent, or radiation therapy where appropriate.

It is further contemplated that when the antibody is administered in combination with a second agent, such as for example, wherein the second agent is a cytokine or growth factor, or a chemotherapeutic agent, the administration also includes use of a radiotherapeutic agent or radiation therapy. The radiation therapy administered in combination with an antibody composition is administered as determined by the treating physician, and at doses typically given to patients being treated for cancer.

A cytotoxic agent refers to a substance that inhibits or prevents the function of cells and/or causes destruction of cells. The term is intended to include radioactive isotopes (e.g., I131, I125, Y90 and Re186), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody according to the disclosure.

Chemotherapeutic agents contemplated for use with the antibodies of the present disclosure include, but are not limited to those listed in Table I:

TABLE I

| Alkylating agents | Natural products |
|---|---|
| Nitrogen mustards | Antimitotic drugs |
| mechlorethamine | Taxanes |
| cyclophosphamide | paclitaxel |
| ifosfamide | Vinca alkaloids |
| melphalan | vinblastine (VLB) |
| chlorambucil | vincristine |
| Nitrosoureas | vinorelbine |
| carmustine (BCNU) | Taxotere ® (docetaxel) |
| lomustine (CCNU) | estramustine |
| semustine (methyl-CCNU) | estramustine phosphate |
| Ethylenimine/Methyl-melamine | Epipodophylotoxins |
| thriethylenemelamine (TEM) | etoposide |
| triethylene thiophosphoramide | teniposide |
| (thiotepa) | Antibiotics |
| hexamethylmelamine | actimomycin D |
| (HMM, altretamine) | daunomycin (rubido-mycin) |
| Alkyl sulfonates | doxorubicin (adria-mycin) |
| busulfan | mitoxantroneidarubicin |
| Triazines | bleomycin |
| dacarbazine (DTIC) | splicamycin (mithramycin) |
| Antimetabolites | mitomycinC |
| Folic Acid analogs | dactinomycin |
| methotrexate | aphidicolin |
| Trimetrexate | Enzymes |
| Pemetrexed | L-asparaginase |
| (Multi-targeted antifolate) | L-arginase |
| Pyrimidine analogs | Radiosensitizers |
| 5-fluorouracil | metronidazole |
| fluorodeoxyuridine | misonidazole |
| gemcitabine | desmethylmisonidazole |
| cytosine arabinoside | pimonidazole |
| (AraC, cytarabine) | etanidazole |
| 5-azacytidine | nimorazole |
| 2,2'- difluorodeoxy-cytidine | RSU 1069 |
| Purine analogs | EO9 |
| 6-mercaptopurine | RB 6145 |
| 6-thioguanine | SR4233 |
| azathioprine | nicotinamide |
| 2'-deoxycoformycin | 5-bromodeozyuridine |
| (pentostatin) | 5-iododeoxyuridine |
| erythrohydroxynonyl-adenine (EHNA) | bromodeoxycytidine |
| fludarabine phosphate | Miscellaneous agents |
| 2-chlorodeoxyadenosine | Platinum coordination complexes |

TABLE I-continued

| Alkylating agents | Natural products |
|---|---|
| (cladribine, 2-CdA) | cisplatin |
| Type I Topoisomerase Inhibitors | Carboplatin |
| camptothecin | oxaliplatin |
| topotecan | Anthracenedione |
| irinotecan | mitoxantrone |
| Biological response modifiers | Substituted urea |
| G-CSF | hydroxyurea |
| GM-CSF | Methylhydrazine derivatives |
| Differentiation Agents | N-methylhydrazine (MIH) |
| retinoic acid derivatives | procarbazine |
| Hormones and antagonists | Adrenocortical suppressant |
| Adrenocorticosteroids/antagonists | mitotane (o,p'- DDD) |
| prednisone and equiv-alents | ainoglutethimide |
| dexamethasone | Cytokines |
| ainoglutethimide | interferon ($\alpha$, $\beta$, $\gamma$) |
| Progestins | interleukin-2 |
| hydroxyprogesterone caproate | Photosensitizers |
| medroxyprogesterone acetate | hematoporphyrin derivatives |
| megestrol acetate | Photofrin ® |
| Estrogens | benzoporphyrin derivatives |
| diethylstilbestrol | Npe6 |
| ethynyl estradiol/equivalents | tin etioporphyrin (SnET2) |
| Antiestrogen | pheoboride-a |
| tamoxifen | bacteriochlorophyll-a |
| Androgens | naphthalocyanines |
| testosterone propionate | phthalocyanines |
| fluoxymesterone/equivalents | zinc phthalocyanines |
| Antiandrogens | Radiation |
| flutamide | X-ray |
| gonadotropin-releasing | ultraviolet light |
| hormone analogs | gamma radiation |
| leuprolide | visible light |
| Nonsteroidal antiandrogens | infrared radiation |
| flutamide | microwave radiation |

It is also contemplated that the second agent is an anti-fibrotic agent. Exemplary anti-fibrotic agents include, but are not limited to, other agents that reduce the activity of transforming growth factor-beta (TGF-β) (including but not limited to GC-1008 (Genzyme/MedImmune); lerdelimumab (CAT-152; Trabio, Cambridge Antibody); metelimumab (CAT-192, Cambridge Antibody,); LY-2157299 (Eli Lilly); ACU-HTR-028 (Opko Health)) including antibodies that target one or more TGF-β isoforms, inhibitors of TGF-β receptor kinases TGFBR1 (ALK5) and TGFBR2, and modulators of post-receptor signaling pathways; chemokine receptor signaling; endothelin receptor antagonists including inhibitors that target both endothelin receptor A and B and those that selectively target endothelin receptor A (including but not limited to ambrisentan; avosentan; bosentan; clazosentan; darusentan; BQ-153; FR-139317, L-744453; macitentan; PD-145065; PD-156252; PD163610; PS-433540; S-0139; sitaxentan sodium; TBC-3711; zibotentan); agents that reduce the activity of connective tissue growth factor (CTGF) (including but not limited to FG-3019, FibroGen), and also including other CTGF-neutralizing antibodies; matrix metalloproteinase (MMP) inhibitors (including but not limited to MMPI-12, PUP-1 and tigapotide triflutate); agents that reduce the activity of epidermal growth factor receptor (EGFR) including but not limed to erlotinib, gefitinib, BMS-690514, cetuximab, antibodies targeting EGF receptor, inhibitors of EGF receptor kinase, and modulators of post-receptor signaling pathways; agents that reduce the activity of platelet derived growth factor (PDGF) (including but not limited to Imatinib mesylate (Novartis)) and also including PDGF neutralizing antibodies, antibodies targeting PDGF receptor (PDGFR), inhibitors of PDGFR kinase activity, and post-receptor signaling pathways; agents that reduce the activity of vascular endothelial growth factor (VEGF) (including but not limited to axitinib, bevacizumab, BIBF-1120, CDP-791, CT-322, IMC-18F1, PTC-299, and ramucirumab) and also including VEGF-neutralizing antibodies, antibodies targeting the VEGF receptor 1 (VEGFR1, Flt-1) and VEGF receptor 2 (VEGFR2, KDR), the soluble form of VEGFR1 (sFlt) and derivatives thereof which neutralize VEGF, and inhibitors of VEGF receptor kinase activity; inhibitors of multiple receptor kinases such as BIBF-1120 which inhibits receptor kinases for vascular endothelial growth factor, fibroblast growth factor, and platelet derived growth factor; agents that interfere with integrin function (including but not limited to STX-100 and IMGN-388) and also including integrin targeted antibodies; agents that interfere with the pro-fibrotic activities of IL-4 (including but not limited to AER-001, AMG-317, APG-201, and sIL-4Rα) and IL-13 (including but not limited to AER-001, AMG-317, anrukinzumab, CAT-354, cintredekin besudotox, MK-6105, QAX-576, SB-313, SL-102, and TNX-650) and also including neutralizing anti-bodies to either cytokine, antibodies that target IL-4 receptor or IL-13 receptor, the soluble form of IL-4 receptor or derivatives thereof that is reported to bind and neutralize both IL-4 and IL-13, chimeric proteins including all or part of IL-13 and a toxin particularly *pseudomonas* endotoxin, signaling though the JAK-STAT kinase pathway; agents that interfere with epithelial mesenchymal transition including inhibitors of mTor (including but not limited to AP-23573); agents that reduce levels of copper such as tetrathiomolybdate; agents that reduce oxidative stress including N-acetyl cysteine and tetrathiomolybdate; and interferon gamma. Also contemplated are agents that are inhibitors of phosphodiesterase 4 (PDE4) (including but not limited to Roflumilast); inhibitors of phosphodiesterase 5 (PDE5) (including but not limited to mirodenafil, PF-4480682, sildenafil citrate, SLx-2101, tadalafil, udenafil, UK-369003, vardenafil, and zaprinast); or modifiers of the arachidonic acid pathway including cyclooxygenase and 5-lipoxegenase inhibitors (including but not limited to Zileuton). Further contemplated are compounds that reduce tissue remodeling or fibrosis including prolyl hydrolase inhibitors (including but not limited to 1016548, CG-0089, FG-2216, FG-4497, FG-5615, FG-6513, fibrostatin A (Takeda), lufironil, P-1894B, and safironil) and peroxisome proliferator-activated receptor (PPAR)-gamma agonists. (including but not limited to pioglitazone and rosiglitazone).

Other specific anti-fibrotic agents contemplated include relaxin, pirfenidone, ufironil, surifonil, CAT-192, CAT-158; ambresentan, thelin; FG-3019, a CTGF antibody; anti-EGFR antibody; a EGFR kinase inhibitor; tarceva; gefitinib; PDGF antibody, PDGFR kinase inhibitor; gleevec; BIBF-1120, VEGF, FGF, and PDGF receptor inhibitor; anti-integrin antibody; IL-4 antibody; tetrathiomolybdate, a copper chelating agent; interferon-gamma; NAC, a cysteine prodrug; hepatocyte growth factor (HGF); KGF; angiotension receptor blockers, ACE inhibitors, rennin inhibitors; COX and LO inhibitors; Zileuton; monteleukast; avastin; statins; PDE5 inhibitors, such as sildenafil, udenafil, tadalafil, vardenafil, or zaprinast; rofumilast; etanercept (Enbrel); procoagulant; prostaglandins, such as PGE2, PRX-08066, a 5HT2B receptor antagonist; cintredekin besudotox, a chimeric human IL13 conjugated to a genetically engineered *Pseudomonas* exotoxin; roflumilast, a PDE4 inhibitor; FG-3019, an anti-connective tissue growth factor human monoclonal antibody; GC-1008, a TGF-β human monoclonal antibody; treprostinil, a prostacyclin analog; interferon-α; QAX-576, a IL13 modulator; WEB 2086, a PAF-receptor antagonist; imatinib mesylate; FG-1019; Suramin; Bosentan; IFN-1b; anti-IL-4; anti-IL-13; taurine, niacin, NF-κB antisense oligonucleotides; and nitric oxide synthase inhibitors.

Treatment of Disorders

In another embodiment, the present disclosure provides a method for inhibiting target activity by administering a target-specific antibody to a patient in need thereof. Any of the types of antibodies described herein may be used therapeutically. In exemplary embodiments, the target specific antibody is a human, chimeric or humanized antibody. In another exemplary embodiment, the target is human and the patient is a human patient. Alternatively, the patient may be a mammal that expresses a target protein that the target specific antibody cross-reacts with. The antibody may be administered to a non-human mammal expressing a target protein with which the antibody cross-reacts (i.e. a primate) for veterinary purposes or as an animal model of human disease. Such animal models may be useful for evaluating the therapeutic efficacy of target specific antibodies of the disclosure.

In one embodiment, the disclosure provides a method for treating a condition or disorder associated with TGF-β expression comprising administering to a subject in need thereof a therapeutically effective amount of an antibody or a pharmaceutical composition as described herein.

Exemplary conditions or disorders associated with TGFβ expression that can be treated with an antibody substance that binds TGFβ (e.g., antibodies of the present disclosure) include cancers, such as lung cancer, prostate cancer, breast cancer, hepatocellular cancer, esophageal cancer, colorectal cancer, pancreatic cancer, bladder cancer, kidney cancer, ovarian cancer, stomach cancer, fibrotic cancer, glioma, and melanoma, eye (e.g., ocular, optic, ophthalmic or ophthalmological) diseases, conditions or disorders, disease, conditions or disorders associated with fibrosis, e.g., fibroproliferative diseases, conditions or disorders, or diseases, conditions or disorders having an associated fibrosis.

Fibroproliferative diseases, conditions or disorders or diseases having an associated fibrosis include those that affect any organ or tissue in the body, including, but not limited to, the skin, lung, kidney, heart, brain and eye. Fibroproliferative diseases, conditions or disorders, or diseases having an associated fibrosis include, but are not limited to pulmonary fibrosis, idiopathic pulmonary fibrosis, peribronchiolar fibrosis, interstitial lung disease, chronic obstructive pulmonary disease (COPD), small airway disease (e.g., obstructive bronchiolitis), emphysema, adult or acute respiratory distress syndrome (ARDS), acute lung injury (ALI), pulmonary fibrosis due to infectious or toxic agents, kidney fibrosis, glomerulonephritis (GN) of all etiologies, e.g., mesangial proliferative GN, immune GN, and crescentic GN, glomerulosclerosis, tubulointerstitial injury, renal interstitial fibrosis, renal fibrosis and all causes of renal interstitial fibrosis, renal fibrosis resulting from complications of drug exposure, including cyclosporin treatment of transplant recipients, e.g. cyclosporin treatment, HIV-associated nephropathy, transplant necropathy, diabetic kidney disease (e.g., diabetic nephropathy), nephrogenic systemic fibrosis, diabetes, idiopathic retroperitoneal fibrosis, scleroderma, liver fibrosis, hepatic diseases associated with excessive scarring and progressive sclerosis, including liver cirrhosis due to all etiologies, disorders of the biliary tree, hepatic dysfunction attributable to infections, fibrocystic diseases, cardiovascular diseases, such as congestive heart failure; dilated cardiomyopathy, myocarditis, vascular stenosis, cardiac fibrosis (e.g., post-infarction cardiac fibrosis), post myocardial infarction, left ventricular hypertrophy, veno-occlusive disease, restenosis (e.g., post-angioplasty restenosis), arteriovenous graft failure, atherosclerosis, hypertension, hypertensive heart disease, cardiac hypertrophy, hypertrophic cardiomyopathy, heart failure, disease of the aorta, progressive systemic sclerosis, polymyositis, systemic lupus erythematosus, dermatomyositis, fascists, Raynaud's syndrome, rheumatoid arthritis, proliferative vitreoretinopathy, vitreoretinopathy of any etiology or fibrosis associated with ocular surgery such as treatment of glaucoma, retinal reattachment, cataract extraction, or drainage procedures of any kind, scarring in the cornea and conjunctiva, fibrosis in the corneal endothelium, alkali burn (e.g., alkali burn to the cornea), post-cataract surgery fibrosis of the lens capsule, excess scarring the tissue around the extraocular muscles in the strabismus surgery, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), post-retinal and glaucoma surgery, tractional retinal detachment in association with contraction of the tissue in diabetic retinopathy, Peyronie's disease, systemic sclerosis, post-spinal cord injury, osteoporosis, Camurati-Engelmann disease, Crohn's disease, scarring, Marfan syndrome, premature ovarian failure, Alzheimer's Disease and Parkinson's Disease, fibrosis due to surgical incisions or mechanical trauma, fibrosis associated with ocular surgery, and excessive or hypertrophic scar or keloid formation in the dermis occurring during wound healing resulting from trauma or surgical wounds.

Exemplary eye diseases (e.g., ocular, optic, ophthalmic or ophthalmological diseases), conditions or disorders, include but are not limited to, fibroproliferative disorders, fibrosis of the eye, ophthalmic fibroses, retinal dysfunction, fibrosis associated with retinal dysfunction, wet or dry macular degeneration, proliferative vitreoretinopathy, vitreoretinopathy of any etiology, fibrosis associated with ocular surgery such as treatment of glaucoma, retinal reattachment, cataract extraction, or drainage procedures of any kind, scarring in the cornea and conjunctiva, fibrosis in the corneal endothelium, alkali burn (e.g., alkali burn to the cornea), post-cataract surgery fibrosis of the lens capsule, excess scarring in the tissue around the extraocular muscles in the strabismus surgery, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), fibrosis associated with post-retinal and glaucoma surgery, tractional retinal detachment in association with contraction of the tissue in diabetic retinopathy.

Exemplary fibroproliferative diseases, conditions or disorders of the eye, fibrosis of the eye, ocular fibrosis or ophthalmic fibroses include, but are not limited to, proliferative vitreoretinopathy, vitreoretinopathy of any etiology, fibrosis associated with retinal dysfunction, fibrosis associated with wet or dry macular degeneration, fibrosis associated with ocular surgery such as treatment of glaucoma, retinal reattachment, cataract extraction, or drainage procedures of any kind, scarring in the cornea and conjunctiva, fibrosis in the corneal endothelium, fibrosis associated with alkali burn, post-cataract surgery fibrosis of the lens capsule, excess scarring the tissue around the extraocular muscles in the strabismus surgery, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), fibrosis associated with post-retinal and glaucoma surgery, tractional retinal detachment in association with contraction of the tissue in diabetic retinopathy.

In various embodiments, the fibroproliferative disease, condition, or disorders of the eye is selected from the group consisting of proliferative vitreoretinopathy, fibrosis associated with ocular surgery, post-cataract surgery fibrosis of the lens, fibrosis of the corneal stroma and alkali burn.

Exemplary cancers that can be treated with an antibody substance according to the present invention include cancers, such as lung cancer, prostate cancer, breast cancer, hepatocellular cancer, esophageal cancer, colorectal cancer, pancreatic cancer, bladder cancer, kidney cancer, ovarian cancer, stomach cancer, fibrotic cancer, glioma and melanoma.

It has been observed that many human tumors (deMartin et al., EMBO J., 6: 3673 (1987), Kuppner et al., Int. J. Cancer, 42: 562 (1988)) and many tumor cell lines (Derynck et al., Cancer Res., 47: 707 (1987), Roberts et al., Br. J. Cancer, 57: 594 (1988)) produce TGFβ and suggests a possible mechanism for those tumors to evade normal immunological surveillance.

TGFβ isoform expression in cancer is complex and variable with different combinations of TGFβ isoforms having different roles in particular cancers. TGFβ molecules can act both as tumor suppressors and tumor promoters. For example, deletion or downregulation of TGFβ signaling in animals can result in increased breast cancer, intestinal cancer, pancreatic cancer, colon cancer and squamous cell carcinoma, indicating the presence of TGFβ is important to prevent or slow tumor progression (Yang et al., Trends Immunol 31:220-27, 2010). However, overexpression of TGFβ is known to be pro-oncogenic and increased expression is detected in many tumor types (Yang et al., supra)

Additional complexities are also disclosed in U.S. Pat. No. 7,927,593. For example, different TGFβ isoforms appear to be more relevant to different types of cancers. TGFβ1 and TGFβ3 may play a greater role in ovarian cancer and its progression than TGFβ2; while TGFβ1 and TGFβ2 expression is greater in higher grade chondrosarcoma tumors than TGFβ3. In human breast cancer, TGFβ1 and TGFβ3 are highly expressed, with TGFβ3 expression correlating with overall survival, whereas patients with node metastasis and positive TGFβ3 expression have poor prognostic outcomes. However, in colon cancer, TGFβ1 and TGFβ2 are more highly expressed than TGFβ3 and are present at greater circulating levels than in cancer-free individuals. In gliomas, TGFβ2 is important for cell migration. From the recent studies, it is not apparent which TGFβ isoforms would most useful to inhibit in a particular cancer and to what degree.

Infiltration of immune cells into tumor sites is thought to be a common contributing factor to tumor growth. These immune cell infiltrates can have a beneficial effect by helping to clear the tumor, but can also be detrimental effect by enabling tolerance to tumor antigens. It has been shown that TGFβ can affect levels of immune cells in tumors (see e.g., Yang et al., Trends Immunol 31:220-27, 2010; Flavell et al., Nature Immunol 10:554-567, 2010; Nagarau et al., Expert Opin Investig Drugs 19:77-91, 2010). For example, TGFβ suppresses natural killer cells that infiltrate tumors in order to clear tumors from the body. TGFβ also suppresses activity of cytotoxic T cells and CD4+ helper T cells, cell types which assist in clearance of tumors (Yang, supra). TGFβ also plays a role in regulating dendritic cell activity, for example by inhibiting migration into injury sites and presentation of antigen to promote an immune response. Dendritic cells are both responsive to TGFβ and secrete TGFβ. For example, dendritic cells infiltrate tumors and take up the cells, secrete TGFβ and activate regulatory T cells, which in turn can prevent tumor clearance (Flavell et al., supra). Additionally, myeloid derived suppressor cells (MDSC) are a bone marrow derived cells that expand during tumor progression. MDSC inhibit T cell proliferation, suppress dendritic cell maturation, and inhibit natural killer cell activity, thereby helping cells to evade the immune response (Li et al., J Immunol. 182:240-49, 2009). TGFβ has been demonstrated to contribute to the effects of MDSC on inhibiting natural killer cell activity (Li et al., supra; Xiang et al., Int J Cancer 124:2621-33, 2009). The role of the various TGFβ isoforms in each of these immune processes is unclear. Selectively targeting TGFβ isoforms and inhibiting them to varying degrees may be instrumental in modulating the host immune response to combat and clear the tumor.

In certain embodiments, the antibody or composition described herein modulates immune cells in a tumor. In some embodiments, the antibody or composition increases the number of natural killer (NK) cells in a tumor and/or increases cytolytic activity of NK cells. In various embodiments, the, the antibody or composition described herein decreases the number of regulatory T cells in a tumor and/or inhibits regulatory T cell function. For example, in various embodiments, the antibody or composition described herein inhibits inhibits ability of Tregs to down-regulate an immune response or to migrate to a site of an immune response.

In various embodiments, the antibody or composition described herein cytotoxic T cells in a tumor, and/or enhances CTL activity, e.g., boosts, increases or promotes CTL activity. For example, in various embodiments, the antibody or composition described herein increases perforin and granzyme production by CTL and increases cytolytic activity of the CTL.

In various embodiments, the antibody or composition described herein decreases the number of monocyte-derived stem cells (MDSC) in a tumor and/or inhibits MDSC function. For example, in various embodiments, the antibody or composition described herein inhibits the ability of MDSCs to suppress an immune response, inhibits immune suppressive activity of MDSCs, and/or inhibits the ability of MDSCs to promote expansion and/or function of Tregs.

In various embodiments, the, the antibody or composition described herein decreases the number of dendritic cells (DC) in a tumor, and/or inhibits the tolerogenic function (e.g., tolerogenic effect) of dendritic cells. For example, in various embodiments, the antibody or composition described herein decreases the toleragenic effect of CD8+ dendritic cells.

In various embodiments, any of antibodies XPA.42.068, XPA.42.089 or XPA.42.681 or variants thereof as described herein modulate one or more of the immune activities described above.

As stated previously, TGFβ expression has also been implicated in the onset of various tissue fibroses, such as nephrosclerosis, pulmonary fibrosis and cirrhosis; as well as the onset of various states, such as chronic hepatitis, rheumatoid arthritis, vascular restenosis, and keloid of skin. In some exemplary embodiments, the antibodies described herein are used to treat fibrosis or a fibrotic condition. Exemplary fibrosis or fibrotic diseases includes, but are not limited to, glomerulonephritis, adult or acute respiratory distress syndrome (ARDS), diabetes, diabetic kidney disease, liver fibrosis, kidney fibrosis, lung fibrosis, post infarction cardiac fibrosis, fibrocystic diseases, fibrotic cancer, post myocardial infarction, left ventricular hypertrophy, pulmonary fibrosis, liver cirrhosis, veno-occlusive disease, post-spinal cord injury, post-retinal and glaucoma surgery, post-angioplasty restenosis, renal interstitial fibrosis, arteriovenous graft failure and scarring.

In one embodiment, treatment of these disorders or conditions in an animal in need of said treatment, comprises administering to the animal an effective amount of an antibody or a composition comprising an antibody described herein.

The conditions treatable by methods of the present disclosure preferably occur in mammals. Mammals include, for example, humans and other primates, as well as pet or companion animals such as dogs and cats, laboratory animals such as rats, mice and rabbits, and farm animals such as horses, pigs, sheep, and cattle.

Non-Therapeutic Uses

The antibodies of the present disclosure may be used as affinity purification agents for target or in diagnostic assays for target protein, e.g., detecting its expression in specific cells, tissues, or serum. The antibodies may also be used for in vivo diagnostic assays. Generally, for these purposes the antibody is labeled with a radionuclide (such as $^{111}$In, $^{99}$Tc, $^{14}$C, $^{131}$I, $^{125}$I, $^3$H, $^{32}$P or $^{35}$S) so that the antibody can be localized using immunoscintiography.

The antibodies of the present disclosure may be employed in any known assay method, such as competitive binding assays, direct and indirect sandwich assays, such as ELISAs, and immunoprecipitation assays. Zola, Monoclonal Antibodies: A Manual of Techniques, pp. 147-158 (CRC Press, Inc. 1987). The antibodies may also be used for immunohistochemistry, to label tissue or cell samples using methods known in the art.

The target specific antibodies can be used in a conventional immunoassay, including, without limitation, an ELISA, an RIA, FACS, tissue immunohistochemistry, Western blot or immunoprecipitation, which are all techniques well-known in the art. The antibodies of the disclosure can be used to detect target in humans and other mammals. The present disclosure provides a method for detecting target in a biological sample comprising contacting a biological sample with a target specific antibody of the disclosure and detecting the bound antibody. In one embodiment, the target specific antibody is directly labeled with a detectable label. In another embodiment, the target specific antibody (the first antibody) is unlabeled and a second antibody or other molecule that can bind the target specific antibody is labeled. As is well known to one of skill in the art, a second antibody is chosen that is able to specifically bind the particular species and class of the first antibody. For example, if the target specific antibody is a human IgG, then the secondary antibody could be an anti-human-IgG. Other molecules that can bind to antibodies include, without limitation, Protein A and Protein G, both of which are available commercially, e.g., from Pierce Chemical Co.

It is contemplated that the immunoassays disclosed above are used for a number of purposes. For example, the target specific antibodies can be used to detect target in cells or on the surface of cells in cell culture, or secreted into the tissue culture medium. The target specific antibodies can be used to determine the amount of target on the surface of cells or secreted into the tissue culture medium that have been treated with various compounds. This method can be used to identify compounds that are useful to inhibit or activate target expression or secretion. According to this method, one sample of cells is treated with a test compound for a period of time while another sample is left untreated. If the total level of target is to be measured, the cells are lysed and the total target level is measured using one of the immunoassays described above. The total level of target in the treated versus the untreated cells is compared to determine the effect of the test compound.

Labels

In some embodiments, the antibody substance is labeled to facilitate its detection. A "label" or a "detectable moiety" is a composition detectable by spectroscopic, photochemical, biochemical, immunochemical, chemical, or other physical means. For example, labels suitable for use in the present disclosure include, radioactive labels (e.g., 32P), fluorophores (e.g., fluorescein), electron dense reagents, enzymes (e.g., as commonly used in an ELISA), biotin, digoxigenin, or haptens as well as proteins which can be made detectable, e.g., by incorporating a radiolabel into the hapten or peptide, or used to detect antibodies specifically reactive with the hapten or peptide.

Examples of labels suitable for use in the present invention include, but are not limited to, fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold, colored glass or plastic beads (e.g., polystyrene, polypropylene, latex, etc.).

The label may be coupled directly or indirectly to the desired component of the assay according to methods well known in the art. Preferably, the label in one embodiment is covalently bound to the biopolymer using an isocyanate reagent for conjugation of an active agent according to the disclosure. In one aspect of the present disclosure, the bifunctional isocyanate reagents of the disclosure can be used to conjugate a label to a biopolymer to form a label biopolymer conjugate without an active agent attached thereto. The label biopolymer conjugate may be used as an intermediate for the synthesis of a labeled conjugate according to the disclosure or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The compounds of the present disclosure can also be conjugated directly to signal-generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present disclosure, see U.S. Pat. No. 4,391,904.

Means for detecting labels are well known to those of skill in the art. Thus, for example, where the label is radioactive, means for detection include a scintillation counter or photographic film, as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present disclosure will be readily apparent to those of skill in the art. Such labeled modulators and ligands can be used in the diagnosis of a disease or health condition.

Formulation of Pharmaceutical Compositions

To administer antibody substances of the present disclosure to human or test animals, it is preferable to formulate the antibody substances in a composition comprising one or more pharmaceutically acceptable carriers. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

In addition, compounds may form solvates with water or common organic solvents. Such solvates are contemplated as well.

The antibody is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the antibody is suitably administered by pulse infusion, particularly with declining doses of the antibody. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. Injection, especially intravenous, is preferred.

Pharmaceutical compositions of the present disclosure containing an antibody substance of the disclosure as an active ingredient may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present disclosure.

Formulation of the pharmaceutical composition will vary according to the route of administration selected (e.g., solution, emulsion). An appropriate composition comprising the antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

The antibodies of the present disclosure can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

The concentration of antibody in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 ml sterile buffered water, and 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of antibody is within the range of 0.01 mg to 1000 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancers include for example, salicylate, glycocholate/linoleate, glycholate, aprotinin, bacitracin, SDS, caprate and the like. See, e.g., Fix (J. Pharm. Sci., 85:1282-1285 (1996)) and Oliyai and Stella (Ann. Rev. Pharmacol. Toxicol., 32:521-544 (1993)).

Antibody compositions contemplated for use to inhibit target activity, including binding of the target to its cognate receptor or ligand, target-mediated signaling, and the like. In particular, the compositions exhibit inhibitory properties at concentrations that are substantially free of side effects, and are therefore useful for extended treatment protocols. For example, co-administration of an antibody composition with another, more toxic, cytotoxic agent can achieve beneficial inhibition of a condition or disorder being treated, while effectively reducing the toxic side effects in the patient.

In addition, the properties of hydrophilicity and hydrophobicity of the compositions contemplated for use in the present disclosure are well balanced, thereby enhancing their utility for both in vitro and especially in vivo uses, while other compositions lacking such balance are of substantially less utility. Specifically, compositions contemplated for use in the disclosure have an appropriate degree of solubility in aqueous media which permits absorption and bioavailability in the body, while also having a degree of solubility in lipids which permits the compounds to traverse the cell membrane to a putative site of action. Thus, antibody compositions contemplated are maximally effective when they can be delivered to the site of target antigen activity.

Administration and Dosing

In one aspect, methods of the present disclosure include a step of administering a pharmaceutical composition. In certain embodiments, the pharmaceutical composition is a sterile composition.

Methods of the present disclosure are performed using any medically-accepted means for introducing a therapeutic directly or indirectly into a mammalian subject, including but not limited to injections, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by, intradermal, intramammary, intraperitoneal, intrathecal, retrobulbar, intrapulmonary injection and or surgical implantation at a particular site is contemplated as well.

In one embodiment, administration is performed at the site of a cancer, fibrosis or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the disclosure implanted near or at site of the cancer, fibrosis or affected tissue or organ.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, weekly, every 2 weeks, every 3 weeks, monthly, or at a longer interval.

Also contemplated in the present disclosure is the administration of multiple agents, such as an antibody composition in conjunction with a second agent as described herein, including but not limited to a chemotherapeutic agent or an agent useful to treat fibrosis.

The amounts of antibody composition in a given dosage may vary according to the size of the individual to whom the therapy is being administered as well as the characteristics of the disorder being treated. In exemplary treatments, it may be necessary to administer about 1 mg/day, 5 mg/day, 10 mg/day, 20 mg/day, 50 mg/day, 75 mg/day, 100 mg/day, 150 mg/day, 200 mg/day, 250 mg/day, 500 mg/day or 1000 mg/day. These concentrations may be administered as a single dosage form or as multiple doses. Standard dose-response studies, first in animal models and then in clinical testing, reveal optimal dosages for particular disease states and patient populations.

It will also be apparent that dosing may be modified if traditional therapeutics are administered in combination with therapeutics of the disclosure.

Kits

As an additional aspect, the disclosure includes kits which comprise one or more compounds or compositions packaged in a manner which facilitates their use to practice methods of the disclosure. In one embodiment, such a kit includes a compound or composition described herein (e.g., a composition comprising a target-specific antibody alone or in combination with a second agent), packaged in a container such as a sealed bottle or vessel, with a label affixed to the container or included in the package that describes use of the compound or composition in practicing the method. Preferably, the compound or composition is packaged in a unit dosage form. The kit may further include a device suitable for administering the composition according to a specific route of administration or for practicing a screening assay. Preferably, the kit contains a label that describes use of the antibody composition.

Additional aspects and details of the disclosure will be apparent from the following examples, which are intended to be illustrative rather than limiting.

EXAMPLES

Example 1. Isolation of Anti-TGFβ Antibodies from Antibody Phage Display Libraries To isolate a panel of antibodies able to neutralize the activity of human TGFβ, three isoforms of the TGFβ protein, TGFβ1, TGFβ2 and TGFβ3 were used for panning of human antibody phage display libraries as described below.

Panning:

The TGFβ antigens (PeproTech, Rocky Hill, N.J. #100-21, 100-35B, 100-36E) were first prepared by biotinylating with NHS-PEG4-Biotin (Pierce, Rockford, Ill.) using the manufacturer's protocol. Briefly, the TGFβ antigens, which were stored in low pH buffer, were neutralized by addition of 20×PBS to bring pH to roughly 6.0. A 30-fold molar excess of the above pre-activated biotin was added and mixed, then kept at room temperature for 20 minutes. Then equal volume of 10 mM Glycine pH 3.0 was added and the samples were put immediately into dialysis using a 6-8 kDa cut-off dialysis unit against a 10 mM Citrate buffer, pH 3.5. A Fab phage display library (XOMA, Berkeley, Calif.) was panned with the biotinylated TGFβ using a soluble panning method. Each TGFβ isoform was panned separately in three selection rounds. Kappa and lambda sublibraries were panned separately.

For the first round of phage panning, 50× library equivalents (~2×10$^{12}$ cfu) of the library was blocked on ice for 1 hr in 1 mL of 5% milk/PBS. Binders to streptavidin were deselected from blocked phage by adding blocked phage to streptavidin-coated magnetic DYNABEADS® M-280 and incubating with rotation for 30 minutes. The deselection step was repeated once more. A magnet was used to separate beads from phage. Concurrent to the deselection steps, 200 pmoles of biotinylated TGFβ was allowed to bind streptavidin-coated magnetic DYNABEADS® M-280 by incubating at room temperature with rotation for 30 minutes. After binding, the biotinylated TGFβ beads were washed twice with 5% Milk-PBS. Selection was done by adding deselected phage to biotinylated TGFβ bound to magnetic streptavidin beads and incubating with rotation for 1.5 to 2 hours. After selection, unbound phage was washed from beads using a Kingfisher magnetic particle processor (Thermo Scientific) which was programmed to wash beads quickly 3 times with PBS-0.1% TWEEN followed by an additional 3 quick washes with PBS. Bound phage was eluted from beads after the wash step by the addition of 100 mM triethylamine and incubating with rotation at room temperature for 30 minutes. Eluted phage was neutralized with the addition of equal volume 1M Tris-HCl, pH 7.4. Eluted neutralized phage was then collected into a 50 mL Falcon tube (Falcon No 352070) and used to infect log growing TG1 bacterial cells (OD$_{600}$~0.5). Infection was at 37° C. for 30 min without shaking, followed by 30 min additional incubation at 37° C. with shaking at 90 rpm. Cells were plated on 2YT media supplemented with 100 ug/mL Carbenicillin and 2% Glucose (2YTCG) agar bioassay plates and incubated overnight at 30° C. to allow for overnight lawn growth.

In preparation for use as input for the next round, 100× of previous round output was rescued by superinfection using MK07 helper phage. This was done by inoculating 2YTCG media with cells scraped from previous panning round output. $OD_{600\ nm}$ was measured for starting culture and adjusted to reflect a starting $OD_{600\ nm}$ of ~0.05. Cells were grown at 37° C. with shaking until cells reached log-growing phase of $OD_{600\ nm}$~0.5. Cells were infected with MK07 (New England Biolabs, MA) at a multiplicity of infection (MOI)=~20, at 37° C. for 30 min without shaking, followed by an additional 30 min incubation at 37° C. with shaking at 150 rpm. After infection at 37° C., cells were pelleted and transferred to new 2YT media supplemented with 50 ug/mL Kanamycin and 100 ug/mL Carbenicillin (2YTCK). Cultures were grown overnight at 25° C. Phage was separated from cells and debris by centrifugation and resulting supernatant was recovered and used as input for the next panning round. Selection enrichment was monitored by the amount of input used for each panning round and the resulting phage output titer.

For the second and third panning rounds, the same solution phase protocols followed in round one were used with the following exceptions. Phage input amount used in panning rounds two and three was ~$1.0 \times 10^{11}$ cfu. For round two, 100 pmoles of biotinylated antigen was used in selection, and for round three, 50 pmoles of biotinylated antigen was used. The Kingfisher was used to wash unbound phage from beads after selections. In round two, the Kingfisher was programmed to wash beads 3 times with PBS-0.1% TWEEN for 2 minutes followed by 1 ml PBS wash for 2 minutes repeated 3 times. In round three panning, beads were washed 3 times with PBS-0.1% TWEEN for 6 minutes, followed by two four minute washes and one six minute wash with PBS.

Bacterial periplasmic extracts containing secreted antibody fragments for use in screening for TGFβ binders were prepared by standard methods. Individual colonies were picked into 96 well plates filled with 2YTC supplemented with 100 ug/mL Carbenicillin and 0.1% glucose media. Cultures were allowed to grow at 37° C. with shaking until log growing phase was reached ($OD_{600\ nm}$=0.5). Colonies were then induced to produce soluble fragment antibodies by adding 1 mM IPTG final and incubated overnight at 25° C. with shaking. Periplasmic extracts (PPE) containing soluble fragment antibodies were prepared from the induced cells using the standard method of adding 1:3 volume ratio of ice-cold PPB solution (Teknova, Hollister, Calif.) and double distilled water ($ddH_2O$) with complete EDTA free protease inhibitor cocktail tablets. PPE were then used to screen for TGF-β binders.

Screening:

Two alternative screening assay formats were used to identify clones that bound TGFβ, including clones that bound to all three TGFβ isoforms and were unique in their sequences. The first screening assay used a plate-based immune-assay and the other screening assay was performed using an SPR screening method. The plate-based assay involved coating opaque 384 well white EIA plates with 1 ug/mL Anti-His antibody clone AD.1.10 (R&D Systems, Minneapolis, Minn.) at 1 ug/mL in PBS buffer for four hours at room temperature. Then the plate was washed 3× in PBS-TWEEN and then blocked with 0.5% BSA in PBS-TWEEN for 1 hour at room temperature. Next 30 uL/well of biotinylated TGFβ was added at between 0.1 ug/mL for TGFβ1 and TGFβ2, and 0.2 ug/mL for TGFβ3, diluted in blocking buffer. Then 30 uL of periplasmic extract was added and incubated at 4° C. overnight on gentle plate shaker. Plates were washed 3× in PBS-TWEEN then added 50 uL/well of 2.5 ug/mL Streptavidin-Europium (SA-Eu, PerkinElmer) diluted in DELFIA assay dilution buffer (PerkinElmer) to each well and incubated at room temp for 30 minutes on a shaker. Plates were washed 7 times with PBS-TWEEN and added 50 uL/well of the DELFIA enhancement reagent (PerkinElmer) and put on shaker for 8 minutes at room temperature then read on Molecular Devices FlexStation 3 plate reader in TRF mode with 200-1200 μs collection time and Exc.=345 nm, Emm.=618 nm, and cutoff=590 nm, High PMT setting, 20 Reads/well. Samples with signal of more than 2.1-fold higher signal than negative PPE control were considered to be positive.

The SPR assay was performed by a BIACORE A100 direct binding assay. In this assay, a CM5 BIACORE chip was prepared via standard amine coupling chemistry using the BIACORE Amine Coupling kit (GE Healthcare, Piscataway, N.J.). The TGFβ antigens were diluted to 6 ug/mL in acetate pH 4.0 and injected for 7 minutes (spots 1, which is TGFβ1) and 10 minutes (spots 2 and 4, which are TGFβ2, and TGFβ3). This immobilizes between 3400 and 4800 RU of each TGFβ antigen. Samples were deactivated with 1M ethanolamine. Periplasmic extracts were diluted 1:1 with HBS-EP+ (Teknova) with 2 mg/mL BSA and filtered through a 0.2 uM Millex GV filterplate (Millipore) and then injected at 30 uL/minute for 240 seconds with a 30 second dissociation. Regeneration after each PPE injection was 10 seconds of 100 mM HCl. The stability early report point in the BIACORE A100 software was used to evaluate PPE binding levels. Cut-off levels were determined for each TGFβ isoform independently as being visually above background level. RU cutoffs were 245, 175, and 125 for TGFβ1, TGFβ2 and TGFβ3, respectively.

Affinity Maturation:

One antibody, XPA.42.068, which had significantly greater binding and neutralizing activity for TGFβ1 and TGFβ2 relative to TGFβ3, was subjected to affinity maturation to increase its affinity and potency against TGFβ3. A library of sequence variants generated from affinity maturation was panned using TGFβ2 and TGFβ3, with output clones screened primarily for improved TGFβ3 binding.

For screening, the SPR assay was performed by a BIACORE A100 direct binding assay. In this assay a CM5 BIACORE chip was prepared via standard amine coupling chemistry using the BIACORE Amine Coupling kit. The TGFβ antigens were diluted to 1 ug/mL in acetate pH4.0 and injected for 5 minutes (spots 1 and 5, which are TGFβ3 and TGFβ1 respectively) and 8 minutes (spots 2, which is TGFβ2). This immobilizes between 200 and 450 RU of each TGFβ. Samples were deactivated with 1M ethanolamine. Periplasmic extracts were diluted 1:1 with HBS-EP+ with 2 mg/mL BSA and filtered through a 0.2 μm Millex GV filter plate (Millipore) and then injected at 30 uL/minute for 240 seconds with a 600 second dissociation. Regeneration after each PPE injection was 10 seconds of 100 mM HCl. Reference subtracted data was plotted and examined visually for clones that appeared to have either greater stability or higher binding levels. One derivative clone, designated XPA.42.681, which demonstrated enhanced binding to TGFβ3, was included in further characterization studies.

Selected clones were reformatted as IgG2 antibodies. The variable heavy (VH) and light (VL) chains of the selected Fab fragments were PCR-amplified, cloned into plasmid vectors containing antibody constant region sequences, and transiently transfected into 293E cells using standard methods to generate material for further characterization, including the studies described below.

Example 2. Measurement of Binding Affinities of TGFβ Antibodies

Antibodies were characterized against TGFβ isoforms TGFβ1, TGFβ2, and TGFβ3 for their binding affinity (KD), off-rate (kd) and on-rate (ka) using surface plasmon resonance (SPR) technology. The analysis was performed using two methods. One method was an antigen direct immobilization method in which the TGFβ proteins were immobilized to a surface at low density with the antibodies injected at multiple concentrations for kinetic analysis. The other method was an immobilized antibody method using injections of various concentrations of injected TGFβ proteins.

Immobilized Antibody Kinetics Method:

A CM4 sensor chip (GE Healthcare) was used on a BIACORE 2000 system (GE Healthcare). The chip was preconditioned with two 30 second injections each at 50 μL/minute flow rate of 100 mM HCl, Glycine pH 2.0, 50 mM NaOH, and running buffer prior to immobilization. Running buffer for immobilization was a HEPES Buffered Saline (HBS-EP+) with 10 mM Hepes, 150 mM Sodium Chloride, 3 mM EDTA, and 0.05% Polysorbate 20 (Teknova). The chip surface was activated with a seven minute injection at 10 μL/minute of a freshly mixed 1:1 solution of 0.1 M N-Hydroxysuccinimide (NHS) and 0.4 M 1-Ethyl-3-(3-dimethylaminopropyl) carbodiimide hydrochloride (EDC). Following the activation injection, 1 ug/mL anti-TGFβ antibody in acetate pH 4.5 was injected at 10 μL/minute for one minute, with injections targeting 120 RU. 8 minutes of 1M Ethanolamine hydrochloride-NaOH pH 8.5 was injected to block the surface. The NHS, EDC, and Ethanolamine used were from the BIACORE Amine Coupling Kit.

Kinetic Analysis was performed using a running buffer of thoroughly degassed form of the HBS-EP+ buffer above supplemented with 1 mg/mL BSA (Sigma Aldrich, St. Louis Mo.). TGFβ sample injections were performed at 50 μL/minute for four minutes with a 900 second dissociation time. Each TGFβ protein (TGFβ1, TGFβ2, TGFβ3) was injected at 10 nM, 2 nM, 0.4 nM, 0.08 nM (350 ng/mL with 5 fold serial dilution) with blanks bracketing each concentration series and quadruplicate injections. Regeneration was then performed with three injections of 30 seconds each of 100 mM HCl in 3 M MgCl$_2$ followed by a final 30 second blank buffer injection.

The data were analyzed using Scrubber2 (BioLogic Software, Campbell Australia) and was double referenced by subtracting both the blank flow cell data and the averaged bracketing blank injections. The data was fit by simultaneously fitting the (KD) an off-rate (kd) and on-rate (ka), and are shown in Table 2 below. Data for a previously measured comparator antibody, designated BM-1 (1D11, R&D Systems MAB1835) also are included in Table 2. BM-1 data was generated on the BIACORE A100. Briefly the BM-1 antibody was captured at approximately 100 RU density on a high density Rabbit anti-mouse Fc CM5 chip surface (GE Healthcare). TGFβ proteins were injected at the same concentrations as described above at 30 μL/minute. These data were double referenced and analyzed in BIACORE A100 software.

TABLE 2

Affinity data from assay utilizing immobilized antibody and injected TGFβ

| Antibody | TGFβ1 | | | TGFβ2 | | | TGFβ3 | | |
|---|---|---|---|---|---|---|---|---|---|
| | ka (1/Ms) | kd (1/s) | KD | ka (1/Ms) | kd (1/s) | KD | ka (1/Ms) | kd (1/s) | KD |
| XPA.42.068 | 1.53E+07 | 9.05E−04 | 59 pM | 1.04E+07 | 5.35E−04 | 51 pM | 8.45E+06 | 3.84E−03 | 455 pM |
| XPA.42.089 | 4.40E+07 | 1.67E−04 | 3.8 pM | 1.62E+07 | 4.14E−04 | 25 pM | 7.70E+06 | 1.09E−02 | 1.4 nM |
| XPA.42.681 | 4.25E+07 | 7.20E−05 | 1.7 pM | 1.71E+07 | 4.99E−05 | 2.9 pM | 1.30E+07 | 7.50E−05 | 5.7 pM |
| BM-1 | 1.90E+07 | 1.40E−03 | 72 pM | 1.10E+07 | 2.00E−03 | 170 pM | 6.50E+06 | 3.10E−04 | 48 pM |

The affinity data as measured in this assay using immobilized antibodies showed that XPA.42.681 had the strongest (tightest) binding of any of the antibodies for each of the three isoforms of TGFβ, and also bound each of the TGFβ isoforms with similar affinities. In addition, the antibodies XPA.42.068 and XPA.42.089 had similar or stronger binding to the TGFβ1 and TGFβ2 isoforms compared with the BM-1 antibody, but showed significantly less binding to the TGFβ3 isoform, compared either to the BM-1 antibody or relative to TGFβ1 and TGFβ2 binding.

Immobilized TGFβ Affinity Method:

A CM1 sensor chip (GE Healthcare) which has a planar —COOH surface was used on a BIACORE 2000 system. The chip was preconditioned with two 30 second injections each at 50 μL/minute flow rate of 100 mM HCl, Glycine pH 2.0, 50 mM NaOH, 1% SDS, and running buffer prior to immobilization. Running buffer for immobilization was a HEPES Buffered Saline (HBS-EP+) with 10 mM Hepes, 150 mM Sodium Chloride, 3 mM EDTA, and 0.05% Polysorbate 20. The chip surface was activated with four minute injections at 20 μL/minute of a freshly mixed 1:1 solution of 0.1M N-Hydroxysuccinimide (NHS) and 0.4M 1-Ethyl-3-(3-dimethylaminopropyl) carbodiimide hydrochloride (EDC). Following the activation injection a 0.1 ug/mL solution of TGFβ in acetate pH 4.0 was injected at 20 μL/minute for several minutes. Each TGFβ utilized a separate activation step on its own flow cell such that TGFβ1 was immobilized on Fc2, TGFβ2 on Fc3, and TGFβ3 on Fc4 with Fc1 as an activated and inactivated blank. Injections of TGFβ were performed as a series of 1 to 2 minute injections looking at immobilized level between each injection. The target immobilized density of each TGFβ ligand was 30 RU. After the TGFβ immobilization injections, 4 minutes of 1 M Ethanolamine hydrochloride-NaOH pH 8.5 was injected to block the surface. The NHS, EDC, and Ethanolamine used were from the BIACORE Amine Coupling Kit and the TGFβ1, TGFβ2, and TGFβ3 were from R&D Systems.

For affinity analysis the running buffer was switched to a thoroughly degassed form of the HBS-EP+ buffer above supplemented with 1 mg/mL BSA (Sigma Aldrich, St. Louis Mo.). Each of the antibodies was diluted in running buffer to 5 μg/mL (33.3 nM) and 4 subsequent five-fold dilutions were prepared setting up concentrations of 33.33 nM, 6.67 nM, 1.33 nM, 267 pM, and 53 pM for each. These were then injected using the Kinject setting for four minutes at 50 µL/minute, with a 900 second dissociation time. Regeneration was then performed with a 12 µL (14.4 second) injection of 100 mM HCl at 50 µL/minute followed by an 18 second buffer injection. Injections were across all flow cells simultaneously and samples were run injected in quadruplicates with blank injections bracketing each set of descending concentration injection groups for each antibody. This means that before the same sample was injected a second time all other concentrations of all antibodies were injected once.

The data were analyzed using Scrubber2 (BioLogic Software, Campbell Australia) and were double referenced by subtracting both the blank flow cell data and the averaged bracketing blank injections. The data were fit by simultaneously fitting the (KD) an offrate (kd) and onrate (ka), and are shown in Table 3 below.

unique property of binding to all three of the TGFβ isoforms with good affinity. The TGFβ-RII binds tightly only to TGFβ1 and TGFβ3 ligands, while the TGFβ-RIII binds best to TGFβ2 ligand.

A CM5 sensor chip (GE Healthcare) was used on a BIACORE 2000 system. The chip was preconditioned with several 30 second injections each at 50 µL/minute flow rate of 100 mM HCl and 50 mM NaOH prior to immobilization. Running buffer for immobilization was a HEPES Buffered Saline (HBS-EP+) with 10 mM Hepes, 150 mM Sodium Chloride, 3 mM EDTA, and 0.05% Polysorbate 20. The chip surface was activated with a seven minute injection at 10 µL/minute of a freshly mixed 1:1 solution of 0.1 M N-Hydroxysuccinimide (NHS) and 0.4 M 1-Ethyl-3-(3-dimethylaminopropyl) carbodiimide hydrochloride (EDC). Following the activation injection, 5 ug/mL TGFβ-RII, TGFβ-RIIb, or TGFβ-RIII (R&D Systems) in acetate pH 4.5 was injected at 20 µL/minute for four minutes and resulted in 1000-4000

TABLE 3

Affinity data from assay utilizing immobilized TGFβ and injected antibodies.

| Antibody | TGFβ1 | | | TGFβ2 | | | TGFβ3 | | |
|---|---|---|---|---|---|---|---|---|---|
| | ka (1/Ms) | kd (1/s) | KD | ka (1/Ms) | kd (1/s) | KD | ka (1/Ms) | kd (1/s) | KD |
| XPA.42.068 | 5.44E+06 | 1.70E−03 | 313 pM | 7.30E+06 | 7.98E−04 | 109 pM | 5.45E+06 | 6.96E−03 | 1.3 nM |
| XPA.42.089 | 5.98E+06 | 1.06E−03 | 177 pM | 4.80E+06 | 1.39E−03 | 290 pM | 3.40E+06 | 5.70E−02 | >17 nM |
| XPA.42.681 | 1.14E+07 | 3.63E−04 | 32 pM | 1.28E+07 | 3.94E−04 | 31 pM | 1.23E+07 | 6.65E−04 | 54 pM |
| BM-1 | 1.28E+07 | 3.90E−03 | 304 pM | 7.00E+06 | 6.84E−03 | 977 pM | 5.05E+06 | 9.46E−04 | 188 pM |

Consistent with the immobilized antibody results from Table 2, the affinity data measured in assays using immobilized antigen (Table 3) also showed that XPA.42.681 had the strongest (tightest) binding of any of the antibodies for each of the three isoforms of TGFβ, with similar affinity for each of the TGFβ isoforms. In addition, XPA.42.068 and XPA.42.089 had similar or stronger binding to the TGFβ1 and TGFβ2 isoforms compared with BM-1, but significantly less binding to the TGFβ3 isoform, compared either to the BM-1 antibody or relative to TGFβ1 binding. The difference in rate constants measured using the immobilized antibody versus immobilized antigen assays likely results from the inherent complexities of the system, but nevertheless each provides relatively high quality kinetic data and consistency in binding properties across the TGFβ isoforms and among the antibodies relative to each other.

Example 3. Measurement of Receptor Competition by TGFβ Antibodies

Antibodies were characterized for their ability to inhibit or block the binding of each of the three TGFβ ligands to TGFβ receptors by SPR competition assays. TGFβ signals through the TGFβ type II receptor (TGFβ-RII) which is a serine threonine kinase transmembrane protein and requires the cytoplasmic association of the TGFβ receptor type 1 protein (TGFβ-R1) for activation. The ligand binding role of TGFβ-RI is not clear and a recombinant form of TGFβ-RI did not demonstrate any binding at tested concentrations to any of the TGFβ1, TGFβ2 or TGFβ3 ligands, or the TGFβ-RII bound forms of those ligands, and therefore could not be evaluated in receptor competition experiments. The TGFβ type III receptor (TGFβ-RIII) has both membrane bound and soluble forms and is not believed to be involved in TGFβ signaling. The TGFβ-RIIb is a splice variant that contains a 26 amino acid insertion near the N-terminus and has the RU immobilized for each of the TGFβ receptors. Then, 8 minutes of 1 M Ethanolamine hydrochloride-NaOH pH 8.5 was injected to block the surface. The NHS, EDC, and Ethanolamine used were from the BIACORE Amine Coupling Kit. Fc1 was the activated and deactivated control.

Competition assays were performed using a running buffer of thoroughly degassed form of the HBS-EP+ buffer above supplemented with 1 mg/mL BSA. TGFβ ligands were used in all injections except blank controls at 100 ng/mL (10 nM) to 40 ng/mL (4 nM) and were prepared with 10 ug/mL (66.6 nM) of competitor and control antibodies. Samples were allowed to come to equilibrium for 40 minutes at room temperature before the BIACORE run was started. Equilibrated samples were then injected at 10 uL/minute for two minutes. Regeneration was performed every cycle with one injection of pH 2.5 glycine at 50 uL/minute for 9.6 seconds (8 µLs). Samples were run in at least duplicates and analyzed for the level of TGFβ bound.

As shown in Table 4 below, the results for antibodies XPA.42.068, XPA.42.089, XPA.42.681 and the BM-1 comparator suggest that each of these antibodies blocks the association of all three TGFβ ligands to the TFGβ-RII and TGFβ-RIII receptors, and that no clear distinction was made. This receptor competition pattern was not universal among all of the other antibodies tested, but for which data is not shown in the present disclosure.

TABLE 4

Receptor competition assay EC50 (nM antibody)

| | XPA.42.068 | XPA.42.089 | XPA.42.681 | BM-1 |
|---|---|---|---|---|
| TGFβ1/TGFβ-RII | 2.0E−09 | 1.7E−09 | 2.3E−09 | 2.4E−0.9 |
| TGFβ2/TGFβ-RII | 2.2E−09 | 1.8E−09 | 1.7E−09 | 2.8E−0.9 |
| TGFβ3/TGFβ-RII | 1.4E−09 | 3.4E−08 | 1.2E−09 | 1.6E−09 |
| TGFβ1/TGFβ-RIII | 6.0E−10 | 1.2E−09 | 1.2E−09 | 2.1E−0.9 |

TABLE 4-continued

Receptor competition assay EC50 (nM antibody)

|  | XPA.42.068 | XPA.42.089 | XPA.42.681 | BM-1 |
|---|---|---|---|---|
| TGFβ2/TGFβ-RIII | 2.4E−09 | 1.6E−09 | 2.1E−09 | 2.5E−09 |
| TGFβ3/TGFβ-RIII | 1.9E−09 | 3.1E−08 | 1.1E−09 | 1.4E-0.9 |

The potency of the XPA.42.068, XPA.42.089, XPA.42.681 and BM-1 antibodies in receptor competition generally correlated with their affinities to the various isoforms of TGFβ.

Example 4. Measurement of Epitope Competition Among TGFβ Antibodies

The ability of the XPA.42.068 and XPA.42.089 antibodies to bind to independent or overlapping epitopes on the TGFβ proteins was evaluated. While this pair-wise analysis was not straightforward due to varying affinities of the antibodies among the different isoforms of TGFβ, and the covalent homodimerization of TGFβ ligands, which results in binding in a two IgG per homodimer ratio (e.g., self pairing), a soluble competition-based assay was developed.

A CM5 sensor chip (GE Healthcare) was used on a BIACORE 2000 system. The chip was preconditioned with four 30 second injections at 50 uL/minute flow rate of 100 mM HCl prior to immobilization. Running buffer for immobilization was a HEPES Buffered Saline (HBS-EP+) with 10 mM Hepes, 150 mM Sodium Chloride, 3 mM EDTA, and 0.05% Polysorbate 20. The chip surface was activated with a seven minute injection at 10 uL/minute of a freshly mixed 1:1 solution of 0.1 M N-Hydroxysuccinimide (NHS) and 0.4 M 1-Ethyl-3-(3-dimethylaminopropyl) carbodiimide hydrochloride (EDC). Following the activation injection, a 1 ug/mL antibody XPA.42.089 in acetate pH 4.5 and was injected at 10 μL/minute for several minutes injections. Injections were monitored and performed sequentially to establish immobilization levels very close to 300 RU. Eight minutes of 1 M Ethanolamine hydrochloride-NaOH pH 8.5 was injected to block the surface. The NHS, EDC, and Ethanolamine used were from the BIACORE Amine Coupling Kit. Fc1 was the activated and deactivated control.

Competition assays were performed using a running buffer of thoroughly degassed form of the HBS-EP+ buffer above supplemented with 1 mg/mL BSA. TGFβ1, TGFβ2 and TGFβ3 were used in all injections at 0.1 ug/mL (4 nM), except blank controls, and were prepared with 20 ug/mL (133 nM) of competitor antibodies. The TGFβ-RIIb-Fc recombinant receptor (R&D Systems) also was included as a competitor. Samples were allowed to come to equilibrium for 40 minutes at room temperature before the BIACORE run was started. Equilibrated samples were then injected at 30 uL/minute for three minutes over all of the flow cells. Regeneration was performed every cycle with one injection of 50 mM NaOH at 50 uL/minute for 6 seconds (5 μLs) and followed by a thirty second buffer injection. Samples were run in duplicates and analyzed for level of TGFβ bound at the end of the three minutes.

TABLE 5

Binding competition (XPA.42.089 immobilized)

|  | TGFβ1 | TGFβ2 | TGFβ3 |
|---|---|---|---|
| Blank | −0.568 | 0.0655 | 0.3684 |
| No Ab | 63.85 | 61.05 | 23.65 |
| XPA.42.068 | 10.85 | 5.18 | 7.32 |
| XPA.42.089 | 1.7 | 0.3635 | 9.77 |
| TGFβ-RIIb | −0.316 | 38.2 | −0.378 |

As shown in Table 5 above, the data indicate that the XPA.42.068 and XPA.42.089 exhibited strong competition with each other for binding each of the TGFβ isoforms. The values represent the average RU or signal intensity of TGFβ binding that was measured during the injections of complex. This shows that the signal is greatly reduced when the complexed antibody is present. Any dissociation of the complex during the injection could allow for free or monovalently bound TGFβ to be bound by the XPA.42.089 capture antibody. It has been shown that the TGFβ-RIIb interaction with TGFβ2 is much weaker than the TGFβ1 and TGFβ3 proteins and the rapid offrate allows for relatively poor competition for TGFβ2 against the high affinity XPA.42.089. The XPA.42.681 antibody, which was derived from XPA.42.068, was not tested in the competition assays.

Example 5. Measurement of rhLAP Competition by TGFβ Antibodies

Additional competition assays were undertaken to determine whether the antibodies also interact with the latent form of TGFβ. The TGFβ pro-protein is cleaved within the golgi by a furin-like convertase into a N-terminal 249 amino acid latency associated peptide and a C-terminal 112 amino acid mature TGFβ1.

A CM5 sensor chip (GE Healthcare) was used on a BIACORE 2000 system. The chip was preconditioned with several 30 second injections each at 50 μL/minute flow rate of 100 mM HCl and 50 mM NaOH prior to immobilization. Running buffer for immobilization was a HEPES Buffered Saline (HBS-EP+) with 10 mM Hepes, 150 mM Sodium Chloride, 3 mM EDTA, and 0.05% Polysorbate 20. The chip surface was activated with a seven minute injection at 10 μL/minute of a freshly mixed 1:1 solution of 0.1 M N-Hydroxysuccinimide (NHS) and 0.4 M 1-Ethyl-3-(3-dimethylaminopropyl) carbodiimide hydrochloride (EDC). Following the activation injection 2 ug/mL recombinant human TGFβ1 Latency Associated Peptide (rhLAP) (R&D Systems) in acetate pH 4.5 was injected at 10 μL/minute for four minutes and resulted in 400 RU of rhLAP immobilized. 8 minutes of 1 M Ethanolamine hydrochloride-NaOH pH 8.5 was injected to block the surface. Fc1 was the activated and deactivated control.

The rhLAP competition assay was performed using a running buffer of a thoroughly degassed HBS-EP+ buffer as above supplemented with 1 mg/mL BSA. TGFβ1 was used in all injections except blank controls at 0.25 ug/mL (10 nM) and was prepared with 10 ug/mL (66.6 nM) of competitor and control antibodies. Samples were allowed to come to equilibrium for 40 minutes at room temperature before starting the BIACORE run. Equilibrated samples were then injected at 40 uL/minute for two minutes over the control and the rhLAP surface. Regeneration was performed every cycle with two injections of 100 mM HCl at 100 uL/minute for 9.6 seconds (16 μLs). Samples were run in duplicates and analyzed for the level of TGFβ1 bound.

The antibodies XPA.42.068, XPA.42.089 and BM-1 comparator were each tested in the rhLAP competition assay.

The XPA.42.681 antibody, which was derived from XPA.42.068, was not tested. As shown in FIG. 1, XPA.42.068, XPA.42.089 and BM-1 each exhibited a high level of competition with rhLAP, indicating that the antibodies interact with the active form of TGFβ and do not recognize latent TGFβ.

Example 6. Measurement of Neutralization by TGFβ Antibodies in HT-2 Assay

To determine if the antibodies functionally neutralized TGFβ isoforms, the assay methods of Ruegemer et al. (J Immunol. 144:1767-76; 1990) were adapted whereby HT-2 murine T cells are grown with IL-4, and with or without the addition of TGFβ1, TGFβ2 or TGFβ3. TGFβ isoforms inhibit IL-4 dependent growth of HT-2 cells through trans-activation of genes promoting cell cycle arrest. IL-4 trans-activates a mitogenic gene expression program by activating targets such as c-myc and GM-CSF; whereas TGFβ signaling transactivates genes which suppress c-myc and GM-CSF expression. If TGFβ signaling is abrogated by a neutralizing antibody, HT-2 cells proliferate. Differences in growth were scored by CELL TITERGLO® (Promega #G7571) viability assay which measures ATP as a readout for metabolically active cells.

HT-2 murine T cells were maintained by splitting every 2-3 days at 1.5e4-2.5e4 cells/mL in RPMI+10% FBS, 10 mM Hepes, 2 mM glutamine, 50 uM 2-ME. Fresh recombinant mouse IL-2 (R&D Systems) was added at 200 IU/mL to each flask from a concentrated stock. On day 1, cells were washed in media to remove IL-2 and dispensed into opaque 96 well plates at 10,000 cells per well with 2000 IU/ml recombinant mouse IL-4 (R&D Systems). TGFβ1, TGFβ2 or TGFβ3 (PeproTech #100-21, 100-35B, 100-36E) was added after 1 hour pre-incubation with or without antibodies across a titration series. After 48 hour incubation at 37° C., viable cell population was scored on MDS Flexstation3 using CELL TITERGLO® according to manufacturers recommendations.

TABLE 6

HT-2 cell neutralization assay

| Antibody | TGFβ2 | TGFβ1 | TGFβ2 |
|---|---|---|---|
| XPA.42.068 | + | 98.0 | 0.0 |
| XPA.42.089 | + | 57.0 | 0.0 |
| XPA.42.681 | + | Potent | 30.3 |
| BM-1 | + | 220.0 | 196.0 |

The antibodies were initially tested for neutralization of TGFβ2 activity at a single 10 ug/ml dilution point in the HT-2 assay, and each of the antibodies was confirmed to be positive, with the antibodies XPA.42.068, XPA.42.089 and XPA.42.681 having greater potency than the BM-1 comparator antibody at the single point tested. Neutralization of TGFβ1 and TGFβ3 was then determined and an IC50 calculated for each antibody across a 6 point dilution series. Again, each of the XPA.42.068, XPA.42.089 and XPA.42.681 demonstrated greater potency than the BM-1 comparator with respect to TGFβ1 neutralization, but only XPA.42.681 was found to exhibit greater potency TGFβ3 neutralization, and thus was the most potent pan-inhibitor of TGFβ (Table 6). XPA.42.681 exhibited enhanced potency in this assay, with the lowest concentrations tested significantly inhibiting TGFβ1, and thus a specific IC50 calculation could not be made.

Example 7. Measurement of Neutralization by TGFβ Antibodies in IL-11 Release Assay A second neutralization assay scored TGFβ mediated secretion of IL-11 from A549 lung carcinoma cells, which is part of a pro-fibrotic response in lung fibroblasts and epithelial cells. TGFβ also mediates secretion of IL-11 from MDA-MB-231 cells which promotes metastasis to the bone. This assay models TGFβ mediated biological responses that contribute to fibrosis and metastatic disease. The IL-11 release assay was adapted from Rapoza et al. (J Immunol. Methods 316:18-26; 2006), whereby A549 cells were seeded into 96 well plates and the next day cells were treated with or without the TGFβ isoforms, pre-incubated with or without neutralizing antibodies. IL-11 release was scored in cell culture supernatants by ELISA.

In this assay, A549 cells were grown in F12+10% serum. The day prior to analysis, cells were detached with versene (to retain receptor expression) and seeded at 40,000 cells/well into a 96 well flat bottom plate. The next day TGFβ1, TGFβ2 or TGFβ3 at EC80 was pre-incubated for 1 hour with or without antibodies across a dilution series prior to adding to cells. As a control, TGFβ alone, TGFβ+anti-KLH-G2 control antibody or media alone was added to plates. After 24 hours at 37° C., supernatant was harvested and IL-11 was scored by ELISA using the IL-11 Duo Set ELISA kit (R&D Systems) according to manufacturer's recommendations.

TABLE 7

| IL-11 Release Assay-IC50 (ng/mL) | | | |
|---|---|---|---|
| Antibody | TGFβ1 | TGFβ2 | TGFβ3 |
| XPA.42.068 | 220.5 | 110.5 | 1795.0 |
| XPA.42.089 | 37.0 | 58.0 | 0.0 |
| XPA.42.681 | 0.4 | 1.0 | 0.8 |
| BM-1 | 292.0 | 498.0 | 12.0 |

As shown in Table 7 above, and similar to the HT-2 assay, the IL-11 release assay results indicated that XPA.42.681 was the most potent of any of the antibodies for each of the three isoforms of TGFβ. In contrast to the HT-2 assay, the XPA.42.681 antibody exhibited a dose dependent effect on IL-11 release which enabled IC50 determination, and also revealed generally similar IC50 values for each TGFβ isoform. Antibodies XPA.42.068 and XPA.42.089 also showed good neutralization of the TGFβ1 and TGFβ2 isoforms (more potent than BM-1 comparator), but with significantly less neutralization of TGFβ3 compared either to the BM-1 antibody or relative to the neutralization of TGFβ1 and TGFβ2.

Example 8. Measurement of Neutralization by TGFβ Antibodies in pSMAD2 Assay

Figure 2A:
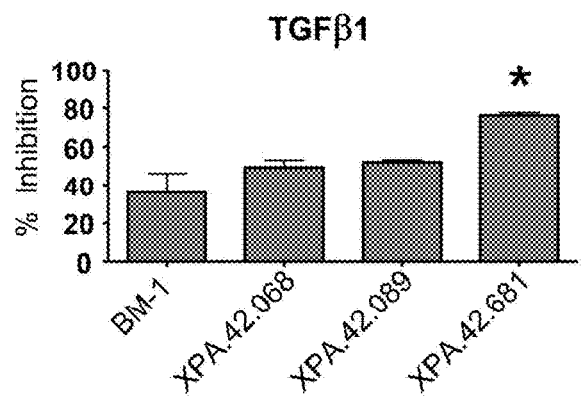
FIGS. 2A-2C show neutralization of pSMAD signaling in cells by TGFβ antibodies.
Figure 2B:
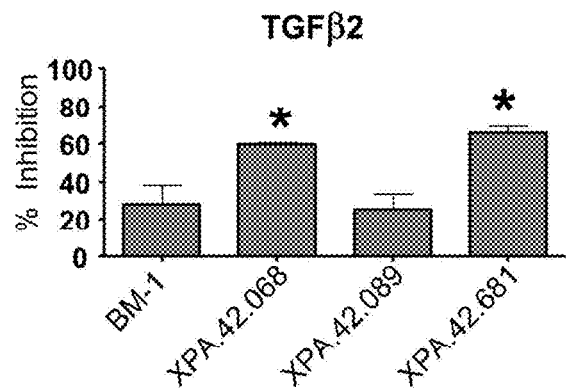
Figure 2C:
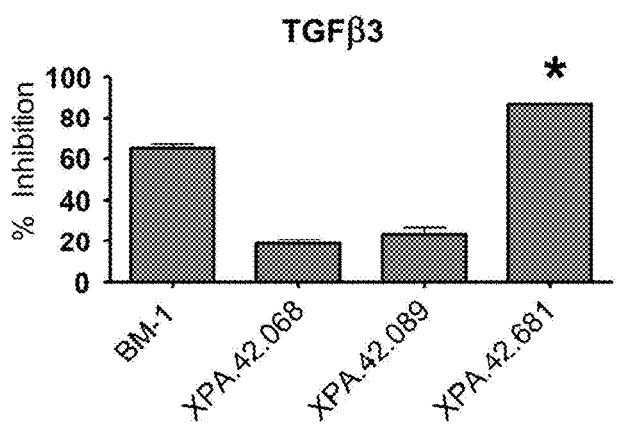

To further characterize the antibodies, a phospho-SMAD2 (pSMAD2) assay was developed to score neutralization of TGFβ signaling through the TGFβRII/TGFβRI receptor complex. Detroit 562 cells were maintained in IMDM+10% FBS. Cells were detached with versene and plated into a 6 well dish at 500,000 cells per well. The next day, the cells were serum starved in serum free IMDM for 3 hours prior to 30 minute exposure to TGFβ1, TGFβ2 or TGFβ3 pre-incubated for 1 hour with or without antibodies. After 30 minutes at 37° C., cells were lysed and pSMAD2 and total SMAD2 was scored by ELISA using commercial kits (Cell Signaling Technology, Danvers, Mass.) according to the manufacturer's recommendations for detection. Percentage of pSMAD2 was normalized to total SMAD2 and percent inhibition was calculated for each clone from normalized % pSMAD2 relative to anti-KLH control (FIG. 2). T test (two tailed) showed that the XPA.42.681 antibody was significantly more potent than the BM-1 comparator antibody in neutralizing pSMAD signaling across all TGFβ isoforms (p<0.05). Additionally, XPA.42.068 was significantly more potent against TGFβ2 relative to the BM-1 comparator.

Example 9. Measurement of TGFβ Antibody Activity in a Regulatory T Cell Assay

Figure 3:
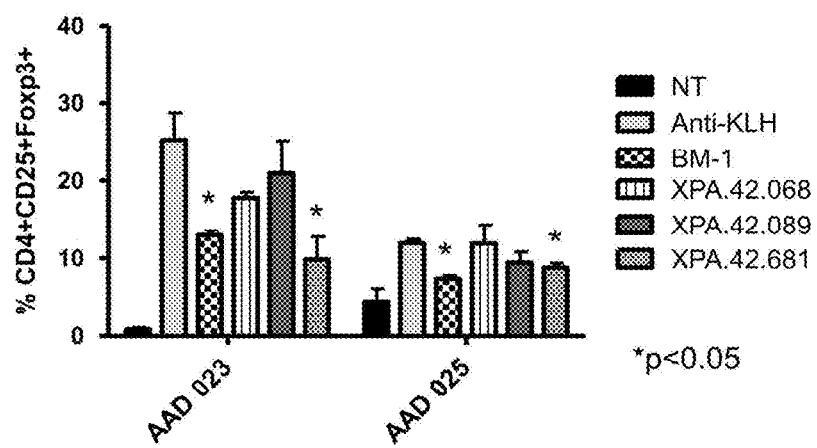
FIG. 3 is a graph showing inhibition of regulatory T cells (Treg) by TGFβ antibodies.

To characterize the activity of the antibodies on endogenous TGFβ, a regulatory T (Treg) cell assay was established, based on methods similar to Tran et al. (Blood 110:2983-2990; 2007). T cells were isolated from frozen vials of human PBMCs using the EasySep T cell Enrichment kit (StemCell Technologies, Vancouver, BC). T cells were activated with plate-bound anti-human CD3 antibody (eBioscience, San Diego, Calif.) at 10 ug/ml and soluble anti-human CD28 antibody (eBioscience) at 2 ug/ml. The cells were also treated concurrently with 15 ug/ml of the TGFβ antibodies or controls. After 4 days, the cells were stained with anti-human CD4-FITC (BD Biosciences) and anti-human CD25-A647 (BioLegend, San Diego, Calif.) for 30 minutes at 4° C. Cells were fixed with FOXP3 Fix buffer (BioLegend) for 20 minutes at room temperature, and permeabilized for 15 minutes at room temperature with FOXP3 permeabilization buffer (BioLegend). Cells were stained with 1:25 dilution of anti-human FOXP3-PE (BioLegend) and analyzed on a BD FACSCanto™ system. CD4+ cells were gated and CD4+CD25+Foxp3+ sub populations were quantitated with Flowjo software. Antibodies were evaluated in this assay using 4 or 5 different PBMC donors and representative data from 2 donors are shown (FIG. 3).

Although a range of activity was found due to donor dependent differences in cell populations, generally, the XPA.42.681 and the BM-1 comparator antibodies inhibited the Treg cell population, while the XPA.42.068 and XPA.42.089 antibodies provided partial activity in this assay.

Example 10. Measurement of TGFβ Antibody Activity in an EMT Assay

Epithelial to mesenchymal transition (EMT) enables self renewal of tumor cells to promote cancer invasion and metastasis. Induction of EMT is driven by cytokines, including TGFβ1, TGFβ2 and TGFβ3, and all three isoforms may be involved sequentially in EMT depending on tissue type (Boyer et al., Dev. Biol. 208:530-545, 1999; Bhowmick et al., Mol. Biol. Cell 12:27-36, 2001; Camenisch et al., Dev. Biol. 248:170-181, 2002). An EMT assay was developed using primary human mammary epithelial cells (HMEC), similar to Mani et al. (Cell 133:704-715; 2008) to determine if the antibodies inhibit this process in vitro.

Human mammary epithelial cells (Lonza, Basel, Switzerland) were grown in MEGM complete media (Lonza) as recommended by manufacturer. For sub-culturing, cells were trypsinized and treated with trypsin neutralizing solution (Lonza) prior to seeding. HMEC cells were seeded at 3500 cells/cm$^2$ in 8-well chamber slides and treated with or without TGFβ at 2.5 ng/ml, pre-incubated with or without antibodies for 30 minutes. Cells were incubated at 37° C. for 8 days and fresh media+reagents were added after 4 days. On day 8, cells were fixed with 4% paraformaldehyde for 15 minutes at room temperature. Cells were rinsed twice in PBS and permeabilized in PBS+0.25% Triton X-100 for 10 minutes, before blocking with PBS-TWEEN+10% goat serum for 30 minutes. Cells were stained overnight at 4° C. for a mesenchymal marker using anti-human vimentin (Cell Signaling Technology, Danvers, Mass.) and for an epithelial marker using anti-human E-Cadherin (Cell Signaling Technology) diluted 1:200 or 1:500, respectively. Cells were washed in PBS 3 times and incubated with appropriate secondary antibodies Alexa Fluor 488 goat anti-rabbit or Alexa Fluor 568 goat anti-rabbit (Invitrogen, Carlsbad, Calif.) diluted in blocking solution for 1 hour at room temperature and protected from light. Slides were washed and mounted with Gold Anti-Fade/DAPI prior to fluorescence microscopy.

Exposure of HMEC cells to TGFβ in the presence of the anti-KLH control antibody results in increased vimentin staining and a reduction in total cell density, consistent with TGFβ mediated growth arrest and differentiation to a mesenchymal phenotype. Neutralization of TGFβ1 mediated EMT was evident based on reduced vimentin staining, which correlated with increased cell density for the XPA.42.681, XPA.42.068 and XPA.42.089 antibodies, while an intermediate response was observed for the BM-1 comparator, as vimentin staining was present, although not to the same degree as anti-KLH control (data not shown). Additionally, each of the antibodies inhibited EMT driven by TGFβ2, although the BM-1 comparator antibody appeared less potent based on Vimentin signal intensity, E-cadherin staining and increased cell density. For neutralization of TGFβ3 mediated EMT, the XPA.42.681 antibody was most potent, followed by BM-1 and XPA.42.068, while XPA.42.089 did not appear different from the anti-KLH control.

Example 11. Tumor Inhibition by TGFβ Antibodies in a Xenograft Mouse Model

Figure 4:
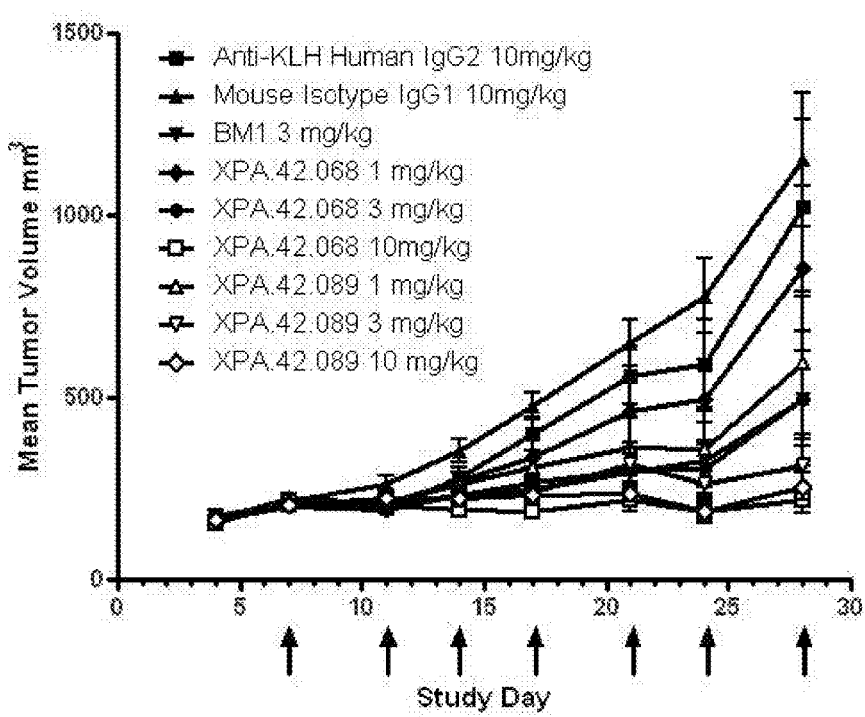
FIG. 4 is a graph showing tumor inhibition in a xenograft mouse model by TGFβ antibodies.

The antibodies XPA.42.068 and XPA.42.089 were evaluated for their ability to inhibit tumor growth in a xenograft model derived from Detroit 562, a human pharyngeal cancer cell line (Van Aarsen et al., Cancer Res. 68:561-70; 2008). Eight to nine week old Nu/Nu mice (Charles River Laboratories) were implanted subcutaneously with 5×10$^6$ Detroit 562 cells in BD MATRIGEL™ (1:1, 200 uL) per animal, into the lower left ventral abdominal region. Animals were randomized into test groups of twelve mice each: anti-KLH human IgG2 isotype control (10 mg/kg), XPA.42.068 (1, 3, or 10 mg/kg dose), XPA.42.089 (1, 3, or 10 mg/kg dose), BM-1 comparator (3 mg/kg), or mouse isotype control IgG1 (3 mg/kg). Dosing and tumor volume measurements were done biweekly (FIG. 4). Animals were sacrificed the day after the last dose (day 28), after 7 doses of antibody treatment. For all measurements, statistical significance was determined by one-tailed Student's t-test.

As shown in FIG. 4, tumors treated with XPA.42.089 trended smaller than tumors treated with XPA.42.068, with significant differences in the higher dose levels when compared to anti-KLH human IgG2 control. Percent Tumor Growth Inhibition (TGI) was compared to IgG control antibody on day 28 in all test groups. Tumors from the XPA.42.068 (3 and 10 mg/kg), XPA.42.089 (3 and 10 mg/kg), and also the BM-1 comparator (3 mg/kg) treated groups were significantly smaller at day 28 than the 1 mg/kg treated groups (P value <0.05). Additionally, XPA.42.068 at 10 mg/kg and XPA.42.089 at 3 and 10 mg/kg showed significant differences compared to IgG control using Tukey's ANOVA testing (Table 8).

TABLE 8

Tumor growth inhibition in xenograft tumor model

| | | Day 28 | |
|---|---|---|---|
| Groups | TGI % | Tukey's Multiple Comparison Anova p value P < 0.05? | t-Test One Tailed p-Value |
| 3 mg/kg BM-1 vs Mouse IgG1 | 70.1 | No | 0.0089 |
| 1 mg/kg XPA.42.068 vs anti-KLH IgG2 | 21.3 | No | 0.3037 |
| 3 mg/kg XPA.42.068 vs anti-KLH IgG2 | 63.3 | No | 0.0339 |
| 10 mg/kg XPA.42.068 vs anti-KLH IgG2 | 99.8 | Yes | 0.0014 |
| 1 mg/kg XPA.42.089 vs anti-KLH IgG2 | 51.4 | No | 0.0948 |
| 3 mg/kg XPA.42.089 vs anti-KLH IgG2 | 87.3 | Yes | 0.0045 |
| 10 mg/kg XPA.42.089 vs anti-KLH IgG2 | 93.4 | Yes | 0.0024 |

Figure 5:
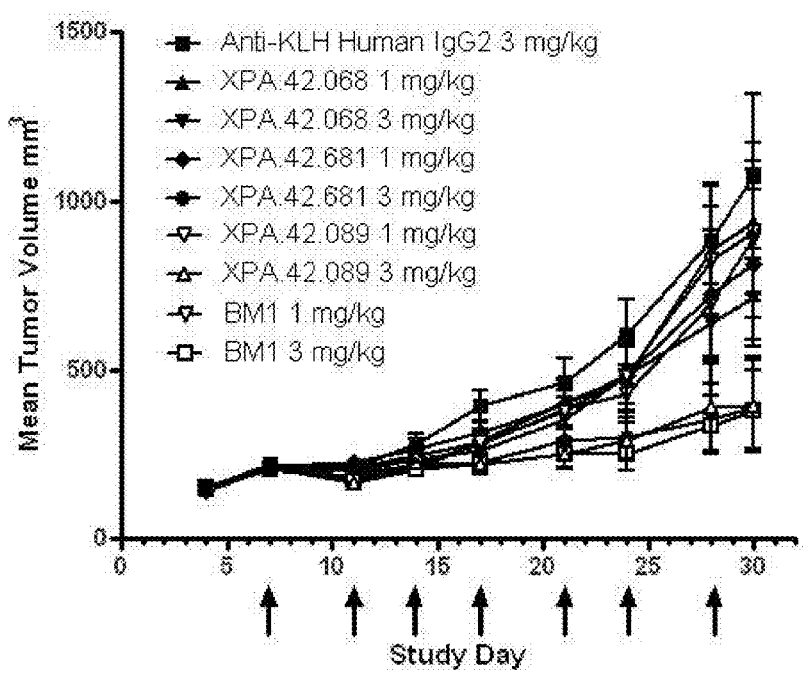
FIG. 5 is a graph showing tumor inhibition in a xenograft mouse model by TGFβ antibodies.

Further evaluation in the Detroit 562 xenograft model was conducted using the antibodies XPA.42.068, XPA.42.089 and XPA.42.681. Eight to nine week old Nu/Nu mice (Charles River Laboratories) were implanted subcutaneously with $5 \times 10^6$ Detroit 562 cells in BD MATRIGEL™ (1:1, 200 uL) per animal, into the lower left ventral abdominal region. Animals were randomized into test groups of twelve mice each: anti-KLH human IgG2 isotype control (3 mg/kg), XPA.42.068 (1 or 3 mg/kg dose), XPA.42.089 (1 or 3 mg/kg dose), XPA.42.681 (1 or 3 mg/kg dose), BM-1 comparator (1 or 3 mg/kg dose). Dosing and tumor volume measurements were done biweekly (FIG. 5). Animals were sacrificed the day after the last dose (day 30), after 7 doses of antibody treatment. For all measurements, statistical significance was determined by one-tailed Student's t-test.

As shown in FIG. 5 and Table 9, tumors treated with XPA.42.681, XPA.42.089, and the BM-1 comparator at 3 mg/kg showed significant differences in percent TGI and mean tumor volumes at day 30 compared with control antibody. Comparisons among these groups did not show significant differences using Tukey's ANOVA testing.

TABLE 9

Tumor growth inhibition in xenograft tumor model

| | | Day 30 | |
|---|---|---|---|
| Groups (vs. anti-KLH IgG2) | TGI % | Tukey's Multiple Comparison ANOVAs p value p < 0.05? | t-Test One-Tailed p-Value |
| XPA.42.068 (1 mg/kg) | 15.9 | No | 0.3434 |
| XPA.42.068 (3 mg/kg) | 42.7 | No | 0.1046 |
| XPA.42.681 (1 mg/kg) | 30.4 | No | 0.2183 |
| XPA.42.681 (3 mg/kg) | 78.7 | No | 0.0119 |
| BM-1 (1 mg/kg) | 20.7 | No | 0.3010 |
| BM-1 (3 mg/kg) | 79.3 | No | 0.0096 |
| XPA.42.089 (1 mg/kg) | 18.5 | No | 0.3030 |
| XPA.42.089 (3 mg/kg) | 81.8 | No | 0.0094 |

Example 12. Tumor Inhibition by TGFβ Antibodies in a Syngeneic Mouse Model

Figure 6:
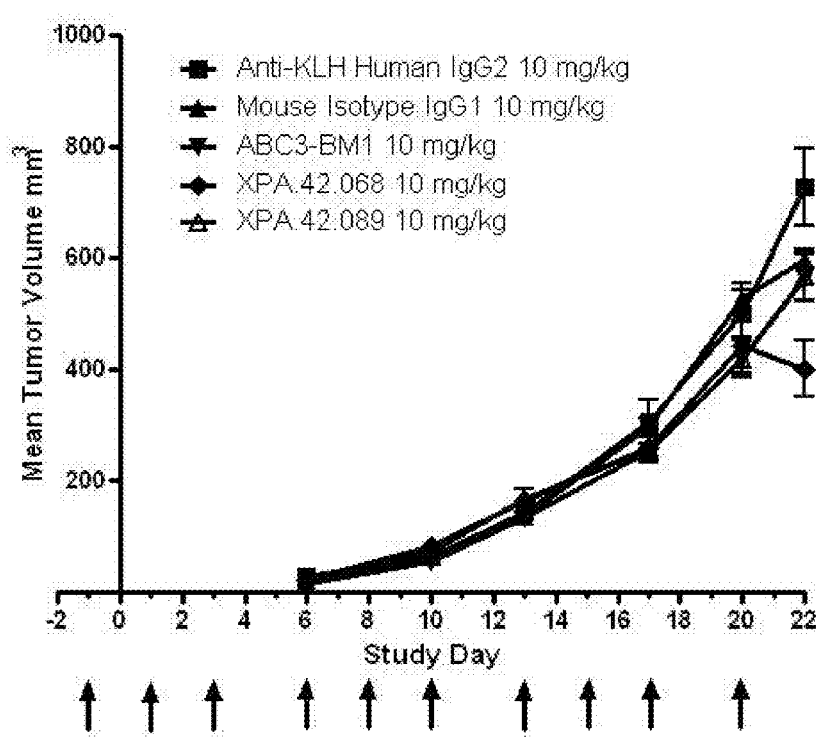
FIG. 6 is a graph showing tumor inhibition in a syngeneic mouse model by TGFβ antibodies.

The antibodies XPA.42.068 and XPA.42.089 were also evaluated for their ability to inhibit tumor growth in a syngeneic model, using 4T1 breast cancer cells, using a protocol adapted from Nam et al. (Cancer Res. 68:3915-23; 2008). Balb/c female mice eight weeks of age were implanted subcutaneously with 250,000 4T1 cells in the $4^{th}$ mammary fat pad on day 0. Animals were randomized into test groups of twelve mice each and administered antibody three times per week (beginning at day −1) at a single dose level of 10 mg/kg, with anti-KLH human IgG2 isotype control, XPA.42.068, XPA.42.089, BM-1 comparator, or mouse isotype control IgG1. Tumor volumes were measured twice weekly over the course of the experiment and the data are shown in FIG. 6. The end of study tumor volume data indicated that both XPA.42.068 and XPA.42.089 significantly inhibited tumor growth as compared to the KLH control antibody.

Figure 7:
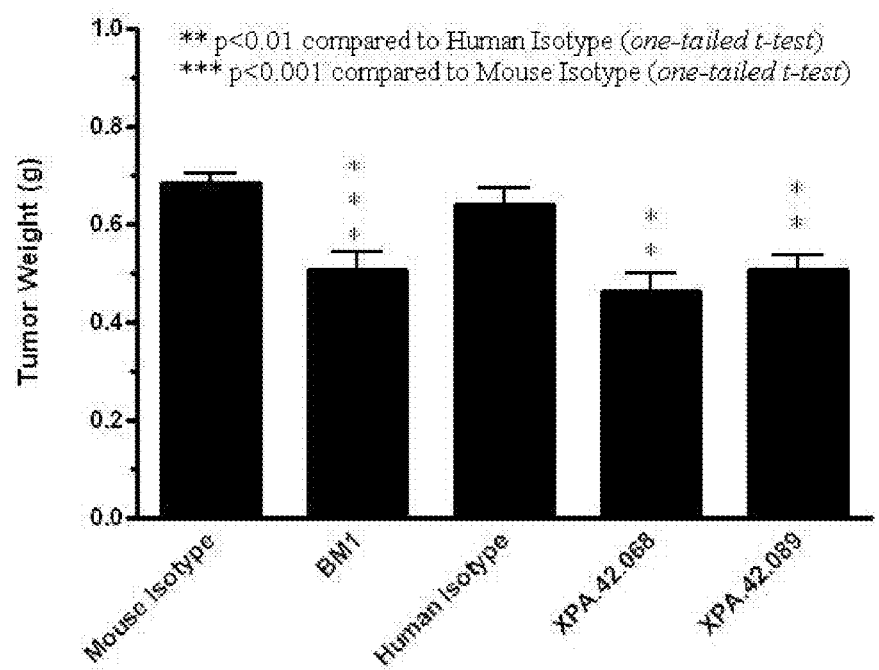
FIG. 7 is a graph showing tumor inhibition in a syngeneic mouse model by TGFβ antibodies.

Additionally, the animals were sacrificed on the final study day (day 23) and tumors were removed to determine tumor weights. Each of the XPA.42.089, XPA.42.068 and BM-1 antibodies significantly reduced tumor mass relative to the human or mouse control antibodies (FIG. 7).

Figure 8:
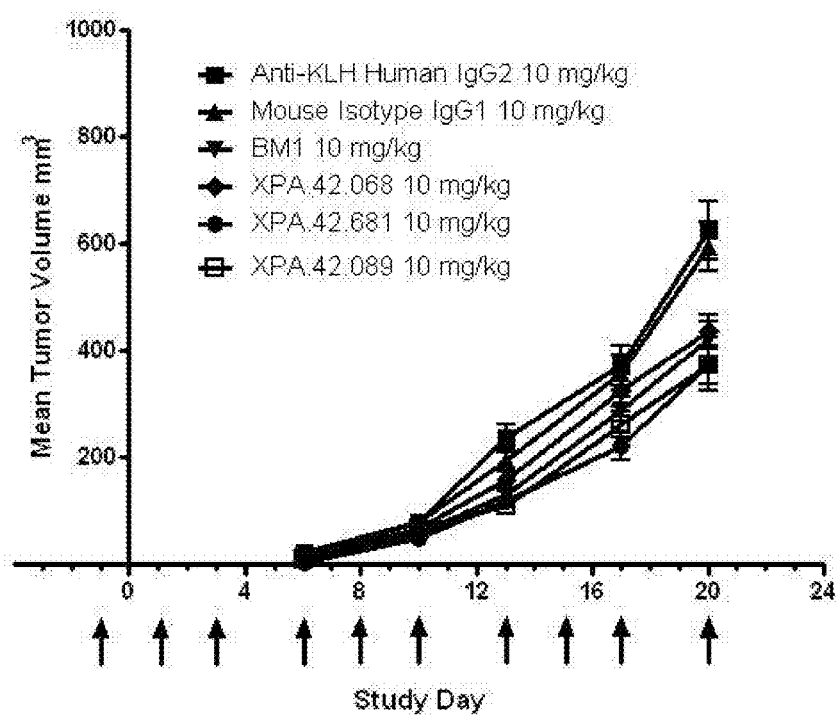
FIG. 8 is a graph showing tumor inhibition in a syngeneic mouse model by TGFβ antibodies.

Further evaluation in the 4T1 syngeneic model was conducted using the antibodies XPA.42.068, XPA.42.089 and XPA.42.681. Eight week old Balb/c mice were implanted subcutaneously with 250,000 4T1 cells in the $4^{th}$ mammary fat pad on day 0. Animals were randomized into test groups of twelve mice each and administered antibody three times per week (beginning at day −1) at a single dose level of 10 mg/kg, with anti-KLH human IgG2 isotype control, XPA.42.068, XPA.42.089, XPA.42.681, BM-1, or mouse isotype control IgG1. Tumor volumes were measured twice weekly over the course of the experiment and the data are shown in FIG. 8. The end of study tumor volume data indicated that each of the antibodies XPA.42.068, XPA.42.089, XPA.42.681 and BM-1 significantly inhibited tumor growth as compared to the human or mouse control antibodies.

Figure 9:
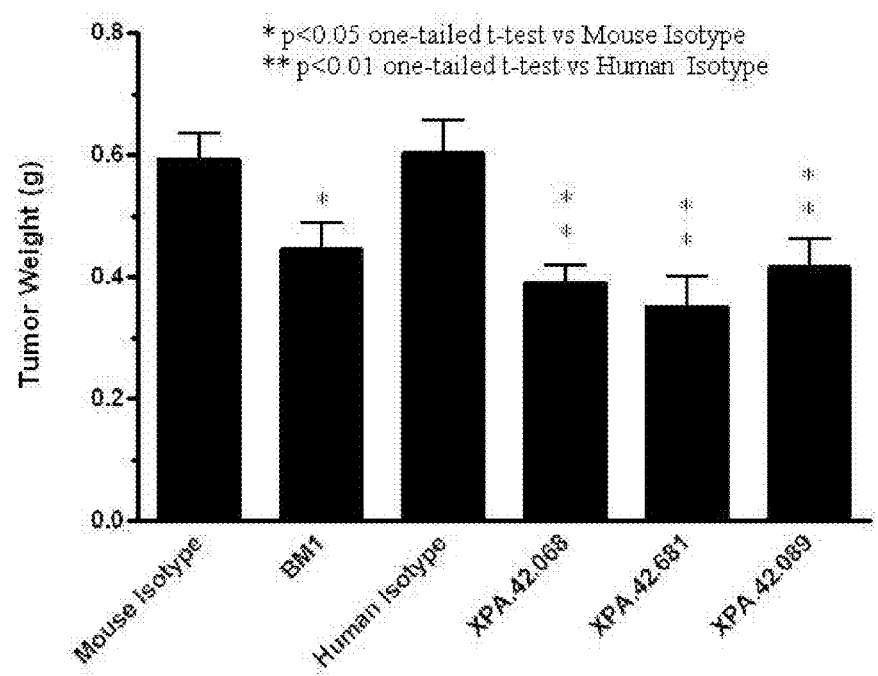
FIG. 9 is a graph showing tumor inhibition in a syngeneic mouse model by TGFβ antibodies.

Additionally, the animals were sacrificed on the final study day (day 21) and tumors were removed to determine tumor weights. Each of the XPA.42.089, XPA.42.068, XPA.42.681 and BM-1 antibodies significantly reduced tumor mass relative to the human or mouse control antibodies (FIG. 9).

Example 13. In Vivo Effect of TGFβ Antibodies on NK Cells in Mouse Tumor Model

Figure 10:
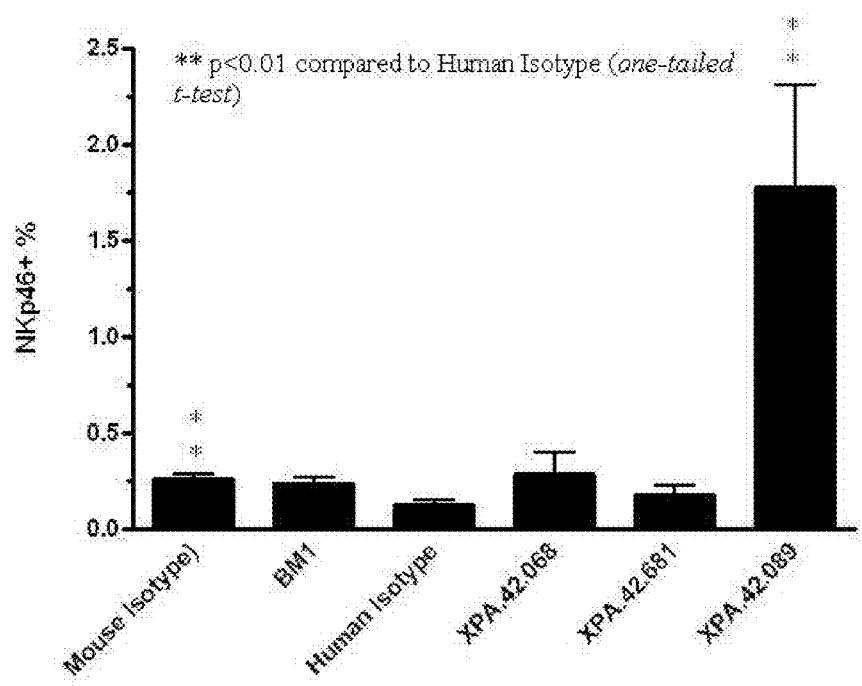
FIG. 10 is a graph showing the in vivo effect of TGFβ antibodies on natural killer cells in tumors, in a syngeneic mouse tumor model.

To evaluate whether the TGFβ antibodies exhibited an immune modulatory effect in vivo on natural killer (NK) cells present in tumors, the isolated tumors that were removed from mice in the 4T1 syngeneic model experiments above were digested to generate single cell suspensions. Briefly, freshly harvested tumors were minced and digested in 2.5 mg/mL collagenase II and 2.5 mg/mL collagenase IV in HBSS (15 minutes at 37° C.). Cells were counted and resuspended at 2e6/mL in PBS, 0.5% BSA, 0.1% NaN3 and 10 ug/mL of the 2.4G2 anti-mouse Fc blocking antibody (eBioscience, San Diego, Calif.), and incubated for 15 minutes at 4° C. After washing in PBS with 0.5% BSA, cells were stained for 30 minutes at 4° C. with an anti-CD335 (anti-NKp46) antibody, conjugated for immunofluorescent staining with flow cytometric analysis (BioLegend, San Diego, Calif.). CD335, also known as NKp46, is a cell surface marker exclusively expressed on CD3−CD56+ NK cells, and considered to be a universal marker for NK cells. Cells were fixed in freshly prepared 2% paraformaldehyde and analyzed on a BD FACSCanto™ system. Single color controls were also prepared for compensation. As shown in FIG. 10, the XPA.42.089 antibody significantly increased expression of the NK cell marker NKp46 (CD335) within tumors removed from mice, as compared to isotype control antibody. The BM-1, XPA.42.068 and XPA.42.681 antibodies did not lead to a similar increase in NKp46.

Example 14. In Vivo Effect of TGFβ Antibodies on MDSC in Mouse Tumor Model

Figure 11:
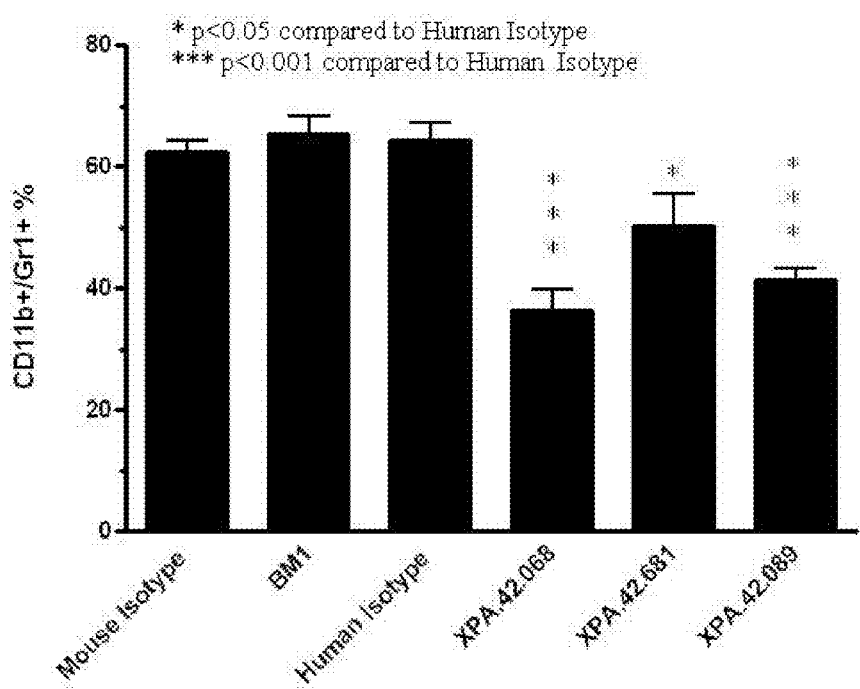
FIG. 11 is a graph showing the in vivo effect of TGFβ antibodies on myeloid-derived suppressor cells in tumors, in a syngeneic mouse model.

To evaluate whether the TGFβ antibodies exhibited an immune modulatory effect in vivo on myeloid-derived suppressor cells (MDSC) (CD11b+/Gr1+) present in tumors, the isolated tumors that were removed from mice in the 4T1 syngeneic model experiments were prepared as described above and stained for 30 minutes at 4° C. with anti-CD11b and anti-Gr1 antibodies conjugated for immunofluorescent staining with flow cytometric analysis (BioLegend, San Diego, Calif.). CD11b, also known as $α_M$-integrin, and the myeloid lineage differentiation antigen Gr1, also known as Ly6G, are cell surface markers co-expressed on MDSC. Cells were fixed in freshly prepared 2% paraformaldehyde and analyzed on a BD FACSCanto™ system. Single color controls were also prepared for compensation. As shown in FIG. 11, the XPA.42.068, XPA.42.089 and XPA.42.681 antibodies significantly decreased accumulation of myeloid-derived suppressor cells (MDSC, CD11b+/Gr1+) within tumors removed from mice, as compared to isotype control antibody. The BM-1 comparator antibody did not exhibit a similar decrease in MDSC.

Figure 12:
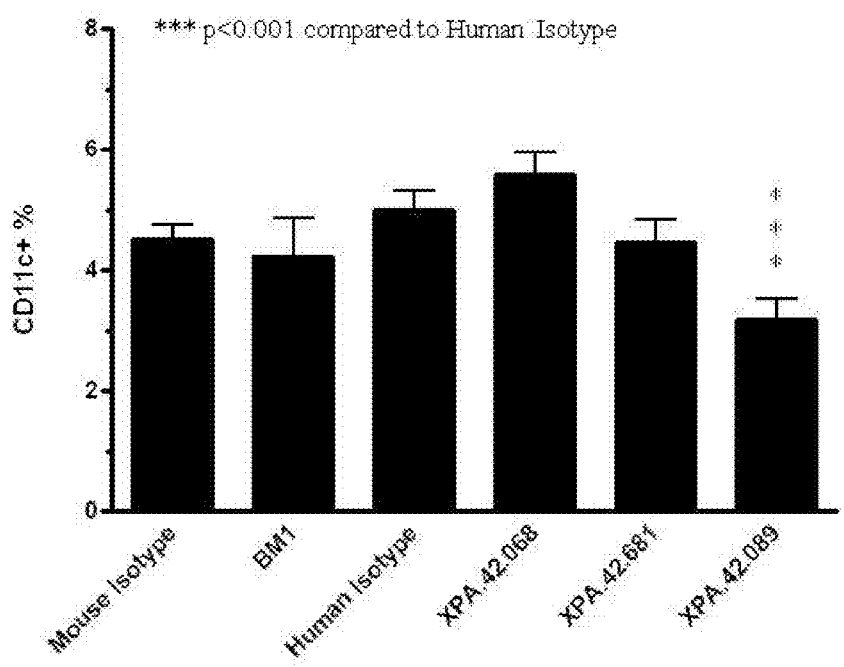
FIG. 12 is a graph showing the in vivo effect of TGFβ antibodies on dendritic cells in tumors in a syngeneic mouse tumor model.

Example 15. In Vivo Effect of TGFβ Antibodies on Dendritic Cells in Mouse Tumor Model To evaluate whether the TGFβ antibodies exhibited an immune modulatory effect in vivo on dendritic cells (DC) present in tumors, the isolated tumors that were removed from mice in the 4T1 syngeneic model experiments were prepared as described above and stained for 30 minutes at 4° C. with anti-CD11c antibody conjugated for immunofluorescent staining with flow cytometric analysis (BioLegend, San Diego, Calif.). CD11c, also known as $α_x$ integrin, is a cell surface marker found on DC. Cells were fixed in freshly prepared 2% paraformaldehyde and analyzed on a BD FACSCanto™ system. Single color controls were also prepared for compensation. As shown in FIG. 12, the XPA.42.089 antibody significantly decreased expression of the DC marker CD11c within tumors removed from mice, as compared to isotype control antibody. The BM-1, XPA.42.068 and XPA.42.681 antibodies did not exhibit a similar decrease in CD11c.

Figure 13:
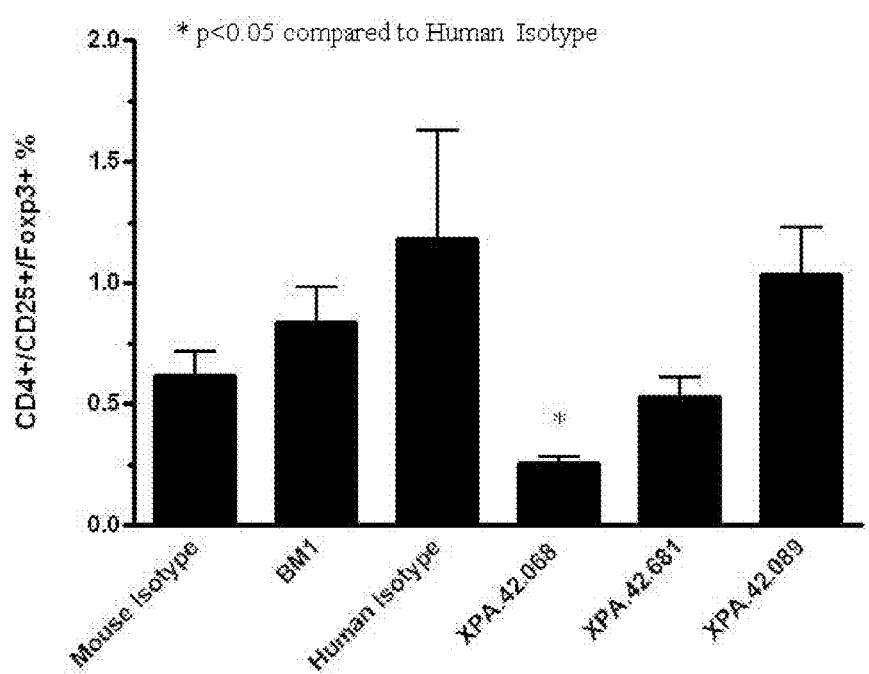
FIG. 13 is a graph showing the in vivo effect of TGFβ antibodies on regulatory T cells in tumors in a syngeneic mouse tumor model.

Example 16. In Vivo Effect of TGFβ Antibodies on Regulatory T Cells in Mouse Tumor Model To evaluate whether the TGFβ antibodies exhibited an immune modulatory effect in vivo on regulatory T cells (Treg) present in tumors, the isolated tumors that were removed from mice in the 4T1 syngeneic model experiments were prepared as described above and stained for 30 minutes at 4° C. with anti-CD4, anti-CD25 and anti-FOXP3 antibodies conjugated for immunofluorescent staining with flow cytometric analysis (BioLegend, San Diego, Calif.). CD4, also known as L3T4, as well as CD25, also known as the low affinity IL-2Ra, and also FOXP3, also known as Forkhead box protein P3, are each cell surface markers found on Treg cells. Cells were fixed in freshly prepared 2% paraformaldehyde and analyzed on a BD FACSCANTO™ system. Single color controls were also prepared for compensation. As shown in FIG. 13, the XPA.42.068 antibody significantly decreased accumulation of Treg cells within tumors removed from mice, as compared to isotype control antibody. The BM-1, XPA.42.089 and XPA.42.681 antibodies did not exhibit a similar decrease in T-reg cells.

Figure 14:
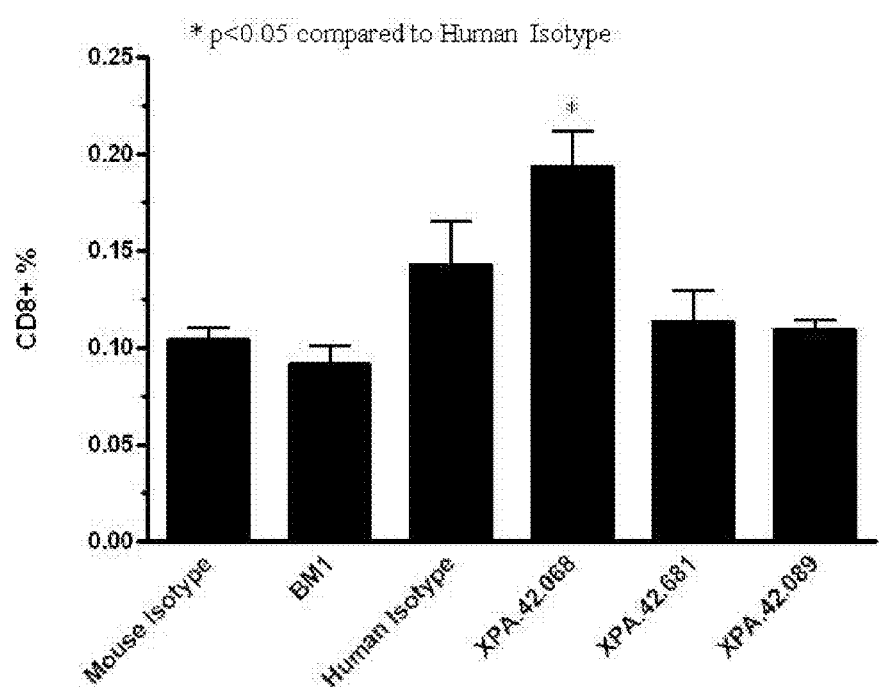
FIG. 14 is a graph showing the in vivo effect of TGFβ antibodies on cytotoxic T cells in tumors in a syngeneic mouse tumor model.

Example 17. In Vivo Effect of TGFβ Antibodies on Cytotoxic T Cells in Mouse Tumor Model To evaluate whether the TGFβ antibodies exhibited an immune modulatory effect in vivo on cytotoxic T lymphocyte cells (CTL) present in tumors, the isolated tumors that were removed from mice in the 4T1 syngeneic model experiments were prepared as described above and stained for 30 minutes at 4° C. with anti-CD8 antibody conjugated for immunofluorescent staining with flow cytometric analysis (BioLegend, San Diego, Calif.). CD8 is a cell surface marker found on CTL. Cells were fixed in freshly prepared 2% paraformaldehyde and analyzed on a BD FACSCANTO™ system. Single color controls were also prepared for compensation. As shown in FIG. 14, the XPA.42.068 antibody significantly increased levels of CTL within tumors removed from mice, as compared to isotype control antibody. The BM-1, XPA.42.089 and XPA.42.681 antibodies did not exhibit a similar increase in CTL.

The results above demonstrate that the anti-TGFβ antibodies disclosed herein have the ability to decrease tumor volume size as well as modulate immune cells that infiltrate tumors and contribute to tumor growth in vivo. This suggests that the anti-TGFβ antibodies described herein will provide a therapeutic benefit in the treatment of cancer, in particular, in cancers in which any one or more of the immune cells in the examples above infiltrate into the tumor cells.

Example 18. Improvement in NK Cell Cytolytic Activity

A natural killer (NK) cell co-culture system was developed to mimic chronic interaction between NK cells and tumor cells in vivo, for evaluating the ability of the anti-TGFβ antibodies to improve NK cell cytolytic activity. The TGFβ producing mouse mammary carcinoma cell line, 4T1, was used. NK cells were purified from spleens of normal Balb/c mice and co-cultured with CFSE-labeled 4T1 tumor cells for 48 hours in the presence of IL-2 (500 IU/ml) in 6-well plate. Anti-TGFβ and control antibodies were added into the co-culture system and NK cells were harvested 48 hours later. IFNγ production of NK cells was measured right after the co-culture by intracellular staining. NK cells were sorted as CFSE negative cells and their cytolytic activity was analyzed by standard killing assays against the Yac-1 tumor cell line. NK cells were co-cultured with CFSE labeled Yac-1 cells at an effector:target (E:T) ratio of 20:1 for 4 hours in 96-well round bottom plate. Propidium iodide (PI) stain was used to mark cell death.

Figure 15:
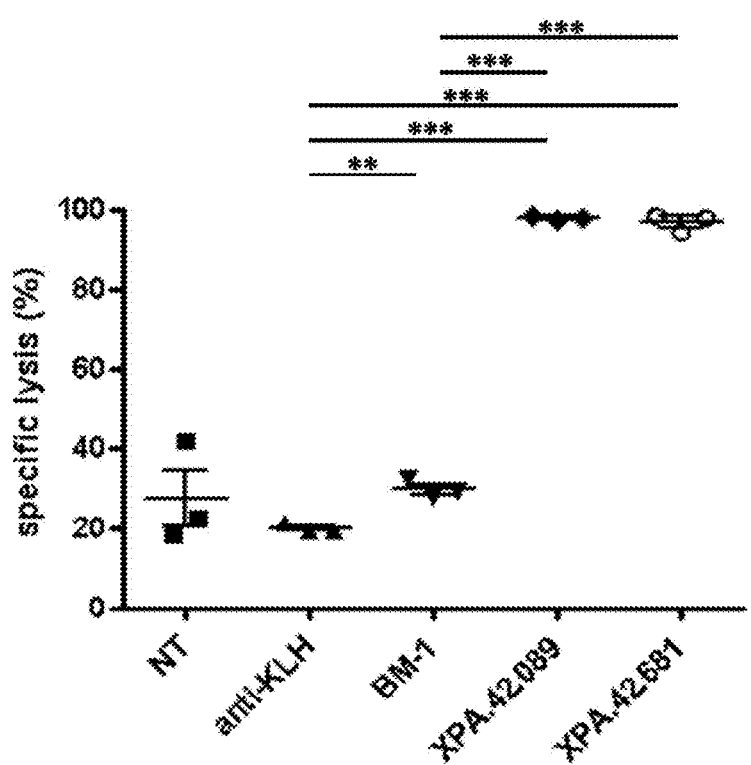
FIG. 15 is a graph showing the in vitro effects of TGFβ antibodies on NK cell cytolytic activity.

NK cells showed an elevated but not significant increase in IFNγ production among antibody treated groups compared to anti-KLH treated group. In the killing assays, at an effector:target ratio of 20:1, the BM-1 antibody and both the XPA.42.089 and XPA.42.681 antibodies significantly improved NK cell cytolytic activity (FIG. 15). Moreover, both the XPA.42.089 and XPA.42.681 antibodies increased the ability of NK cells to kill target tumor cells to 97.8% and 96.7%, which were levels significantly greater than the benchmark comparator ($P<0.0001$). This result indicates that the TGFβ neutralizing antibodies of the present disclosure can significantly improve NK cell cytolytic activity that was dampened by chronic interaction with TGFβ producing tumor cells in vitro.

Example 19. Inhibition of the Tolerogenic Function of CD8+ Dendritic Cells

An in vitro system based on mixed lymphocyte reaction (MLR) was developed to evaluate the ability of anti-TGFβ antibodies to inhibit the tolerogenic function of TGF-β on CD8+ dendritic cells (DC). MLR is a classic experiment used to test DCs antigen presentation without adding external antigens into the system. Spleens from normal Balb/c mice were cut into small fragments and incubated in 10% RPMI and 1 mg/ml collagenase type IV for 1 hour at 37° C. in a shaking incubator. After adding EDTA for additional 5 minutes, the solution was filtered through a nylon mesh. CD11c+ DCs were stained with biotinylated anti-CD11c antibody and positively selected using a biotin purification kit from Stemcell Technologies. CD11c+ DCs were stained with CD8 antibody. CD8+ and CD8− populations were sorted on the BD FACSARIA™ cell sorter. CD8+ DCs were cultured with anti-TGFβ antibodies or control antibody for 24 hours and mixed into CD8− DCs at 1:10 ratio. T cells were purified from normal B6 spleens using a T cell negative selection kit from Stemcell Technologies and labeled with CFSE. Mixed DCs were then co-cultured with B6 T cells for 5 days in 96-well round bottom plates. The immune inhibitory function of CD8+ DCs was evaluated by T cell proliferation. If CD8+ DCs inhibit the ability of CD8− DCs to present antigens, B6 T cells proliferate less. If anti-TGFβ antibodies block autocrine TGFβ and dampen CD8+ DC tolerogenic function, B6 T cells proliferate more.

Figure 16:
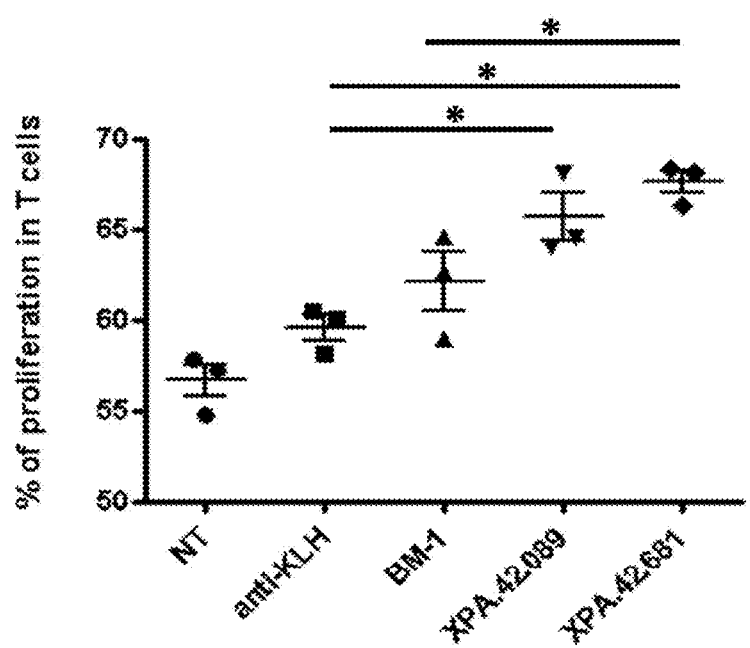
FIG. 16 is a graph showing the effect of TGFβ antibodies on T cell proliferation.

As shown in FIG. 16, little change was observed in T cell proliferation for the BM-1 treated group compared to the anti-KLH control group. In contrast, both the XPA.42.089 and XPA.42.681 antibodies significantly increased T cell proliferation as compared to the control anti-KLH treated group, and the effect of XPA.42.681 on T cell proliferation was significant compared to the benchmark antibody BM-1. These data show that by blocking TGF-β, the tolerogenic effect of CD8+ DCs on immunogenic DC can be reduced, which may provide enhanced antigen presentation by immunogenic DCs.

Example 20. Enhancement of CTL Function

Figure 17A:
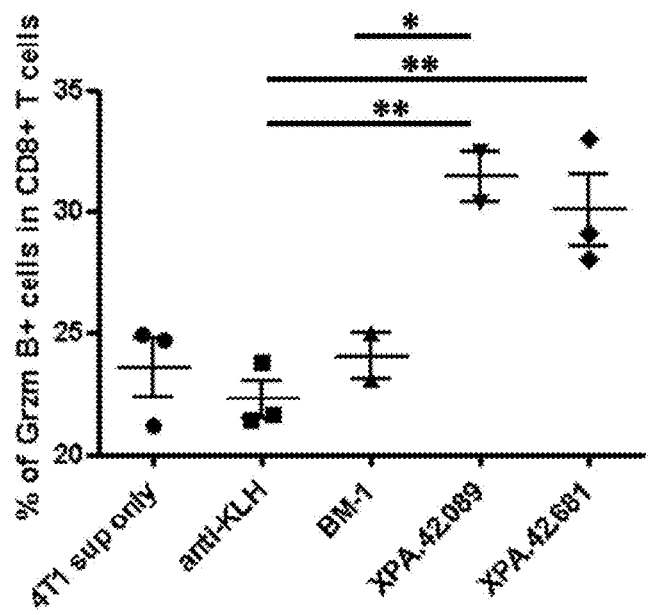
FIGS. 17A-17B show the effect of TGFβ antibodies on CTL activation evaluated by expression of granzyme B (GzmB) (FIG. 17A) and perforin (FIG. 17B).
Figure 17B:
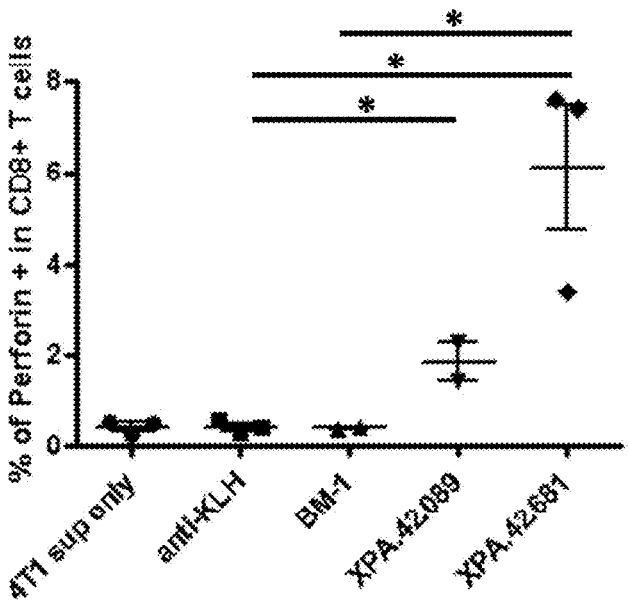

An in vitro system was developed to mimic the activation of CTLs under tumor conditions and determine whether CTL function could be enhanced by the anti-TGFβ antibodies. CTL activation was evaluated by CD25 expression and function by staining of perforin and granzyme B (GzmB) (Massague et al. Cancer Cell 8: 369-380, 2005). T cells were purified from normal Balb/c spleens by T cell negative selection (Stemcell Technologies). MACs beads were coated with anti-CD3 and anti-CD28 antibodies with T cell activation/expansion kit by Miltenyi Biotec (Auburn, Calif.). T cells and anti-CD3 and anti-CD28 coated-MACs beads were co-cultured at a 1:1 ratio at a concentration of 2×10e6/mL in 96-well round bottom plate in the presence of 20 ul of 4T1 culture supernatant for 48 hours, with anti-TGFβ antibodies and control antibody. CTL activation was evaluated with CD25 expression on the cell surface and function was evaluated with the expression of GzmB (FIG. 17A) and perforin (FIG. 17B), determined by intracellular staining using a FoxP3 staining protocol.

Consistent with published data, changes in CD25 expression were not observed between antibody treated groups and the control group. BM-1 treated CTLs showed minimal changes in both GzmB and perforin expression. However, both the XPA.42.089 and XPA.42.681 antibodies significantly increased GzmB expression in CTLs as compared to control anti-KLH treatment (P<0.001). Moreover, the increase in GzmB expression in XPA.42.089 treated CTLs was significantly greater than the comparator BM-1 (P<0.05). For perforin expression, both XPA.42.089 and XPA.42.681 treated CTLs produced significantly more perforin compared to control anti-KLH treated CTLs (P<0.05). In addition, XPA.42.681 improved perforin expression in CTLs significantly more than the BM-1 comparator (P<0.05). Thus, both XPA.42.089 and XPA.42.681 can restore the expression of both GzmB and perforin suppressed by TGF-β secreted from tumor cells in this in vitro culture system, and therefore provides a mechanism to boost CTL function by neutralizing TGFβ produced by tumor cells.

Example 21. Inhibition of MDSC and Treg Function

An in vitro co-culture system is developed to evaluate the effect of myeloid-derived suppressor cells (MDSCs) on the expansion and function of regulatory T cells (Tregs), and the ability of anti-TGFβ antibodies of the present disclosure to inhibit MDSC and Treg activity.

MDSCs are known to suppress the immune response against tumors and promote tumor invasion and metastasis, as well as promote the expansion and function of Tregs, which are known to down-regulate immune responses. Female BALB/c mice are inoculated in the abdominal mammary gland with $7×10^3$ 4 T1 tumor cells in 50 ul 1×PBS. Spleens are harvested on day 21 and MDSCs purified via biotin labeled CD11b antibody and biotin positive selection kit (Stemcell Technologies). At the same time, normal BALB/c spleens are harvested and T cells are purified via a T cell negative selection kit (Stemcell Technologies). The cells are stained with anti-CD4-FITC and anti-CD25-PE. Double positive cells are sorted with a FACSARIA™ cell sorter (BD Bioscience). The Treg population is CFSE labeled and co-cultured with MDSCs from 4T1 tumor injected mice at a 1:1 ratio for 5 days in the presence of anti-TGFβ or control antibodies. The expansion of Tregs is measured by CFSE divisions. To evaluate the effect of MDSCs on Treg function, MDSCs harvested from 4T1 injected BalB/c mice are CFSE-labeled and co-cultured with Tregs for 5 days in the presence of anti-TGFβ or control antibodies. Tregs are sorted as a CFSE negative population from the co-culture. T cells from normal BALB/c mice are CFSE-labeled and plated at $2×10^6$ cells/ml with anti-CD3 and anti-CD28 beads. Sorted Tregs are added into the culture system. The inhibitory function of Tregs is measured by analyzing the number of CFSE divisions of the T cells.

Example 22. Inhibition of Fibrosis by TGFβ Antibodies in a Mouse Model

Antibodies of the present disclosure are also evaluated for their ability to inhibit fibrosis (e.g., lung fibrosis, kidney fibrosis) in animal models of fibrosis.

Kidney Fibrosis

A kidney fibrosis model was used to evaluate the anti-TGFβ antibodies (Ling et al., J. Am. Soc. Nephrol. 14:377-388; 2003). Cyclosporine A (CsA, 30 mg/kg) or olive oil as vehicle control was injected subcutaneously once daily for 4 weeks into 6-7 week old male ICR mice on a low-salt diet (LSD, 50-100 ppm NaCl) to initiate kidney fibrotic disease. Control mice were maintained on a normal diet and did not receive CsA. Anti-TGFβ antibody XPA.42.089 or IgG control antibody was dosed intraperitoneally (2.5 mg/kg, TIW) beginning one day prior to commencing CsA treatment. Animals were euthanized, and serum, urine and kidneys were collected for evaluation of histology and kidney function endpoints.

Histopathologic examination was performed by staining formalin-fixed and paraffin-embedded kidney sections (5-μm) with hematoxylin-eosin (H&E) and Masson trichrome, using standard techniques. Assessment of CsA-induced histopathologic changes may include commonly accepted semiquantitative scoring (Ling et al., Am. J. Physiol. 277:F383-F390, 1999) of coded sections and assessment on the basis of any or all of tubular damage, interstitial infiltrates, thickening of arterioles, tubulointerstitial expansion, and fibrosis, including for example scoring by counting the percentage of the diseased area per kidney section. Sagittal kidney sections from normal control, CsA-injected and XPA.42.089 antibody treated mice were stained with Masson's trichrome stain. Development of fibrosis induced by CsA was observed in the tubulointerstitium of CsA injected mice, but not in the control animals. Additionally an increase in the luminal diameter of some tubules was observed in CsA treated mice. Treatment with the XPA.42.089 antibody reduced the amount of CsA-induced fibrosis observed in the tubulointerstitium and reduced tubule diameter.

Kidney function also may be evaluated by any or all of serum creatinine, blood urea nitrogen, and urine biomarkers of kidney dysfunction.

Figure 18:
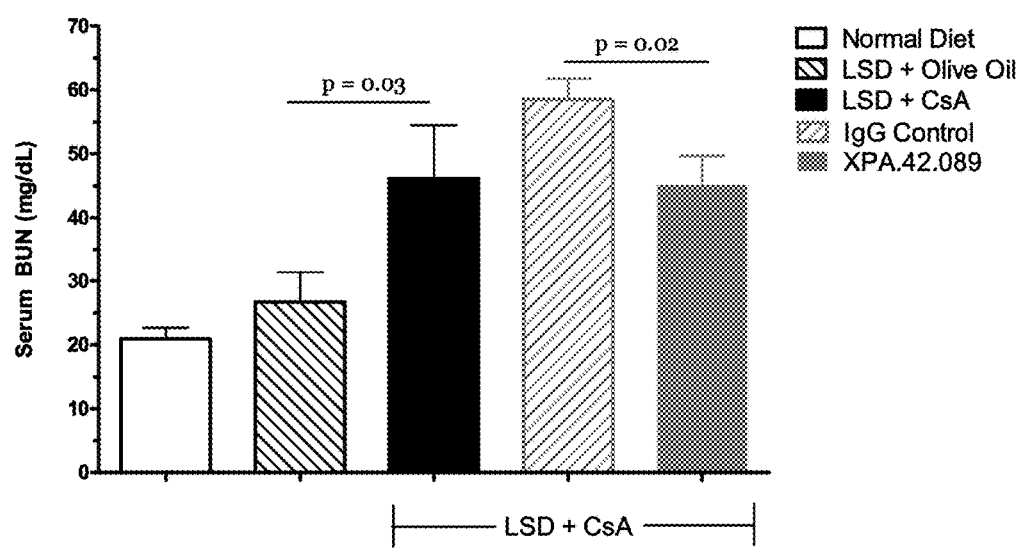
FIG. 18 is a graph showing the effect of TGFβ antibodies on serum blood urea nitrogen (BUN) levels in CsA treated or control animals administered TGFβ antibodies.

Serum blood urea nitrogen (BUN) is an indicator of kidney dysfunction. In this study, BUN was significantly increased in mice exposed to CsA as compared to chow-fed or LSD-fed control mice (FIG. 18). Treatment with XPA.42.089 significantly reduced serum BUN compared to the IgG control antibody.

Figure 19:
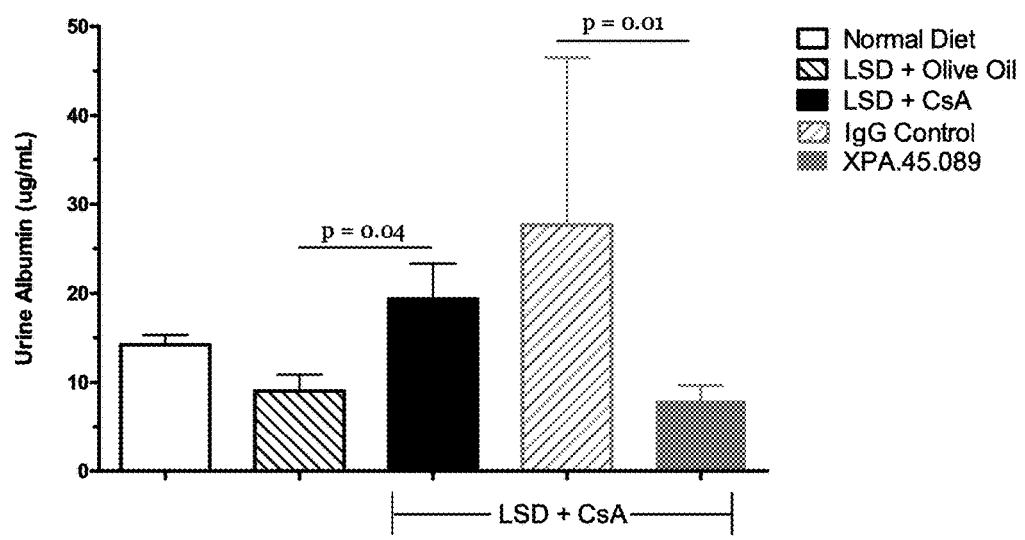
FIG. 19 is a graph showing the effect of TGFβ antibodies on albumin accumulation, which is characteristic of glomerular dysfunctional in the diseased kidney, in the urine of CsA treated or control animals administered TGFβ antibodies.

Albuminuria, or an increase in albumin accumulation in the urine, is characteristic of glomerular dysfunctional in the diseased kidney. In this study, urine albumin was increased nearly four-fold in CsA mice relative to chow-fed or LSD-fed control mice (FIG. 19). Treatment with XPA.42.089 resulted in a significant improvement in albuminuria as compared to IgG control antibody treated mice.

Figure 20:
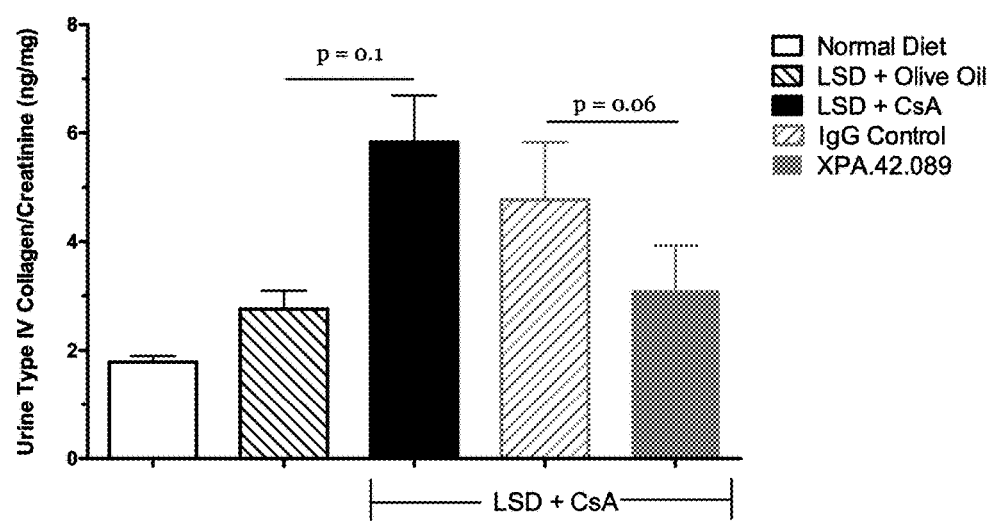
FIG. 20 is a graph showing the effect of TGFβ antibodies on levels of urine type IV Collagen, which reflect the extent of ECM deposition and fibrosis in the kidneys, in the urine of CsA treated or control animals administered TGFβ antibodies.

Levels of urine type IV Collagen, which reflect the extent of ECM deposition and fibrosis in the kidneys, was significantly increased in CsA mice relative to chow-fed or LSD-fed control mice (FIG. 20). Treatment with XPA.42.089 moderately decreased urine type IV collagen compared to IgG control antibody.

Figure 21A:
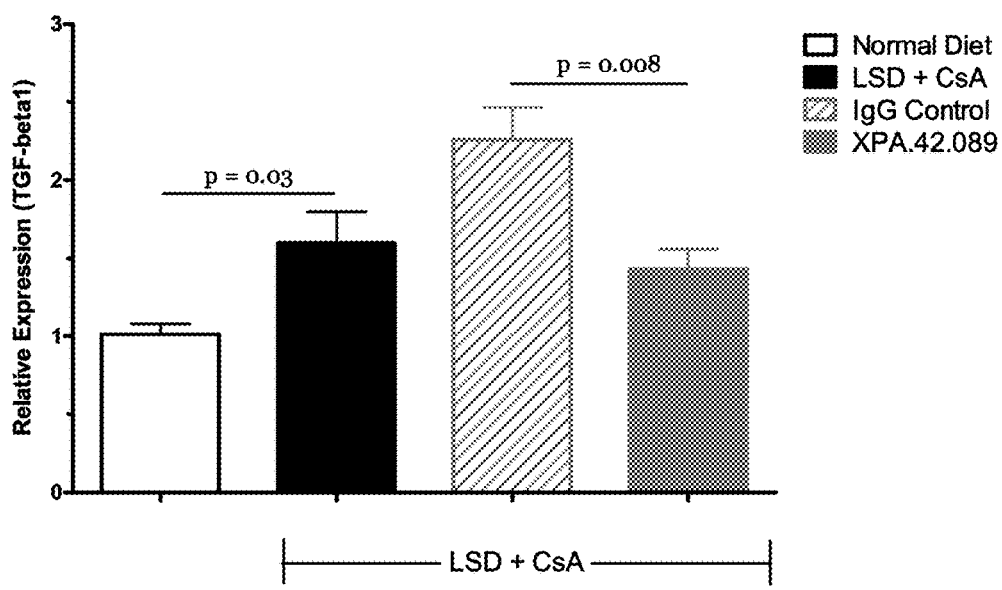
FIG. 21 is a graph showing the effect of TGFβ antibodies on expression of genes involved in fibrosis as assessed by Quantitative RT-PCR performed on kidney tissue. Effects on TGF-β1 expression (FIG. 21A) and type III collagen (FIG. 21B) were assessed in CsA treated or control animals administered TGFβ antibodies.
Figure 21B:
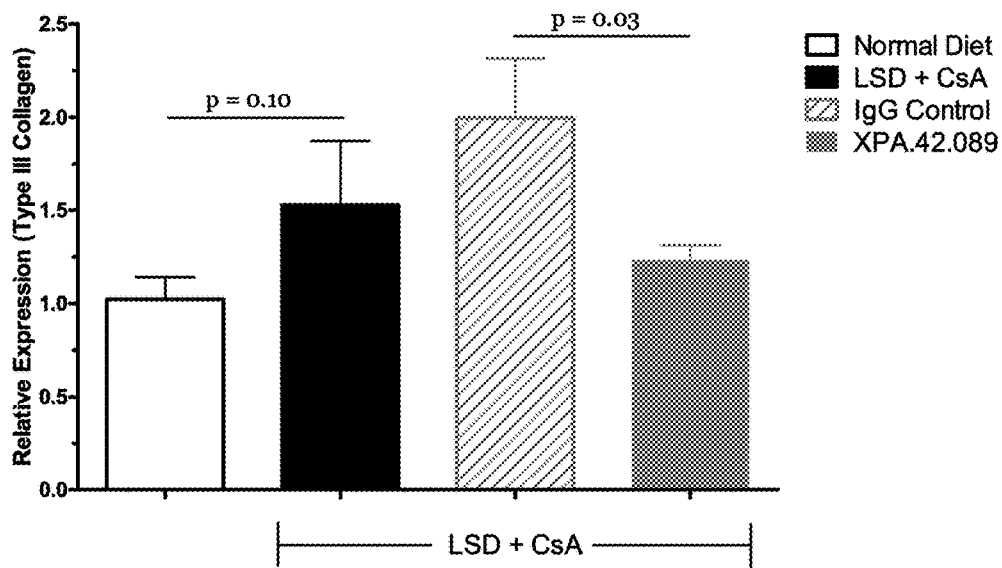

Quantitative RT-PCR was performed on kidney tissue to determine expression of genes involved in fibrosis. Total RNA was isolated from kidneys (cortex and medulla) using the RNeasy Kit (Qiagen, Germantown, Md.) according to the manufacturer's protocol. First-strand cDNA was synthesized using random primers and MULTISCRIBE™ RT (Applied Biosystems, Carlsbad, Calif.). Quantitative RT-PCR was then performed on 2 μl cDNA using SYBR Green mix (Roche) on the LIGHTCYCLER 480 Real Time PCR system (Roche Applied Science, Indianapolis, Ind.). Values were normalized to cyclophilin and calculated using the comparative CT method. TGF-β1 is a potent inducer of fibroblast differentiation and the deposition of ECM proteins, including type III collagen. TGF-β1 expression was nearly two-fold higher in CsA-treated animals when compared to control mice (FIG. 21A). Treatment with XPA.42.089 significantly reduced the expression levels of TGF-β1 in the kidney as compared to IgG control antibody. A similar effect was observed for expression of type III collagen, with a moderate elevation observed in CsA treated mice (FIG. 21B). Treatment with XPA.42.089 resulted in decreased type III collagen expression levels compared to IgG control antibody treated mice.

Lung Fibrosis

A lung fibrosis model may be used, essentially as described by Wilson et al. (J. Exp. Med. 207:535-552; 2010). C57BL/6 mice are anesthetized and instilled intratracheally with 0.15 U bleomycin sulfate (Calbiochem, La Jolla, Calif.) in saline, with or without antibody (e.g., n=10 per group, 500 ug) on days −1, 3 and 5. Animals are sacrificed on day 7 for analysis of lung histology, lung collagen content (e.g., collagen deposition), and inflammatory infiltration. For lung histology, 5-μm sections of paraffin-embedded lung tissue are stained with Masson's Trichrome. Lung injury, measured as bronchoalveolar lavage (BAL) collagen and collagen deposition in lung, is quantified using the Sircol assay. Inflammatory infiltration is measured in the BAL by flow cytometry.

Example 23. Treatment of TGFβ Mediated Ophthalmological Disorders

Anti-TGF-β antibodies of the present disclosure may be used for the treatment of a number of ophthalmological (i.e., eye) diseases and conditions, including for example fibrotic diseases in the eye (e.g., diseases associated with fibroproliferative states).

Neutralization of TGFβ1 in Retinal Pigment Epithelial Cells

Maintenance of the epithelial phenotype is critical for tissue homeostasis. In the retina, de-differentiation of retinal pigment epithelium (RPE) leads to retinal dysfunction and fibrosis, and TGFβ contributes to retinal de-differentiation by a number of mechanisms, some of which are dependent on activation of the SMAD2 pathway. Antibodies of the present disclosure were evaluated for their ability to counteract activation of TGFβ responses in RPE cells, using a pSMAD2 assay.

Retinal Pigment Epithelial (RPE) cells (Lonza #194987) were maintained in Retinal Pigment Epithelial Cell Growth Media (Lonza#00195409). Cells were detached with trypsin, the trpysin was neutralized (Trypsin Neutralization Solution, Lonza#CC-5002), and the cells were pelleted, resuspended at 1e6 cells/mL and plated at 100,000-200,000 cells/well into a 6 well dish. The following day, cells were washed and RPE Basal Media (Lonza#00195406) was added to arrest cells in G0/G1 phase. The next day, cells were treated with 10 ng/ml TGFβ1 (Peprotech #100-21) pre-incubated for 5 minutes with or without anti-TGFβ antibodies XPA.42.068, XPA.42.089, and XPA.42.681, the benchmark antibodies BM-1 and BM-2, or a control anti-KLH-G2 antibody at 10 ug/ml. After 30 minutes at 37° C., cells were lysed in cell lysis buffer (Cell Signaling Technology, Danvers, Mass.) containing 1 mM phenylmethylsulfonyl fluoride (PMSF) added fresh. After rocking 5 minutes at 4° C., cells were scraped off and dispensed into a 96 deep well plate to lyse on ice for 20 minutes. Lysates were spun down at 3K for 5 minutes at 4° C. Lysates were diluted and run according to manufacturers recommendations for phoshpo-SMAD2 (Cell Signaling #7348) and total SMAD2 (Cell Signaling #7244) detection.

Figure 22:
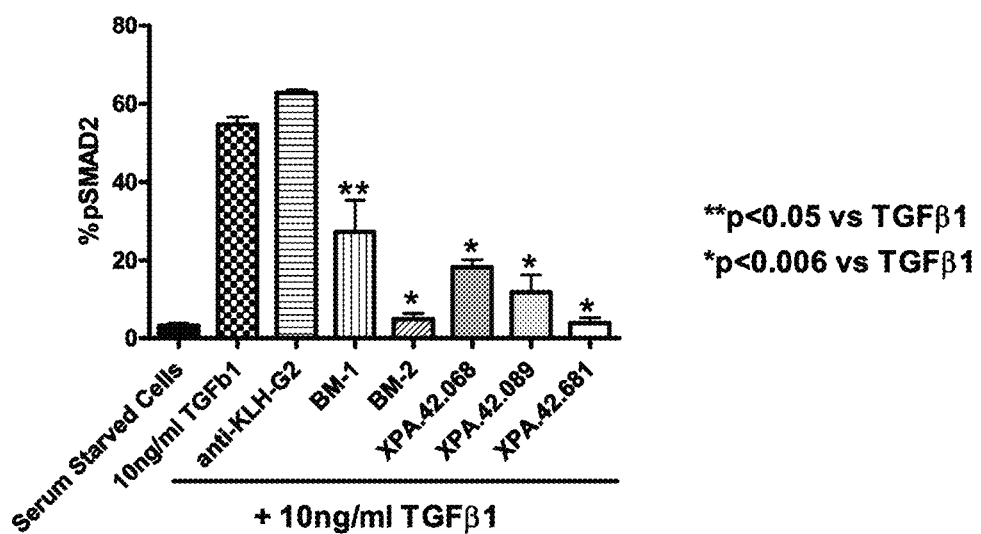
FIG. 22 is a graph showing the effect of TGFβ antibodies on increase in pSMAD2 in retinal pigment epithelium (RPE) cells after administration of TGFβ1.

As shown in FIG. 22, TGFβ1 treatment causes a robust increase in pSMAD2 in RPE cells, which was significantly neutralized by each of the antibodies XPA.42.089, XPA.42.068 and XPA.42.681, and the benchmark antibodies. These data suggest that XPA.42.089, 068 and 681 can counteract TGFβ mediated signaling in RPE cells and indicates the antibodies may be useful for treatment of retinal dysfunctions.

Proliferative Vitreoretinopathy

Proliferative vitreoretinopathy (PVR) is the most common cause of failure in retinal detachment surgery. PVR is characterized by formation of fibrovascular membranes within the vitreous cavity above and beneath the retina, causing subsequent retinal detachment. Various factors contribute to the progression of PVR, and TGFβ is believed to play a pivotal role. TGFβ is abundant in the vitreous of PVR patients, and characteristic functions of TGFβ, such as the induction of epithelial to mesenchymal transition (EMT), stimulation of extracellular matrix production, contraction of cellular membrane, and induction of inflammation, are all negative factors in the progression of PVR.

To evaluate the effect of antibodies of the present disclosure, experimental PVR is induced in a rabbit model (Oshima et al., 2002, Gene Ther. 9:1214-1220; Fastenberg et al., Gene Ther. 2002, 9:1214-1220). Adult pigmented rabbits are anesthetized with an intramuscular injection of isoflurane or ketamine and xylazine. The pupils are dilated with one drop of 10% phenylephrine hydrochloride, 1% tropicamide, and 1% atropine sulfate. One eye of each rabbit is injected with 5.0×10e5 rabbit conjunctival fibroblast cells in 0.1 ml BSS solution in the vitreous cavity through the pars plana. Pars plana vitrectomy will induce the PVR model. Immediately thereafter, a single intravitreal injection of BSS, anti-TGFβ antibody (e.g., XPA.42.089, XPA.42.681, 5 mg) or control antibody (e.g., anti-KLH-G2) is administered to groups of 10 animals, and optionally repeated weekly. All injected eyes are ophthalmoscopically examined on days 1, 3, 5, 7, 10, 14 and 28, with PVR classified into six stages using the clinical criteria described by Fastenberg et al., Am. J. Ophthalmol. 93:565-572, 1982).

Alkali Burn to the Cornea

Ocular trauma in the form of an alkali burn to the cornea is a serious clinical problem and may cause severe and permanent visual impairment. Activation of corneal cells, i.e., keratocytes and epithelial cells, and influx of inflammatory cells such as monocytes/macrophages, are involved in the pathogenesis of injury after alkali tissue damage in the cornea and can lead to persistent epithelial defects. Moreover, breakdown of the basement membrane by matrix metalloproteinases (MMPs, gelatinases) secreted by these cells contributes to the pathogenic ulceration and perforation of the stroma. Conjunctivalization of the corneal surface on the loss of limbal stem cells together with opacification and neovascularization of the corneal stroma all impair the patients' vision in the later healing phases. A number of growth factors and cytokines, including TGF-β, are believed to be involved in the tissue destruction and late scarring that occur in the cornea after alkali burn.

To evaluate the effect of antibodies of the present disclosure, a mouse alkali burn model is used (Saika et al., Am. J. Pathol. 2005, 166:1405-18). Briefly, three μl of 1 N sodium hydroxide solution is applied to the right eye of adult C57BL/6 mice (n=72) to produce an ocular surface alkali burn under both general and topical anesthesia. Anti-TGF-β antibodies (e.g., XPA.42.089, XPA.42.681) or control antibody (e.g., anti-KLH-G2) are administered (n=24/group) at 2 hours and days 5, 10, and 15 after the alkali exposure. Fluorescein staining of the cornea is used to visualize surface defects (e.g., injured epithelium). After corneal fluroescein examination, the eye globe is enucleated 2 hours after labeling with bromodeoxyuridine and processed for histological examination in either paraffin or cryosections at days 3, 5, 10, and 20.

Lens Fibrosis

Following injury, lens epithelial cells undergo EMT, which contributes to the formation of fibrotic tissue in the injured lens. A similar phenomenon is observed in the human lens capsule following cataract extraction and implantation of an artificial intraocular lens. Such an EMT-related fibrotic reaction is clinically unfavorable since it may cause opacification and contraction of the remaining anterior lens capsule, as well as opacification in the posterior capsule. Eye aqueous humor contains abundant TGF-β and a role has been suggested for TGF-β in injury-related EMT in lens epithelial cells.

To evaluate the effect of antibodies of the present disclosure, experimental corneal fibrosis is induced in a mouse model (Saika, et al., Am J Pathol. 2004, 164:651-663). Adult mice (4 to 6 weeks old) are anesthetized with an intraperitoneal injection of pentobarbital sodium (70 mg/kg). A small incision is made in the central anterior capsule with the blade part of a 26-gauge hypodermic needle through a corneal incision in the right eye after topical application of mydriatics and oxybuprocaine eyedrop as anesthetic. Immediately thereafter, anti-TGFβ antibodies (e.g., XPA.42.089, XPA.42.681) or control antibody (e.g., anti-KLH-G2) (n=24/group) are administered to the eyes twice weekly for the duration of the study. The left eye serves as an uninjured control. The depth of injury is ~300 μm, or approximately one-fourth of the length of the blade part of the needle, which leads to the formation of fibrotic tissue around the capsular break. After instillation of ofloxacin ointment, the animals are allowed to heal for 6 hours to 8 weeks. Proliferating cells are labeled by an intraperitoneal injection of bromodeoxyuridine, followed by sacrifice of the animals 2 hours later and enucleation of each eye for analysis.

Postoperative Glaucoma Surgery

The major determinant of the long-term outcome of glaucoma surgery is the wound-healing response. Excessive postoperative scarring at the level of the conjunctiva and sclerostomysites is associated with poor postoperative pressure control. Use of the antiproliferative agents 5-fluourouracil (5-FU) and mitomycin C (MMC) in such surgery can also cause widespread cell death and apoptosis and can result in corneal erosions and cystic avascular blebs.

To evaluate the effect of antibodies of the present disclosure on these conditions associated with glaucoma surgery, a rabbit model is used (Mead et al., Invest. Ophthalmol. Vis. Sci. 2003, 44:3394-3401). Glaucoma filtration surgery is performed on the left eyes of New Zealand White rabbits (12 and 14 weeks old) under general anesthesia (ketamine and xylazine). A partial-thickness 8-0 silk corneal traction suture is placed at 12 o'clock, to gain exposure to the superior conjunctiva. A fornix-based conjunctival flap is raised, and blunt dissection of the subconjunctival space is performed to a distance of 15 mm behind the limbus. An MVR blade is used to fashion a partial thickness scleral tunnel, starting 4 mm behind the limbus and continuing until the blade is just visible in the anterior cornea stroma. A 22-gauge/25-mm intravenous cannula is then passed through the scleral tunnel until the cannula needle is visible in the clear cornea. The cannula needle enters the anterior chamber, the cannula is advanced to the midpupillary area, and the needle is withdrawn. Finally, the cannula is trimmed and beveled at its scleral end so that it protrudes 1 mm from the insertion point, and a 10-0 nylon suture is used to fix the tube to the scleral surface. The conjunctival incision is closed with two interrupted sutures and a central mattress-type 10-0 nylon suture on a needle to give a water-tight closure. One drop of atropine sulfate 1% and betamethasone sodium phosphate 0.1%, neomycin sulphate 0.5% ointment is instilled at the end of surgery. Animals are then randomly allocated to receive a postoperative course of subconjunctival injections (100 μL) of anti-TGFβ antibody (e.g., XPA.42.089, XPA.42.681) or control antibody (e.g., anti-KLH-G2) (e.g., 5 mg/mL; 16/group). The subconjunctival injections are given on days 2, 3, 4, 7, 9, 11, and 14 after surgery (day 0) under topical anesthesia (proxymetacaine hydrochloride 0.5% eye drops, 1 drop per eye), using a 30-gauge needle. Antibody is injected 5 mm behind the limbus at the nasal margin of the superior rectus muscle. 5-FU is administered 180° from the site of surgery.

Measurement of intraocular pressure in both eyes is made with a handheld tonometer after topical instillation of 0.5% proxymetacaine HCl eye drops. The conjunctival appearance and the drainage area are observed. All animals are examined by a masked observer at set times after surgery. Assessment of both eyes (contralateral untreated eye used as control) is made daily from days 0 to 4 and thereafter at regular periods, at least twice weekly. Bleb characteristics, including length, width, and height, are measured with calipers, and intraocular pressure is recorded. The drainage bleb vascularity characteristics are graded by dividing the conjunctival areas into quadrants and scoring the appearance (0, avascular; +1, normal vascularity; +2, hyperemic; and +3, very hyperemic). Slit lamp examination is performed to identify both anterior chamber activity (0, quiet; 1, cells; 2, fibrin; and 3, hypopyon) and anterior chamber depth, which is recorded as deep (+2), shallow (+1), or flat (0). An assessment of the duration of corneal epitheliopathy is made after topical installation of lignocaine fluorescein into the left eye and is graded according to the area of the cornea affected (0, nil; 1, <5%; 2, <50%; 3, <75%; 4, <90%; 5, up to 100%). Bleb survival is taken as the primary efficacy end point. Bleb failure is defined as the appearance of a flat, vascularized, and scarred bleb in the presence of a deep anterior chamber. Bleb area and height, anterior chamber depth and activity, and conjunctival vascularity per quadrant are all analyzed. Tissues are also processed for histological examination (e.g., subconjunctival collagen deposition) from some animals.

It is expected that anti-TGFβ antibodies disclosed herein inhibit TGFβ activity during fibrotic incidences in the eye thereby decreasing fibrotic deposition and improving symptoms associated with fibrosis of the eye.

Numerous modifications and variations in the disclosure as set forth in the above illustrative examples are expected to occur to those skilled in the art. Consequently only such limitations as appear in the appended claims should be placed on the disclosure.

What is claimed:

1. An antibody that competes with reference antibody that binds transforming growth factor beta (TGFβ)1, TGFβ2 and TGFβ3 comprising
    (a) a heavy chain CDR1 amino acid sequence set forth in SEQ ID NO: 19;
    (b) a heavy chain CDR2 amino acid sequence set forth in SEQ ID NO: 20;
    (c) a heavy chain CDR3 amino acid sequence set forth in SEQ ID NO: 21;
    (d) a light chain CDR1 amino acid sequence set forth in SEQ ID NO: 22;
    (e) a light chain CDR2 amino acid sequence set forth in SEQ ID NO: 23; and
    (f) a light chain CDR3 amino acid sequence set forth in SEQ ID NO: 24,
    wherein the competing antibody also binds to TGF-β1, TGFβ2 and TGFβ3.

2. An antibody that competes with reference antibody having
    (a) a heavy chain variable region comprising at least a CDR1 amino acid sequence set out in SEQ ID NO: 19, a CDR2 amino acid sequence set out in SEQ ID NO: 20, and a CDR3 amino acid sequence set out in SEQ ID NO: 21; and
    (b) a light chain variable region comprising at least a CDR1 amino acid sequence set out in SEQ ID NO: 22, a CDR2 amino acid sequence set out in SEQ ID NO: 23, and a CDR3 amino acid sequence set out in SEQ ID NO: 24,
    for binding to transforming growth factor beta (TGF-β)1, TGFβ2 and TGFβ3.

3. The antibody of claim 2, wherein the reference antibody that binds TGFβ1, TGFβ2 and TGFβ3 comprises a heavy chain variable region amino acid sequence set out in SEQ ID NO: 6 and a light chain variable region amino acid sequence set out in SEQ ID NO: 8.

4. The antibody of claim 2 that binds TGFβ1 and TGFβ2 with an affinity between a Kd of $10^{-6}$ to $10^{-12}$ M.

5. The antibody of claim 2, wherein the antibody binds to TGFβ1 and TGFβ2 with greater affinity than it does to TGFβ3.

6. The antibody of claim 2, wherein the antibody neutralizes activity of TGFβ1 and TGFβ2 to a greater extent than it does to TGFβ3.

7. The antibody of claim 2, in which one or more heavy chain framework amino acids have been replaced with corresponding amino acid(s) from another human antibody amino acid sequence.

8. The antibody of claim 2, further comprising a heavy chain constant region, wherein the heavy chain constant region is a modified or unmodified IgG, IgM, IgA, IgD, IgE, a fragment thereof, or combinations thereof.

9. The antibody of claim 2, in which one or more light chain framework amino acids have been replaced with corresponding amino acid(s) from another human antibody amino acid sequence.

10. A sterile pharmaceutical composition comprising the antibody of claim 2 and a pharmaceutically acceptable carrier.

11. A method for treating a disease, condition or disorder associated with TGFβ expression comprising the step of administering to a subject in need thereof a therapeutically effective amount of the antibody of claim 2 or the pharmaceutical composition of claim 10.

12. A method for treating cancer comprising administering to a subject in need thereof a therapeutically effective amount of the antibody of claim 2 or the pharmaceutical composition of claim 10.

13. The method of claim 12, wherein the antibody or composition increases the number of natural killer (NK) cells in a tumor and/or improves NK cell cytolytic activity.

14. The method of claim 12, wherein the antibody or composition decreases the number of regulatory T cells in a tumor and/or inhibits regulatory T cell function.

15. The method of claim 12, wherein the antibody or composition increases the number of cytotoxic T cells (CTLs) in a tumor and/or enhances CTL function.

16. The method of claim 12, wherein the antibody decreases the number of myeloid-derived suppressor cells (MDSC) in a tumor and/or inhibits MDSC function.

17. The method of claim 12, wherein the antibody decreases the number of dendritic cells (DC) in a tumor and/or inhibits the tolerogenic function of dendritic cells.

18. The method of claim 12, wherein the cancer is selected from the group consisting of lung cancer, prostate cancer, breast cancer, hepatocellular cancer, esophageal cancer, colorectal cancer, pancreatic cancer, bladder cancer, kidney cancer, ovarian cancer, stomach cancer, fibrotic cancer, glioma and melanoma.

19. The method of claim 18 wherein the cancer is melanoma.

20. A method for treating fibrosis comprising administering to a subject in need thereof a therapeutically effective amount of the antibody of claim 2 or the pharmaceutical composition of claim 10.

* * * * *

UNITED STATES PATENT AND TRADEMARK OFFICE
CERTIFICATE OF CORRECTION

PATENT NO.       : 9,714,285 B2
APPLICATION NO.  : 14/808666
DATED            : July 25, 2017
INVENTOR(S)      : Daniel Bedinger et al.

Page 1 of 2

It is certified that error appears in the above-identified patent and that said Letters Patent is hereby corrected as shown below:

Title page, below abstract, delete "20 Claims, 22 Drawing Sheets" and insert --19 Claims, 22 Drawing Sheets--.

Column 117, Line 50-Column 120, Line 29, delete Claim 1-20 and insert the following Claims 1-19. Claim 1 has been deleted.

--1. An antibody that competes with a reference antibody having
    (a) a heavy chain variable region comprising at least a CDR1 amino acid sequence set out in SEQ ID NO: 19, a CDR2 amino acid sequence set out in SEQ ID NO: 20, and a CDR3 amino acid sequence set out in SEQ ID NO: 21; and
    (b) a light chain variable region comprising at least a CDR1 amino acid sequence set out in SEQ ID NO: 22, a CDR2 amino acid sequence set out in SEQ ID NO: 23, and a CDR3 amino acid sequence set out in SEQ ID NO: 24,
    for binding to transforming growth factor beta (TGF-β)1, TGFβ2 and TGFβ3.

2. The antibody of claim 1, wherein the reference antibody that binds TGFβ1, TGFβ2 and TGFβ3 comprises a heavy chain variable region amino acid sequence set out in SEQ ID NO: 6 and a light chain variable region amino acid sequence set out in SEQ ID NO: 8.

3. The antibody of claim 1 that binds TGFβ1 and TGFβ2 with an affinity between a Kd of $10^{-6}$ to $10^{-12}$ M.

4. The antibody of claim 1, wherein the antibody binds to TGFβ1 and TGFβ2 with greater affinity than it does to TGFβ3.

5. The antibody of claim 1, wherein the antibody neutralizes activity of TGFβ1 and TGFβ2 to a greater extent than it does to TGFβ3.

6. The antibody of claim 1, in which one or more heavy chain framework amino acids have been replaced with corresponding amino acid(s) from another human antibody amino acid sequence.

Signed and Sealed this
First Day of May, 2018

Andrei Iancu
*Director of the United States Patent and Trademark Office*

7. The antibody of claim 1, further comprising a heavy chain constant region, wherein the heavy chain constant region is a modified or unmodified IgG, IgM, IgA, IgD, IgE, a fragment thereof, or combinations thereof.

8. The antibody of claim 1, in which one or more light chain framework amino acids have been replaced with corresponding amino acid(s) from another human antibody amino acid sequence.

9. A sterile pharmaceutical composition comprising the antibody of claim 1 and a pharmaceutically acceptable carrier.

10. A method for treating a disease, condition or disorder associated with TGFβ expression comprising the step of administering to a subject in need thereof a therapeutically effective amount of the antibody of claim 1 or the pharmaceutical composition of claim 9.

11. A method for treating cancer comprising administering to a subject in need thereof a therapeutically effective amount of the antibody of claim 1 or the pharmaceutical composition of claim 9.

12. The method of claim 11, wherein the antibody or composition increases the number of natural killer (NK) cells in a tumor and/or improves NK cell cytolytic activity.

13. The method of claim 11, wherein the antibody or composition decreases the number of regulatory T cells in a tumor and/or inhibits regulatory T cell function.

14. The method of claim 11, wherein the antibody or composition increases the number of cytotoxic T cells (CTLs) in a tumor and/or enhances CTL function.

15. The method of claim 11, wherein the antibody decreases the number of myeloid-derived suppressor cells (MDSC) in a tumor and/or inhibits MDSC function.

16. The method of claim 11, wherein the antibody decreases the number of dendritic cells (DC) in a tumor and/or inhibits the tolerogenic function of dendritic cells.

17. The method of claim 11, wherein the cancer is selected from the group consisting of lung cancer, prostate cancer, breast cancer, hepatocellular cancer, esophageal cancer, colorectal cancer, pancreatic cancer, bladder cancer, kidney cancer, ovarian cancer, stomach cancer, fibrotic cancer, glioma and melanoma.

18. The method of claim 17 wherein the cancer is melanoma.

19. A method for treating fibrosis comprising administering to a subject in need thereof a therapeutically effective amount of the antibody of claim 1 or the pharmaceutical composition of claim 9.--.